(12) United States Patent
Super et al.

(10) Patent No.: US 11,208,496 B2
(45) Date of Patent: *Dec. 28, 2021

(54) ANTI-CD19 ANTIBODIES WITH REDUCED IMMUNOGENICITY

(71) Applicant: CANCER RESEARCH TECHNOLOGY LTD., London (GB)

(72) Inventors: Michael Super, Lexington, MA (US); Jonathan Davis, Auburndale, MA (US); Pascal Andre Stein, Boston, MA (US)

(73) Assignee: Cancer Research Technology LTD., London (GB)

( * ) Notice: Subject to any disclaimer, the term of this patent is extended or adjusted under 35 U.S.C. 154(b) by 217 days.

This patent is subject to a terminal disclaimer.

(21) Appl. No.: 16/126,296

(22) Filed: Sep. 10, 2018

(65) Prior Publication Data

US 2019/0241671 A1 Aug. 8, 2019

Related U.S. Application Data

(60) Continuation of application No. 14/620,955, filed on Feb. 12, 2015, now Pat. No. 10,072,092, which is a division of application No. 14/222,517, filed on Mar. 21, 2014, now Pat. No. 8,957,195, which is a division of application No. 11/648,505, filed on Dec. 29, 2006, now Pat. No. 8,691,952.

(60) Provisional application No. 60/755,609, filed on Dec. 30, 2005.

(51) Int. Cl.

| C07K 16/00 | (2006.01) |
|---|---|
| C12P 21/08 | (2006.01) |
| A61K 39/395 | (2006.01) |
| A61K 39/40 | (2006.01) |
| C07K 16/30 | (2006.01) |
| C07K 16/28 | (2006.01) |
| C07K 1/00 | (2006.01) |
| A61K 39/00 | (2006.01) |

(52) U.S. Cl.
CPC .......... C07K 16/30 (2013.01); A61K 39/3955 (2013.01); C07K 16/2803 (2013.01); C07K 16/2866 (2013.01); C07K 16/2896 (2013.01); A61K 2039/505 (2013.01); C07K 2317/24 (2013.01); C07K 2317/41 (2013.01); C07K 2317/56 (2013.01); C07K 2317/567 (2013.01); C07K 2317/732 (2013.01)

(58) Field of Classification Search
None
See application file for complete search history.

(56) References Cited

U.S. PATENT DOCUMENTS

| 4,196,265 A | 4/1980 | Koprowski et al. |
|---|---|---|
| 4,676,980 A | 6/1987 | Segal et al. |
| 4,816,567 A | 3/1989 | Cabilly et al. |
| 4,946,778 A | 8/1990 | Ladner et al. |
| 4,975,369 A | 12/1990 | Beavers et al. |
| 5,082,658 A | 1/1992 | Palladino |
| 5,091,513 A | 2/1992 | Huston et al. |
| 5,114,711 A | 5/1992 | Bell et al. |
| 5,116,964 A | 5/1992 | Capon et al. |
| 5,196,320 A | 3/1993 | Gillies |
| 5,225,538 A | 7/1993 | Capon et al. |
| 5,225,539 A | 7/1993 | Winter |
| 5,258,498 A | 11/1993 | Huston et al. |
| 5,314,995 A | 5/1994 | Fell, Jr. et al. |
| 5,359,035 A | 10/1994 | Habermann |
| 5,399,346 A | 3/1995 | Anderson et al. |
| 5,428,130 A | 6/1995 | Capon et al. |
| 5,514,582 A | 5/1996 | Capon et al. |
| 5,541,087 A | 7/1996 | Lo et al. |
| 5,585,089 A | 12/1996 | Queen et al. |
| 5,585,097 A | 12/1996 | Bolt et al. |
| 5,601,819 A | 2/1997 | Wong et al. |
| 5,645,835 A | 7/1997 | Fell, Jr. et al. |
| 5,650,150 A | 7/1997 | Gillies |
| 5,677,425 A | 10/1997 | Bodmer et al. |
| 5,679,543 A | 10/1997 | Lawlis |
| 5,712,120 A | 1/1998 | Rodriguez et al. |
| 5,723,125 A | 3/1998 | Chang et al. |
| 5,726,044 A | 3/1998 | Lo et al. |
| 5,770,195 A | 6/1998 | Hudziak et al. |
| 5,807,715 A | 9/1998 | Morrison et al. |
| 5,827,516 A | 10/1998 | Urban et al. |
| 5,827,703 A | 10/1998 | Debs et al. |
| 5,837,821 A | 11/1998 | Wu |

(Continued)

FOREIGN PATENT DOCUMENTS

| AU | 21725/88 A | 3/1989 |
|---|---|---|
| EP | 0294703 | 12/1988 |

(Continued)

OTHER PUBLICATIONS

Rudikoff et al. PNAS 1982, 79:1979-1983. (Year: 1982).*
Vajdos et al. J. Mol. Biol. 2002, 320:415-428. (Year: 2002).*
Amit et al. Science vol. 233 747-753 . (Year: 1986).*
Patent Board Decision mailed on Nov. 13, 2013 in the Parent U.S. Pat. No. 8,691,952 , pp. 1-11. (Year: 2013).*
Batova et al., (1999), "The Ch14.18-GM-CSF Fusion Protein is Effective at Mediating Antibody-Dependent Cellular Cytotoxicity and Complement-Dependent Cytotoxicity in Vitro," Clinical Cancer Research, 5:4259-4263.

(Continued)

*Primary Examiner* — Chun W Dahle
(74) *Attorney, Agent, or Firm* — Mintz, Levin, Cohn, Ferris, Glovsky and Popeo, P.C.

(57) ABSTRACT

Anti-CD19 B4 antibodies with modified variable regions are disclosed. The modified anti-CD19 variable region polypeptides have alterations to one or more framework regions or complementarity determining regions of the heavy chain variable region or light chain variable region, thereby to reduce a T-cell response.

1 Claim, 14 Drawing Sheets

Specification includes a Sequence Listing.

(56) References Cited

U.S. PATENT DOCUMENTS

| | | | |
|---|---|---|---|
| 5,843,423 A | 12/1998 | Lyman et al. | |
| 5,888,773 A | 3/1999 | Jost et al. | |
| 5,908,626 A | 6/1999 | Chang et al. | |
| 6,100,387 A | 8/2000 | Herrmann et al. | |
| 6,291,158 B1 | 9/2001 | Winter et al. | |
| 6,309,636 B1 | 10/2001 | do Couto et al. | |
| 6,335,176 B1 | 1/2002 | Inglese et al. | |
| 6,383,487 B1* | 5/2002 | Amlot | A61P 31/12 424/181.1 |
| 6,475,717 B1 | 11/2002 | Enssle et al. | |
| 6,617,135 B1 | 9/2003 | Gillies et al. | |
| 6,627,615 B1 | 9/2003 | Debs et al. | |
| 6,646,113 B1 | 11/2003 | Dreyfuss et al. | |
| 6,736,056 B1 | 5/2004 | Marek | |
| 6,737,056 B1 | 5/2004 | Presta | |
| 6,838,260 B2 | 1/2005 | Gillies et al. | |
| 6,969,517 B2 | 11/2005 | Gillies et al. | |
| 6,992,174 B2 | 1/2006 | Gillies et al. | |
| 7,067,110 B1 | 6/2006 | Gillies et al. | |
| 7,091,321 B2 | 8/2006 | Gillies et al. | |
| 7,141,651 B2 | 11/2006 | Gillies et al. | |
| 7,148,321 B2 | 12/2006 | Gillies et al. | |
| 7,169,904 B2 | 1/2007 | Gillies et al. | |
| 7,186,804 B2 | 3/2007 | Gillies et al. | |
| 8,691,952 B2* | 4/2014 | Super | A61P 35/00 530/387.1 |
| 2002/0034765 A1 | 3/2002 | Daugherty et al. | |
| 2002/0037558 A1 | 3/2002 | Lo et al. | |
| 2002/0081664 A1 | 6/2002 | Lo et al. | |
| 2002/0146388 A1 | 10/2002 | Gillies | |
| 2002/0147311 A1 | 10/2002 | Gillies et al. | |
| 2002/0193570 A1 | 12/2002 | Gillies et al. | |
| 2003/0044423 A1 | 3/2003 | Gillies et al. | |
| 2003/0049227 A1 | 3/2003 | Gillies et al. | |
| 2003/0105294 A1 | 6/2003 | Gillies et al. | |
| 2003/0133939 A1 | 7/2003 | Ledbetter et al. | |
| 2003/0139365 A1 | 7/2003 | Lo et al. | |
| 2003/0139575 A1 | 7/2003 | Gillies | |
| 2003/0157054 A1 | 8/2003 | Gillies et al. | |
| 2003/0166163 A1 | 9/2003 | Gillies | |
| 2003/0166877 A1 | 9/2003 | Gillies et al. | |
| 2004/0033210 A1 | 2/2004 | Gillies | |
| 2004/0043457 A1 | 3/2004 | Schumacher et al. | |
| 2004/0053366 A1 | 3/2004 | Lo et al. | |
| 2004/0072299 A1 | 4/2004 | Gillies et al. | |
| 2004/0082039 A1 | 4/2004 | Gillies et al. | |
| 2004/0180035 A1 | 9/2004 | Gillies | |
| 2004/0180386 A1 | 9/2004 | Carr et al. | |
| 2004/0203100 A1 | 10/2004 | Gillies et al. | |
| 2005/0042729 A1 | 2/2005 | Lo et al. | |
| 2005/0069521 A1 | 3/2005 | Gillies et al. | |
| 2005/0137384 A1 | 6/2005 | Gillies et al. | |
| 2005/0164352 A1 | 7/2005 | Lauder et al. | |
| 2005/0192211 A1 | 9/2005 | Gillies et al. | |
| 2005/0202021 A1 | 9/2005 | Gillies | |
| 2005/0202538 A1 | 9/2005 | Gillies et al. | |
| 2005/0244418 A1 | 11/2005 | Gillies et al. | |
| 2005/0261229 A1 | 11/2005 | Gillies et al. | |
| 2006/0025573 A1 | 2/2006 | Gillies et al. | |
| 2006/0034836 A1 | 2/2006 | Gillies et al. | |
| 2006/0141581 A1 | 6/2006 | Gillies et al. | |
| 2006/0194952 A1 | 8/2006 | Gillies et al. | |
| 2006/0228332 A1 | 10/2006 | Gillies et al. | |
| 2006/0263856 A1 | 11/2006 | Gillies et al. | |
| 2006/0280738 A1 | 12/2006 | Tedder | |
| 2007/0036752 A1 | 2/2007 | Gillies et al. | |

FOREIGN PATENT DOCUMENTS

| | | |
|---|---|---|
| EP | 0308936 | 3/1989 |
| EP | 0314317 | 5/1989 |
| EP | 0318554 | 6/1989 |
| EP | 0326120 | 8/1989 |
| EP | 0344134 | 11/1989 |
| EP | 0428596 | 5/1991 |
| EP | 0439095 | 7/1991 |
| EP | 0511747 | 11/1992 |
| EP | 0519596 | 12/1992 |
| EP | 0601043 | 6/1994 |
| EP | 0659439 | 6/1995 |
| EP | 0699755 | 3/1996 |
| EP | 1088888 | 4/2001 |
| EP | 1176195 | 1/2002 |
| GB | 2188638 A | 10/1987 |
| JP | 2005046143 A | 2/2005 |
| WO | WO-88/07089 | 9/1988 |
| WO | WO-88/09344 | 12/1988 |
| WO | WO-89/09620 | 10/1989 |
| WO | WO-91/04329 | 4/1991 |
| WO | WO-91/08298 | 6/1991 |
| WO | WO-91/13166 | 9/1991 |
| WO | WO-92/02240 | 2/1992 |
| WO | WO-92/08495 | 5/1992 |
| WO | WO-92/08801 | 5/1992 |
| WO | WO-92/10755 | 6/1992 |
| WO | WO-92/16562 | 10/1992 |
| WO | WO-93/03157 | 2/1993 |
| WO | WO-94/25609 | 11/1994 |
| WO | WO-95/05468 | 2/1995 |
| WO | WO-96/08570 | 3/1996 |
| WO | WO-97/00317 | 1/1997 |
| WO | WO-97/24137 | 7/1997 |
| WO | WO-97/30089 | 8/1997 |
| WO | WO-98/52976 | 11/1998 |
| WO | WO-98/59244 | 12/1998 |
| WO | WO-99/03887 | 1/1999 |
| WO | WO-99/29732 | 6/1999 |
| WO | WO-00/01822 | 1/2000 |
| WO | WO-00/34317 | 6/2000 |
| WO | WO-02/056910 | 7/2002 |
| WO | WO-02/069232 | 9/2002 |
| WO | WO-02/079232 | 10/2002 |
| WO | WO-2005/016969 | 2/2005 |

OTHER PUBLICATIONS

Business Wire, Copyright 1998, Gale Group, Oct. 9, 1998, p. 1.
Rudikoff et al. PNAS 1982 vol. 79, pp. 1979-1983.
Vajdos et al. JMB (2002) 320, 415428.
Amit et al Science 1986. vol. 233 747-753.
Abaza et al., (1992), Effects of Amino Acid Substitutions Outside an.
Antigenic Site on Protein Binding to Monoclonal Antibodies of Pre-determined Specificity Obtained by Peptide Immunization: Demonstration with Region 94-100 (Antigenic Site 3) of Myoglobin, Journal of Protein Chemistry, 11(5)433-444.
Adkins et al., (1998), "Edrecolomab (Monoclonal Antibody 17-1A),"Drugs, 56(4):619-626.
Altschul et al., (1990), "Basic Local Alignment Search Tool," J. Mol. Biol., 215(3)403-10.
Angal et al., (1993), "A Single Amino Acid Substitution Abolishes the Heterogeneity of Chimeric Mouse/Human (IgG4) Antibody," Mol. Immunol., 30(1):105-108.
Burgess et al., (1990), "Possible Dissociation of the Heparin-Binding and Mitogenic Activities of Heparin-Binding (Acidic Fibroblast) Growth Factor-1 from Its Receptor-Binding Activities by Site-Di-rected Mutagenesis of a Single Lysine Residue," Journal of Cell Biology, 111:2129-2138.
Capon et al., (1989), "Designing CD4 Immunoadhesins for AIDS Therapy," Nature, 337:525-531.
Caton et al., (1986), "Structural and Functional Implications of a Restricted Antibody Response to a Defined Antigenic Region on the Influenza Virus Hemagglutinin," The EMBO Journal, 5(7):1577-1587.
Chamow et al., (1996), "Immunoadhesins: Principles and Applications," Trends in Biotechnology, 14(2):52-60.
Chan et al., (1992), "Mechanisms of IFN-y Induction by Natural Killer Cell Stimulatory Factor (NKSF/IL-12). Role of Transcription and mRNA Stability in the Synergistic Interaction Between NKSF and IL-2," J. Immunol., 148:92-98.

(56) References Cited

OTHER PUBLICATIONS

Chaudhary et al., (1988), "Selective Killing of HIV-Infected Cells by Recombinant Human CD4-Pseudomonas Exotoxin Hybrid Protein," Nature, 335:370-372.
Chaudhary et al., (1989), "A Recombinant Immunotoxin Consisting of Two Antibody Variable Domains Fused to Pseudomonas Exotoxin," Nature, 339:394-397.
Cheon et al., (1994), "High-Affinity Binding Sites for Related Fibro-blast Growth Factor Ligands Reside Within Different Receptor Immunoglobulin-Like Domains," Proc. Natl. Acad. Sci. USA, 91:989-993.
Cirulli et al., (1998), "KSA Antigen Ep-CAM Mediates Cell-Cell Adhesion of Pancreatic Epithelial Cells: Morphoregulatory Roles in Pancreatic Islet Development," J. Cell Biol., 140:1519-34.
Cohen et al., (1998), "An Artificial Cell-Cycle Inhibitor Isolated from a Combinatorial Library," Proc. Natl. Acad. Sci. USA, 95:14272-7.
Colman et al. (1994), "Effects of Amino Acid Sequence Changes on Antibody-Antigen Interactions," Res. Immunol., 145:33-36.
Griffin et al., (1983), "Characterization of an Antigen Expressed by Human Natural Killer Cells," J. Immunol., 130(6):2947-51.
Grimaldi et al., (1989), "The t(5;14) Chromosomal Translocation in a Case of Acute Lymphocytic Leukemia Joins the lnterleukin-3 Gene to the Immunoglobulin Heavy Chain Gene," Blood, 73(8):2081-2085.
Gurewich et al., (1988), "Characterization of the Intrinsic Fibrinolytic Properties of Pro-Urokinase Through a Study of Plasmin-Resistant Mutant Forms Produced by Site-Specific Mutagenesis of Lysine," J. Clin. Invest., 82:1956-1962.
Guyre et al., (1997), "Increased Potency of Fc-Receptor-Targeted Antigens," Cancer Immunol. Immunother., 45:146-148.
Halin et al., (2002), "Enhancement of the Antitumor Activity of Interleukin-12 by Targeted Delivery to Neovasculature," Nature Biotechnology, 20:264-269.
Handgretinger et al., (1995), "A Phase I Study of Human/Mouse Chimeric Anti-Ganglioside GD2 Antibody ch14.18 in Patients with Neuroblastoma," European J. Cancer, 31A(2): 261-267.
Hank et al., (1996), "Activation of Human Effector Cells by a Tumor Reactive Recombinant Anti-Ganglioside GD2 lnterleukin-2 Fusion Protein (ch14.18-IL2)," Clin Cancer Research, 2(12): 1951-1959.
Hank et al., (2003), "Determination of Peak Serum Levels and Immune Response to the Humanized Anti-Ganglioside Antibody-Interleukin-2 Immunocytokine," in Methods in Molecular Medicine, 85: Novel Anticancer Drug Protocols, Buolamwini et al., (eds.), pp. 123-131, Humana Press Inc., Totowana, NJ.
Haraguchi, (1994), "Isolation of GD3 Synthase Gene by Expression Cloning of GM3 ci-2,8-sialyltransferase cDNA Using Anti-GD2 Monoclonal Antibody," Proc. Natl. Acad. Sci. USA, 91(22):10455-10459.
Harris et al., (1993), "Therapeutic Antibodies—the Coming of Age," Trends in Biotechnology, 11:42-44.
Harris, (1995), "Processing of C-Terminal Lysine and Arginine Residues of Proteins Isolated from Mammalian Cell Culture," J. Chromatography A, 705:129-134.
Harvill et al., (1995), "An IgG3-IL2 Fusion Protein Activates Complement, Binds FcγRI, Generates LAK Activity and Shows Enhanced Binding to the High Affinity IL-2R," Immunotechnology, 1:95-105.
Harvill et al., (1996), "In Vivo Properties of an IgG3-IL-2 Fusion Protein: A General Strategy for Immune Potentiation," J. Immunology, 157(7):3165-3170.
He et al., (1998), "Humanization and Pharmacokinetics of a Monoclonal Antibody with Specificity for Both E- and P-Selectin,"J. Immunology, 160:1029-1035.
Hellstrom et al., (1986), "Antitumor Effects of L6, an IgG2a Anti-body that Reacts with Most Human Carcinomas," Proc. Natl. Acad. Sci. USA, 83: 7059-7063.
Henkart, (1985), "Mechanism of Lymphocyte-Mediated Cytotoxicity," Ann. Rev. Immunol, 3:31-58.

Herrmann et al., (1989), "Hematopoietic Responses With Advanced Malignancy Treated With Recombinant Human Granulocyte-Macrophage Colony-Stimulating Factor," Journal of Clinical Oncology, 7(2): 159-167.
Hezareh et al., (2001), "Effector Function Activities of a Panel of Mutants of a Broadly Neutralizing Antibody against Human Immunodeficiency Virus Type 1" J. Virology, 75(24):12161-12168.
Holden et al., (2001), "Augmentation of Antitumor Activity of an Antibody-Interleukin 2 Immunocytokine with Chemotherapeutic Agents," Clinical Cancer Research, 7:2862-2869.
Holden et al., (2001), "Augmentation of Anti-Tumor Activity of KS-IL2 Immunocytokine with Chemotherapeutic Agents," Proceedings of the American Association for Cancer Research, 42:683, Abstract No. 3675 (XP-002195344).
Hornick et al., (1999), "Pretreatment with a Monoclonal Antibody/Interleukin-2 Fusion Protein Directed Against DNA Enhances the Delivery of Therapeutic Molecules to Solid Tumors," Clin. Cancer Research, 5:51-60.
Hum et al., (1980), "Production of Reagent Antibodies," Methods in Enzymology, 70:104-142.
Connor et al., (2004), "Ex vivo Evaluation of Anti-EpCAM Immunocytokine huKS-IL2 In Ovarian Cancer," J. Immunotherapy, 27:211-219.
Couto et al., (1994) "Humanization of KC4G3, an Anti-Human Carcinoma Antibody," Hybridoma, 3:215-219.
Cruse et al., (eds.), (1995), Illustrated Dictionary of Immunology, pp. 156-158, CRC Press, NY.
Database Uniprot, (Jul. 21, 1986), Database Accession No. P01859.
Davis et al., (2003), "Immunocytokines: Amplification of Anti-Cancer Immunity," Cancer Immunol. Immunother, 52:297-308.
Dolman et al., (1998), "Suppression of Human Prostate Carcinoma Metastases in Severe Combined Immunodeficient Mice by Interleukin 2 Immunocytokine Therapy," Clin. Cancer Research., 4(10):2551-2557.
Fell et al., (1991), "Genetic Construction and Characterization of a Fusion Protein Consisting of a Chimeric F(ab') with Specificity for Carcinomas and Human IL-2," J. Immunology, 146(7):2446-2452.
Fell et al., (1992), "Chimeric L6 Anti-Tumor Antibody: Genomic Construction, Expression, and Characterization of the Antigen Binding Site," J. Biological Chemistry, 267:15552-15558.
Frost et al., (1997), "A Phase FIB Trial of Murine Monoclonal Anti-GD2 Antibody 14.G2a Plus Interleukin-2 in Children with Refractory Neuroblastoma," Cancer, 80(2):317-333.
Gan et al., (1999), "Specific Enzyme-Linked Immunosorbent Assays for Quantitation of Antibody-Cytokine Fusion Proteins," Clinical and Diagnostic Laboratory Immunology, 6(2):236-42.
Gasson et al., (1984), "Purified Human Granulocyte Macrophage Colony-Stimulating Factor: Direct Action on Neutrophils," Science, 226:1339-1342.
Gillies et al., (1989), "Expression of Human Anti-Tetanus Toxoid Antibody in Transfected Murine Myeloma Cells," Bio/Technology, 7:799-804.
Gillies et al., (1989), "High-Level Expression of Chimeric Antibodies Using Adapted cDNA Variable Region Cassettes," J. Immunol. Methods, 125:191-202.
Gillies et al., (1990), "Antigen Binding and Biological Activities of Engineered Mutant Chimeric Antibodies with Human Tumor Specificities," Hum. Antibod. Hybridomas, 1(1):47-54.
Gillies et al., (1991), "Expression of Genetically Engineered Immunoconjugates of Lymphotoxin and a Chimeric Anti-Ganglioside GD2 Antibody," Hybridoma., 10(3):347-56.
Ganglioside GD2 Antibody, Hybridoma., 10(3):347-56.
Gillies et al., (1992), "Antibody-Targeted Interleukin 2 Stimulates T-Cell Killing of Autologous Tumor Cells," Proc. Natl. Acad. Sci. USA, 89:1428-1432.
Gillies et al., (1993), "Biological Activity and In Vivo Clearance of Antitumor Antibody/Cytokine Fusion Proteins," Bioconjugate Chem., 4(3):230-235.
Gillies et al., (1998), "Antibody-IL-12 Fusion Proteins are Effective in SCID Mouse Models of Prostate and Colon Carcinoma Metastases," J. Immunology, 160:6195-6203.

(56) References Cited

OTHER PUBLICATIONS

Gillies et al., (1999), "Improving the Efficacy of Antibody-Interleukin 2 Fusion Proteins by Reducing Their Interaction with Fc Receptors," Cancer Research, 59:2159-2166.

Gillies et al., (2002), "Bi-Functional Cytokine Fusion Proteins for Gene Therapy and Antibody-Targeted Treatment of Cancer," Cancer Immunol. Immunother., 51(8):449-60.

Gillies et al., (2002), "Improved Circulating Half-Life and Efficacy of an Antibody-Interleukin 2 Immunocytokine Based on Reduced Intracellular Proteolysis," Clin. Cancer Research, 8(1):210-216.

Goeddel et al., (1986), "Tumor Necrosis Factors: Gene Structure and Biological Activities," Cold Spring Harb. Symp. Quant. Biol, 51:597-609.

Gren et al., (1983), "A New Type of Leukocytic Interferon," English Translation of Dokl. A kad. Nauk. SSSR., 269(4):986-990.

Becker et al., (1996), "An Antibody-Interleukin 2 Fusion Protein Overcomes Tumor Heterogeneity by Induction of a Cellular Immune Response," Proc. Natl. Acad. Sci. USA, 93:7826-7831.

Becker et al., (1996), "Eradication of Human Hepatic and Pulmonary Melanoma Metastases in SCID Mice by Antibody-Interleukin 2 Fusion Proteins," Proc. Natl. Acad. Sci. USA, 93:2702-2707.

Becker et al., (1996), "Long-Lived and Transferable Tumor Immunity in Mice after Targeted lnterleukin-2 Therapy," 1 Clin. Invest. 98(12):2801-2804.

Becker et al., (1996), "T Cell-Mediated Eradication of Murine Metastatic Melanoma Induced by Targeted lnterleukin-2 Therapy," J. Exp. Med., 183(50):2361-2366.

Beutler et al., (1988), "Tumor Necrosis, Cachexia, Shock, and Inflammation: A Common Mediator," Annual Rev. Biochem., 57:505-518.

Bitonti et al. (2004), "Pulmonary Delivery of an Erythropoietin Fc Fusion Protein in Non-Human Primates Through an Immunoglobulin Transport Pathway," Proc. Natl. Acad. Sci. USA, 101(26):9763-9768.

Gillies et al., (1991), "Targeting Human Cytotoxic T Lymphocytes to Kill Heterologous Epidermal Growth Factor Receptor-Bearing Tumor Cells: Tumor-Infiltrating Lymphocyte/Hormone Receptor/Recombinant Antibody," J. Immunology, 146(3):1067-1071.

Bjorn et al., (1985), "Evaluation of Monoclonal Antibodies for the Development of Breast Cancer Immunotoxins," Cancer Research, 45:1214-1221.

Boulianne et al., (1984), "Production of Functional Chimaeric Mouse/Human Antibody," Nature, 312:643-6.

Bubenik et al., (1995), "lnterleukin-2 Gene Therapy of Residual EL-4 Leukaemia Potentiates the Effect of Cyclophosphamide Pretreatment," J. Cancer Res. Clin. Oncol., 121:39-43.

Huston et al., (1988), "Protein Engineering of Antibody Binding Sites: Recovery of Specific Activity in an Anti-Digoxin Single-Chain Fv Analogue Produced in *Escherichia colt*," Proc. Natl. Acad. Sci. USA, 85:5879-5883.

Imboden et al., (2001), "The Level of MHC Class I Expression on Murine Adenocarcinoma Can Change the Antitumor Effector Mechanism of Immunocytokine Therapy," Cancer Research, 61(4): 1500-1507.

Jefferis et al., (1998), "IgG-Fc-Mediated Effector Functions: Molecular Definition of Interaction Sites for Effector Ligands and the Role of Glycosylation," Immunological Reviews, 163:59-76.

Jones et al., (1986), "Replacing the Complementarity-Determining Regions in a Human Antibody with Those from a Mouse," Nature, 321:522-525.

Jones et al., (2004), "The Development of a Modified Human IFN-Alpha2b Linked to the Fc Portion of Human IgG1 as a Novel Potential Therapeutic for the Treatment of Hepatitis C Virus Infection," J. Interferon Cytokine Res., 24(9):560-72.

Jung et al., (1986), "Activation of Human Peripheral Blood Mononuclear Cells by Anti-T3: Killing of TumorTarget Cells Coated with Anti-Target-Anti-T3 Conjugates," Proc. Natl. Acad. Sci. USA, 83:4479-4483.

Kappel et al., (1992), "Regulating Gene Expression in Transgenic Animals," Current Opinion in Biotechnology, 3:548-553.

Kendra et al., (1999), "Pharmacokinetics and Stability of the ch14.18-Interleukin-2 Fusion Protein in Mice," Cancer Immunol. Immunother, 48:219-229.

Kim et al., (1999), "Cytokine Molecular Adjuvants Modulate Immune Responses Induced by DNA Vaccine Constructs for HIV-1 and SIV," Journal of Interferon and Cytokine Research, 19:77-84.

Kranz et al., (1984), "Attachment of an Anti-Receptor Antibody to Non-Target Cells Renders Them Susceptible to Lysis by a Clone of Cytotoxic T Lymphocytes," Proc. Natl. Acad. Sci. USA, 81:7922-7926.

Kushner et al., (2001), "Phase II Trial of the Anti-GD2 Monoclonal Antibody 3F8 and Granulocyte-Macrophage Colony-Stimulating Factor for Neuroblastoma," J. Clinical Oncology, 19(22):4189-94.

Lanza et al., (1993), "Active Immunity against the CD4 Receptor by Using an Antibody Antigenized with Residues 41-55 of the First Extracellular Domain," Proc. Natl. Acad. Sci. USA, 90:11683-7.

Lazar et al., (1988), "Transforming Growth Factor a: Mutation of Aspartic Acid 47 and Leucine 48 Results in Different Biological Activities," Molecular and Cellular Biology, 8(3):1247-1252.

Lifely et al., (1995), "Glycosylation and Biological Activity of CAMPATH-1H Expressed in Different Cell Lines and Grown Under Different Culture Conditions," Glycobiology, 5(8):813-22.

Liu et al., (1985), "Heteroantibody Duplexes Target Cells for Lysis by Cytotoxic T Lymphocytes," Proc. Natl. Acad. Sci. USA, 82:8648-8652.

Lo et al., (1998), "High Level Expression and Secretion of Fc-X Fusion Proteins in Mammalian Cells," Protein Engineering, 11(6):495-500.

Lund et al., (1993), "Control of IgG/Fc Glycosylation: A Comparison of Oligosaccharides from Chimeric Human/Mouse and Mouse Subclass Immunoglobulin Gs," Mol. Immunol., 30(8):741-748.

Maloney et al., (1994), "Phase I Clinical Trial Using Escalating Single-Dose Infusion of Chimeric Anti-CD20 Monoclonal Antibody (IDEC-C2B8) in Patients with Recurrent B-Cell Lymphoma," Blood, 84(8):2457-2466.

Mariani et al., (1997), "Tumor Targeting Potential of the Monoclonal Antibody BC-1 against Oncofetal Fibronectin in Nude Mice Bearing Human Tumor Implants," Cancer, 80:2378-84.

Marti-Renom et al., (2000), "Comparative Protein Structure Modeling of Genes and Genomes," Annu. Rev. Biophys. Biomol. Struct., 29:291-325.

MacLean et al., (1996), "Enhancing the Effect of Theratope STn-KLH Cancer Vaccine in Patients with Metastatic Breast Cancer by Pretreatment with Low-Dose Intravenous Cyclophosphamide," J. Immunother, 19(4):309-316.

Mateo et al., (2000), "Removal of Amphipathic Epitopes from Genetically Engineered Antibodies: Production of Modified Immunoglobulins with Reduced Immunogenicity," Hybridoma, 19(6):463-471.

McMahan et al., (1991), "A Novel IL-1 Receptor, Cloned From B-Cells by Mammalian Expression is Expressed in Many Cell Types," EMBO J., 10:2821-32.

Menard et al., (1983), "Generation of Monoclonal Antibodies Reacting with Normal and Cancer Cells of Human Breast," Cancer Res., 43:1295-300.

Michaelsen et al., (1977), "Primary Structure of the Hinge Region of Human IgG3," J. Biol. Chem., 252(3):883-889.

Miyake et al., (1988), "Synthesis of Recombinant Human Single-Chain Urokinase-Type Plasminogen Activator Variants Resistant to Plasmin and Thrombin," J. Biochem., 104:643-647.

Mueller et al., (1990), "Enhancement of Antibody-Dependent Cytotoxicity With A Chimeric Anti-GD2 Antibody," J. Immunology, 144 (4): 1382-1386.

Mueller et al., (1990), "Serum Half-Life and Tumor Localization of a Chimeric Antibody Deleted of the CH2 Domain and Directed Against the Disialoganglioside GD2," Proc. Natl. Acad. Sci. USA., 87:5702-5705.

Mueller et al., (1997), "Humanized Porcine VCAM-Specific Monoclonal Antibodies with Chimeric IgG2/G4 Constant Regions Block Human Leukocyte Binding to Porcine Endothelial Cells," Molecular Immunology, 34(6)441-452.

(56) References Cited

OTHER PUBLICATIONS

Murphy et al., (1986), "Genetic Construction, Expression, and Melanoma-Selective Cytotoxicity of a Diphtheria Toxin-Related a-Melanocyte-Stimulating Hormone Fusion Protein," Proc. Natl. Acad. Sci. USA, 83:8258-8262.
Murphy, (1988), "Diphtheria-Related Peptide Hormone Gene Fusions: A Molecular Gene Approach to ChimericToxin Development," in Immunotoxins, pp. 123-140, Frankel (ed.), Kluwer Acad. Pub.
Naramura et al., (1993), "Therapeutic Potential of Chimeric and Murine Anti-(Epidermal Growth Factor Receptor) Antibodies in a Metastasis Model for Human Melanoma," Cancer Immuno. Immunother., 37:343-349.
Nastala et al., (1994), "Recombinant IL-12 Administration Induces Tumor Regression in Association with IFN-y Production," J. Immunol., 153:1697-706.
Neal et al., (2003), "NXS2 Murine Neuroblastomas Express Increased Levels of MHC Class I Antigens upon Recurrence Following NK-Dependent Immunotherapy," Cancer Immunol. Immunother, 53:41-52.
Neal et al., (2004), "Enhanced Activity of Hu14.18-IL2 Immunocytokine against Murine NXS2 Neuroblastoma when Combined with Interleukin-2 Therapy," Clin. Cancer. Res., 10:4839-4847.
Nedwin et al., (1985), "Human Lymphotoxin and Tumor Necrosis Factor Genes: Structure, Homology and Chromosomal Localization," Nucleic Acids Research, 13(17):6361-6373.
Nelles et al., (1987), "Characterization of Recombinant Human Single Chain Urokinase-Type Plaminogen Activtor Mutants Produced by Site-Specific Mutagenesis of Lysine 158," J. Biol. Chem., 262(12):5682-5689.
Niwa et al., (2005), "Enhanced Natural Killer Cell Binding and Activation by Low-Fucose IgG1 Antibody Results in Potent Antibody-Dependent Cellular Cytotoxicity Induction at Lower Antigen Density," Clin. Cancer Res., 11(6):2327-36.
Orlandi et al., (1989), "Cloning Immunoglobulin Variable Domains for Expression by the Polymerase Chain Reaction," Proc. Natl. Acad. Sci. USA, 86:3833-7.
Padlan et al., (1991), "A Possible Procedure for Reducing the Immunogenicity of Antibody Variable Domains while Preserving Their Ligand Binding Properties," Mol. Immunol., 28:489-498.
Paul et al., (1988), "Lymphotoxin," Ann. Rev. Immunol., 6:407-438. Perez et al., (1989), "Isolation and Characterization of a cDNA Encoding the KS1/4 Epithelial Carcinoma Marker," J. Immunology, 142(10):3662-3667.
Queen et al., (1989), "A Humanized Antibody that Binds to the Interleukin 2 Receptor," Proc. Natl. Acad. Sci. USA, 86:10029-33.
Pastan et al., (1989), "Pseudomonas Exotoxin: Chimeric Toxins," Journal of Biological Chemistry, 264(26): 15157-15160.
Ravetch, (1997), "Fc Receptors," Cure. Opin. Immunol., 9:121-125.
Reisfeld et al., (1994), "Potential of Genetically Engineered Anti-Ganglioside GD2 Antibodies for Cancer Immunotherapy," Prog. Brain Res., 101:201-212.
Riechmann et al., (1988), "Reshaping Human Antibodies for Therapy," Nature, 332:323-7.
Riethmuller et al., (1994), "Randomised Trial of Monoclonal Antibody for Adjuvant Therapy of Resected Dukes' C Colorectal Carcinoma," The Lancet, 343:1177-1183.
Robinson et al., (1998), "Optimizing the Stability of Single-Chain Proteins by Linker Length and Composition Mutagenesis," Proc. Natl. Acad. Sci. USA, 95:5929-34.
Roguska et al., (1994), "Humanization of Murine Monoclonal Antibodies Through Variable Domain Resurfacing," Proc. Nat'l. Acad. Sci. USA., 91(3):969-73.
Saleh et al., (1992), "Phase I Trial of the Chimeric Anti-GD2 Monoclonal Antibody ch14.18 in Patients With Malignant Melanoma," Hum. Antiob. Hybridomas, 3:19-24.
Santon et al., (1986), "Effects of Epidermal Growth Factor Receptor Concentration on Tumorigenicity of A431 Cells in Nude Mice," Cancer Research, 46:4701-4705.

Schlom (1991), "Monoclonal Antibodies: They're More and Less Than You Think," in Molecular Foundations of Oncology, pp. 95-133.
Schwartzberg et al., (2001), "Clinical Experience with Edrecolomab: A Monoclonal Antibody Therapy for Colon Carcinoma," Critical Reviews in Oncology/Hematology, 40:17-24.
Sharma et al., (1999), "T cell-Derived IL-10 Promotes Lung Cancer Growth by Suppressing Both T cell and APC Function," Journal of Immunology, 163:5020-5028.
Sharp et al., (1988), "Codon Usage Patterns in *Escherichia coli*, Bacillus subtilis, *Saccharomyces cerevisiae, Schizosaccharomyces pombe, Drosophila melanogaster* and *Homo sapiens*; a Review of the Considerable Within-Species Diversity," Nucleic Acids Res., 16(17):8207-8211.
Shen et al., (1986), "Heteroantibody-Mediated Cytotoxicity: Antibody to the High Affinity Fc Receptor for IgG Mediates Cytotoxicity by Human Monocytes that is Enhanced by Interferon-y and is Not Blocked by Human IgG," J. Immunology, 137(11):3378-3382.
Shields et al., (2002), "Lack of Fucose on Human IgG1 N-linked Oligosaccharide Improves Binding to Human Fegamma Rill and Antibody-Dependent Cellular Toxicity," J. Biol. Chem., 277(30):26733-40.
Shinkawa et al., (2003), "The Absence of Fucose but not the Presence of Galactose or Bisecting N-Acetylglucosamine of Human IgG1 Complex-Type Oligosaccharides Shows the Critical Role of Enhancing Antibody-Dependent Cellular Cytotoxicity," J. Biol. Chem., 278(5):3466-73.
Sturniolo et al., "Generation of Tissue-Specific and Promiscuous HLA Ligand Databases Using DNA Microarrays and Virtual HLA Class II Matrices," Nat. Biotechnol., 17(6):555-61.
Tao et al., (1991), "The Differential Ability of Human IgG1 and IgG4 to Activate Complement Is Determined by the COOH-terminal Sequence of the CH2 Domain," J. Exp. Med., 173:1025-1028.
The Merck Manual of Diagnosis and Therapy, 17th Ed., (1999) pp. 990-993 and 1278-1283.
Tiruppathi et al., (1996), "Isolation and Characterization of a Cell Surface Albumin-Binding Protein from Vascular Endothelial Cells," Proc. Nat. Acad. Sci. USA, 93:250-4.
Vagliani et al., (1996), "Interleukin 12 Potentiates the Curative Effect of a Vaccine Based on Interleukin 2-Transduced Tumor Cells," Cancer Research, 56:467-470.
Varki et al., (1984), "Antigens Associated with a Human Lung Adenocarcinoma Defined by Monoclonal Antibodies," Cancer Research, 44:681-687.
Vitetta et al., (1987), "Redesigning Nature's Poisons to Create Anti-Tumor Reagents," Science, 238:10981104.
Voest et al., (1995), "Inhibition of Angiogenesis in Vivo by Interleukin 12," J. Natl. Cane. Inst., 87:581-6.
Weber et al., (2001), "Phase I Trial of huKS-IL2 Immunocytokine in Patients with Prostate Carcinoma: Clinical, PK, and Biological PD Results (Abstract)," American Society of Clinical Oncology Pro-gram/Proceedings, 20(Part 1):259a.
Weitkamp et al., (1973), "Additional Data on the Population Distribution of Human Serum Albumin Genes; Three New Variants," Ann. Hum. Genet., 37:219-26.
Wells, (1990), "Additivity of Mutational Effect in Proteins," Biochemistry, 29(37):8509-8517.
Went et al., (2004), "Frequent EpCam Protein Expression in Human Carcinomas," Human Pathology, 35(1):122-128.
Wysocka et al., (1995), "Interleukin-12 is Required for Interferon-y Production and Lethality in Lipopolysaccharide-Induced Shock in Mice," Fur. J. Immunol., 25:672-6.
Yan et al., (1996), "Characterization of an Ig VH Idiotopethat Results in Specific Homophilic Binding and Increased Avidity for Antigen," J. Immunol., 157:1582-8.
Yeh et al., (1992), "Design of Yeast-Secreted Albumin Derivatives for Human Therapy: Biological and Antiviral Properties of a Serum Albumin-CD4 Genetic Conjugate," Proc. Natl. Acad.Sci. USA, 89:1904-8.
Yokota et al., (1986), "Isolation and Characterization of a Human Interleukin cDNA Clone, Homologous to Mouse B-Cell Stimula-

(56) References Cited

OTHER PUBLICATIONS tory Factor 1, that Expresses B-Cell- and T-Cell-Stimulating Activities," Proc. Natl. Acad. Sci. USA, 83:5894-5898.

Yu et al., (1998), "Phase I Trial of a Human-Mouse Chimeric Anti-Disaloganglioside Monoclonal Antibody ch14.18 in Patients with Refractory Neuroblastoma and Osteosarcoma," J. Clinical Oncology, 16(6):2169-80.

International Search Report for International Application No. PCT/EP2006/012365, dated Apr. 18, 2007 (5 pages).

Written Opinion for International Application No. PCT/EP2006/012365, dated Apr. 18, 2007 (7 pages).

Roguska et al., (1996), "A Comparison of Two Murine Monoclonal Antibodies Humanized by CDR-Grafting and Variable Domain Resurfacing," Protein Engineering, 9(10):895-904.

Weiner et al., (1984), "A New Force Field for Molecular Mechanical Simulation of Nucleic Acids and Proteins," J. Am. Chem. Soc., 106:765-784.

Yazawa et al., (2005), "Immunotherapy Using Unconjugated CD19 Monoclonal Antibodies in Animal Models for B Lymphocyte Malignancies and Autoimmune Disease," Proc. Natl. Acad. Sci. USA, 102(42): 15178-15183.

Roque-Navarro et al., (2003) "Humanization of predicted T-cell epitopes reduces the immunogenicity of chimeric antibodies: New evidence supporting a simple method," Hybrid Hybridomics, vol. 22, No. 4, pp. 245-257.

Singh and Raghava, (2001), "ProPed: prediction of HLA-DR binding sites," Bioinformatics, vol. 17, 1236-1237.

Liu et al., (1996), "Cure of multidrug-resistant human B-cell lymphoma xenografts by combinations of anti-B4-blocked ricin and chemotherapeutic drugs", Blood, vol. 87, No. 9, 3892-3898.

Griffin et al., (1983), "Characterization of an antigen expressed by human natural killer cells," J. Immunol., vol. 130, 2947-2951.

Yacoub-Youssef et al., (2005), "Engraftment of human T, B and NK cells in CB.17 SCID/beige mice by transfer of human spleen cells," Transpl. Immunol., vol. 15, 157-164.

\* cited by examiner

Figure 1: Nucleic acid sequence encoding B4 antibody heavy chain variable region (B4 VH0)
CAGGTGCAACTGCAGCAGCCTGGGGCTGAAGTGGTGAAGCCTGGGGCTTCAGTGAGACT
GTCCTGCAAGACTTCTGGCTACACCTTCACCAGCAACTGGATGCACTGGGTGAAGCAGA
GGCCTGGACAAGGCCTTGAGTGGATCGGAGAGATTGATCCTTCTGATAGTTATACTAAC
TACAATCAAAAGTTCAAGGGCAAGGCCAAGTTGACTGTAGACAAATCCTCCAGCACAGC
CTACATGGAAGTCAGCAGCCTGACATCTGAGGACTCTGCGGTCTATTACTGTGCAAGAG
GTAGCAACCCTTACTACTATGCTATGGACTACTGGGGTCAAGGAACCTCAGTCACCGTC
TCCTCA(SEQ ID NO:1)

Figure 2: Nucleic acid sequence encoding B4 antibody heavy chain variable region with codons for amino acid substitutions K23E, G42D, K69E, and S85D (B4 VHv1)
CAGGTGCAACTGCAGCAGCCTGGGGCTGAAGTGGTGAAGCCTGGGGCTTCAGTGAGACT
GTCCTGCGAGACTTCTGGCTACACCTTCACCAGCAACTGGATGCACTGGGTGAAGCAGA
GGCCTGACCAAGGACTTGAGTGGATCGGAGAGATTGATCCTTCTGATAGTTATACTAAC
TACAATCAAAAGTTCAAGGGCAAGGCCGAATTGACTGTAGACAAATCCTCCAGCACAGC
CTACATGGAAGTCAGCGACCTGACATCTGAGGACTCTGCGGTCTATTACTGTGCAAGAG
GTAGCAACCCTTACTACTATGCTATGGACTACTGGGGTCAAGGAACCTCAGTCACCGTC
TCCTCA(SEQ ID NO:2)

Figure 3: Nucleic acid sequence encoding B4 antibody heavy chain variable region with codons for amino acid substitutions K69E, and S85D (B4 VHv2)
CAGGTGCAACTGCAGCAGCCTGGGGCTGAAGTGGTGAAGCCTGGGGCTTCAGTGAGACT
GTCCTGCAAGACTTCTGGCTACACCTTCACCAGCAACTGGATGCACTGGGTGAAGCAGA
GACCTGGACAAGGACTTGAGTGGATCGGAGAGATTGATCCTTCTGATAGTTATACTAAC
TACAATCAAAAGTTCAAGGGCAAGGCCGAATTGACTGTAGACAAATCCTCCAGCACAGC
CTACATGGAAGTCAGCGACCTGACATCTGAGGACTCTGCGGTCTATTACTGTGCAAGAG
GTAGCAACCCTTACTACTATGCTATGGACTACTGGGGTCAAGGAACCTCAGTCACCGTC
TCCTCA(SEQ ID NO:3)

Figure 4: Nucleic acid sequence encoding B4 antibody heavy chain variable region with codons for amino acid substitutions Q5E, V12K, R19K, L20V, T24A, S85D, and S88A (B4 VHv3)
CAGGTGCAACTGGAGCAGCCTGGGGCTGAAGTGAAGAAGCCTGGGGCTTCAGTGAAGGT
GTCCTGCAAGGCTTCTGGCTACACCTTCACCAGCAACTGGATGCACTGGGTGAAGCAGA
GGCCTGGACAAGGACTTGAGTGGATCGGAGAGATTGATCCTTCTGATAGTTATACTAAC
TACAATCAAAAGTTCAAGGGCAAGGCCAAGTTGACTGTAGACAAATCCTCCAGCACAGC
CTACATGGAAGTCAGCGACCTGACAGCTGAGGACTCTGCGGTCTATTACTGTGCAAGAG
GTAGCAACCCTTACTACTATGCTATGGACTACTGGGGTCAAGGAACCTCAGTCACCGTC
TCCTCA(SEQ ID NO:4)

Figure 5: Nucleic acid sequence encoding B4 antibody heavy chain variable region with codons for amino acid substitutions Q5E, R19K, L20V, R40T, Q43K, K65D, S85D, S88A, and V93T (B4 VHv4)
CAGGTGCAACTGGAGCAGCCTGGGGCTGAAGTGGTGAAGCCTGGGGCTTCAGTGAAGGT
GTCCTGCAAGACTTCTGGCTACACCTTCACCAGCAACTGGATGCACTGGGTGAAGCAGA
CGCCTGGAAAAGGACTTGAGTGGATCGGAGAGATTGATCCTTCTGATAGTTATACTAAC
TACAATCAAAAGTTCGATGGCAAGGCCAAGTTGACTGTAGACAAATCCTCCAGCACAGC
CTACATGGAAGTCAGCGACCTGACAGCTGAGGACTCTGCGACCTATTACTGTGCAAGAG
GTAGCAACCCTTACTACTATGCTATGGACTACTGGGGTCAAGGAACCTCAGTCACCGTC
TCCTCA(SEQ ID NO:5)

Figure 6: Nucleic acid sequence encoding B4 antibody heavy chain variable region with codons for amino acid substitutions Q5E, V12K, R19K, L20V, T24A, K38R, R40A, Q43K, K65D, S85D, and V93T (B4 VHv5)
CAGGTGCAACTGGAGCAGCCTGGGGCTGAAGTGAAGAAGCCTGGGGCTTCAGTGAAGGT
GTCCTGCAAGGCTTCTGGCTACACCTTCACCAGCAACTGGATGCACTGGGTGAGACAGG
CACCTGGAAAAGGACTTGAGTGGATCGGAGAGATTGATCCTTCTGATAGTTATACTAAC
TACAATCAAAAGTTCGATGGCAAGGCCAAGTTGACTGTAGACAAATCCTCCAGCACAGC
CTACATGGAAGTCAGCGACCTGACATCTGAGGACTCTGCGACCTATTACTGTGCAAGAG
GTAGCAACCCTTACTACTATGCTATGGACTACTGGGGTCAAGGAACCTCAGTCACCGTC
TCCTCA(SEQ ID NO:6)

Figure 7: Nucleic acid sequence encoding B4 antibody heavy chain variable region with codons for amino acid substitutions Q5E, R19K, L20V, K65D, S85D, and V93T (B4 VHv6)
CAGGTGCAACTGGAGCAGCCTGGGGCTGAAGTGGTGAAGCCTGGGGCTTCAGTGAAGGT
GTCCTGCAAGACTTCTGGCTACACCTTCACCAGCAACTGGATGCACTGGGTGAAGCAGA
GGCCTGGACAAGGACTTGAGTGGATCGGAGAGATTGATCCTTCTGATAGTTATACTAAC
TACAATCAAAAGTTCGATGGCAAGGCCAAGTTGACTGTAGACAAATCCTCCAGCACAGC
CTACATGGAAGTCAGCGACCTGACATCTGAGGACTCTGCGACCTATTACTGTGCAAGAG
GTAGCAACCCTTACTACTATGCTATGGACTACTGGGGTCAAGGAACCTCAGTCACCGTC
TCCTCA(SEQ ID NO:7)

Figure 8: Nucleic acid sequence encoding B4 antibody light chain variable region (B4 VK0)
CAAATTGTTCTCACCCAGTCTCCAGCAATCATGTCTGCATCTCCAGGGGAGAAGGTCAC
CATGACCTGCAGTGCCAGCTCAGGTGTCAACTACATGCACTGGTACCAGCAGAAGCCAG
GCACCTCCCCCAAAAGATGGATTTATGACACATCCAAACTGGCTTCTGGAGTCCCTGCT
CGCTTCAGTGGCAGTGGGTCTGGGACCTCTTATTCTCTCACAATCAGCAGCATGGAGGC
TGAAGATGCTGCCACTTATTACTGCCATCAGCGAGGTAGTTACACGTTCGGAGGGGGGA
CCAAGCTGGAAATAAAA(SEQ ID NO:8)

Figure 9: Nucleic acid sequence encoding B4 antibody light chain variable region with codons for amino acid substitutions V3A, S7E, and A54D (B4 VKv1)
CAAATTGCTCTCACCCAGGAGCCAGCAATCATGTCTGCATCTCCAGGGGAGAAGGTCAC
CATGACCTGCAGTGCCAGCTCAGGTGTCAACTACATGCACTGGTATCAGCAGAAGCCAG
GCACCTCCCCCAAAAGATGGATTTATGACACATCCAAACTGGATTCTGGAGTCCCTGCT
CGCTTCAGTGGCAGTGGGTCTGGGACCTCTTATTCTCTCACAATCAGCAGCATGGAGGC
TGAAGATGCTGCCACTTATTACTGCCATCAGCGAGGTAGTTACACGTTCGGAGGGGGA
CCAAGCTGGAAATAAAA(SEQ ID NO:9)

Figure 10: Nucleic acid sequence encoding B4 antibody light chain variable region with codons for amino acid substitutions Q1D, I10T, M11L, and A54D (B4 VKv2)
GACATTGTTCTCACCCAGTCTCCAGCAACTTTGTCTGCATCTCCAGGGGAGAAGGTCAC
CATGACCTGTAGTGCCAGCTCAGGTGTCAACTACATGCACTGGTATCAGCAGAAGCCAG
GCACCTCCCCCAAAAGATGGATTTATGACACATCCAAACTGGATTCTGGAGTCCCTGCT
CGCTTCAGTGGCAGTGGGTCTGGGACCTCTTATTCTCTCACAATCAGCAGCATGGAGGC
TGAAGATGCTGCCACTTATTACTGCCATCAGCGAGGTAGTTACACGTTCGGAGGGGGA
CCAAGCTGGAAATAAAA(SEQ ID NO:10)

Figure 11: Nucleic acid sequence encoding B4 antibody light chain variable region with codons for amino acid substitutions I10T, M11L, V19A, V29A, and S75E (B4 VKv3)
CAAATTGTTCTCACCCAGTCTCCAGCAACTTTGTCTGCATCTCCAGGGGAGAAGGCTAC
CATGACCTGCAGTGCCAGCTCAGGTGCTAACTACATGCACTGGTACCAGCAGAAGCCAG
GCACCTCCCCCAAAAGATGGATTTATGACACATCCAAACTGGCTTCTGGAGTCCCTGCT
CGCTTCAGTGGCAGTGGGTCTGGGACCTCTTATTCTCTCACAATCGAGAGCATGGAGGC
TGAAGATGCTGCCACTTATTACTGCCATCAGCGAGGTAGTTACACGTTCGGAGGGGGA
CCAAGCTGGAAATAAAA(SEQ ID NO:11)

Figure 12: Nucleic acid sequence encoding B4 antibody light chain variable region with codons for amino acid substitutions I10T, M11L, V19A, S51D, and L53T (B4 VKv4)
CAAATTGTTCTCACCCAGTCTCCAGCAACTTTGTCTGCATCTCCAGGGGAGAAGGCTAC
CATGACCTGTAGTGCCAGCTCAGGTGTCAACTACATGCACTGGTACCAGCAGAAGCCAG
GCACCTCCCCCAAAAGATGGATTTATGACACAGACAAAACGGCTTCTGGAGTCCCTGCT
CGCTTCAGTGGCAGTGGGTCTGGGACCTCTTATTCTCTCACAATCAGCAGCATGGAGGC
TGAAGATGCTGCCACTTATTACTGCCATCAGCGAGGTAGTTACACGTTCGGAGGGGGA
CCAAGCTGGAAATAAAA(SEQ ID NO:12)

Figure 13: Amino acid sequence of B4 antibody heavy chain variable region (B4 VH0)
QVQLQQPGAEVVKPGASVRLSCKTSGYTFTSNWMHWVKQRPGQGLEWIGEIDPSDSYTN
YNQKFKGKAKLTVDKSSSTAYMEVSSLTSEDSAVYYCARGSNPYYYAMDYWGQGTSVTV
SS(SEQ ID NO:13)

Figure 14: Amino acid sequence of B4 antibody heavy chain variable region with codons for amino acid substitutions K23E, G42D, K69E, and S85D (B4 VHv1)
QVQLQQPGAEVVKPGASVRLSCETSGYTFTSNWMHWVKQRPDQGLEWIGEIDPSDSYTN
YNQKFKGKAELTVDKSSTAYMEVSDLTSEDSAVYYCARGSNPYYYAMDYWGQGTSVTV
SS(SEQ ID NO:14)

Figure 15: Amino acid sequence of B4 antibody heavy chain variable region with codons for amino acid substitutions K69E, and S85D (B4 VHv2)
QVQLQQPGAEVVKPGASVRLSCKTSGYTFTSNWMHWVKQRPGQGLEWIGEIDPSDSYTN
YNQKFKGKAELTVDKSSTAYMEVSDLTSEDSAVYYCARGSNPYYYAMDYWGQGTSVTV
SS(SEQ ID NO:15)

Figure 16: Amino acid sequence of B4 antibody heavy chain variable region with codons for amino acid substitutions Q5E, V12K, R19K, L20V, T24A, S85D, and S88A (B4 VHv3)
QVQLEQPGAEVKKPGASVKVSCKASGYTFTSNWMHWVKQRPGQGLEWIGEIDPSDSYTN
YNQKFKGKAKLTVDKSSTAYMEVSDLTAEDSAVYYCARGSNPYYYAMDYWGQGTSVTV
SS(SEQ ID NO:16)

Figure 17: Amino acid sequence of B4 antibody heavy chain variable region with codons for amino acid substitutions Q5E, R19K, L20V, R40T, Q43K, K65D, S85D, S88A, and V93T (B4 VHv4)
QVQLEQPGAEVVKPGASVKVSCKTSGYTFTSNWMHWVKQTPGKGLEWIGEIDPSDSYTN
YNQKFDGKAKLTVDKSSTAYMEVSDLTAEDSATYYCARGSNPYYYAMDYWGQGTSVTV
SS(SEQ ID NO:17)

Figure 18: Amino acid sequence of B4 antibody heavy chain variable region with codons for amino acid substitutions Q5E, V12K, R19K, L20V, T24A, K38R, R40A, Q43K, K65D, S85D, and V93T (B4 VHv5)
QVQLEQPGAEVKKPGASVKVSCKASGYTFTSNWMHWVRQAPGKGLEWIGEIDPSDSYTN
YNQKFDGKAKLTVDKSSTAYMEVSDLTSEDSATYYCARGSNPYYYAMDYWGQGTSVTV
SS (SEQ ID NO: 18)

Figure 19: Amino acid sequence of B4 antibody heavy chain variable region with codons for amino acid substitutions Q5E, R19K, L20V, K65D, S85D, and V93T (B4 VHv6)
QVQLEQPGAEVVKPGASVKVSCKTSGYTFTSNWMHWVKQRPGQGLEWIGEIDPSDSYTN
YNQKFDGKAKLTVDKSSTAYMEVSDLTSEDSATYYCARGSNPYYYAMDYWGQGTSVTV
SS (SEQ ID NO:19)

Figure 20: Amino acid sequence of B4 antibody heavy chain variable region with codons for amino acid substitutions V12K, K23E, G42D, K65D, K69E, and S85D (B4 VHv11)
QVQLQQPGAEVKKPGASVRLSCETSGYTFTSNWMHWVKQRPDQGLEWIGEIDPSDSYTN
YNQKFDGKAELTVDKSSSTAYMEVSDLTSEDSAVYYCARGSNPYYYAMDYWGQGTSVTV
SS(SEQ ID NO:20)

Figure 21: Amino acid sequence of B4 antibody heavy chain variable region with codons for amino acid substitutions Q5E, V12K, R19K, L20V, T24A, R40T, Q43K, K65D, S85D, S88A, and V93T (B4 VHv34)
QVQLEQPGAEVKKPGASVKVSCKASGYTFTSNWMHWVKQTPGKGLEWIGEIDPSDSYTN
YNQKFDGKAKLTVDKSSSTAYMEVSDLTAEDSATYYCARGSNPYYYAMDYWGQGTSVTV
SS(SEQ ID NO:21)

Figure 22: Amino acid sequence of B4 antibody heavy chain framework region 1 with variable amino acid residues X5, X12, X19, X20, X23, and X24 (B4 VHfr1)
QVQLXQPGAEVXKPGASVXXSCXXSGYTFT(SEQ ID NO:22)

Figure 23: Amino acid sequence of B4 antibody heavy chain framework region 2 with variable amino acid residues X3, X5, X7, and X8 (B4 VHfr2)
WVXQXPXXGLEWIG (SEQ ID NO:23)

Figure 24: Amino acid sequence of B4 antibody heavy chain framework region 3 with variable amino acid residues X6, X10, X26, X29, and X34 (B4 VHfr3)
YNQKFXGKAXLTVDKSSSTAYMEVSXLTXEDSAXYYCAR(SEQ ID NO:24)

Figure 25: Amino acid sequence of B4 antibody light chain variable region (B4 VK0)
QIVLTQSPAIMSASPGEKVTMTCSASSGVNYMHWYQQKPGTSPKRWIYDTSKLASGVPA
RFSGSGSGTSYSLTISSMEAEDAATYYCHQRGSYTFGGGTKLEIK(SEQ ID NO:25)

Figure 26: Amino acid sequence of B4 antibody light chain variable region with codons for amino acid substitutions V3A, S7E, and A54D (B4 VKv1)
QIALTQEPAIMSASPGEKVTMTCSASSGVNYMHWYQQKPGTSPKRWIYDTSKLDSGVPA
RFSGSGSGTSYSLTISSMEAEDAATYYCHQRGSYTFGGGTKLEIK(SEQ ID NO:26)

Figure 27: Amino acid sequence of B4 antibody light chain variable region with codons for amino acid substitutions Q1D, I10T, M11L, and A54D (B4 VKv2)
DIVLTQSPATLSASPGEKVTMTCSASSGVNYMHWYQQKPGTSPKRWIYDTSKLDSGVPA
RFSGSGSGTSYSLTISSMEAEDAATYYCHQRGSYTFGGGTKLEIK(SEQ ID NO:27)

Figure 28: Amino acid sequence of B4 antibody light chain variable region with codons for amino acid substitutions I10T, M11L, V19A, V29A, and S75E (B4 VKv3)
QIVLTQSPATLSASPGEKATMTCSASSGANYMHWYQQKPGTSPKRWIYDTSKLASGVPA
RFSGSGSGTSYSLTIESMEAEDAATYYCHQRGSYTFGGGTKLEIK(SEQ ID NO:28)

Figure 29: Amino acid sequence of B4 antibody light chain variable region with codons for amino acid substitutions I10T, M11L, V19A, S51D, and L53T (B4 VKv4)
QIVLTQSPATLSASPGEKATMTCSASSGVNYMHWYQQKPGTSPKRWIYDTDKTASGVPA
RFSGSGSGTSYSLTISSMEAEDAATYYCHQRGSYTFGGGTKLEIK(SEQ ID NO:29)

Figure 30: Amino acid sequence of B4 antibody light chain variable region with codons for amino acid substitutions V3A, S7E, V19A, A54D, and S75E (B4 VKv11)
QIALTQEPAIMSASPGEKATMTCSASSGVNYMHWYQQKPGTSPKRWIYDTSKLDSGVPA
RFSGSGSGTSYSLTIESMEAEDAATYYCHQRGSYTFGGGTKLEIK(SEQ ID NO:30)

Figure 31: Amino acid sequence of B4 antibody light chain variable region with codons for amino acid substitutions I10T, M11L, V19A, V29A, S51D, L53T, and S75E (B4 VKv34)
QIVLTQSPATLSASPGEKATMTCSASSGANYMHWYQQKPGTSPKRWIYDTDKTASGVPA
RFSGSGSGTSYSLTIESMEAEDAATYYCHQRGSYTFGGGTKLEIK(SEQ ID NO:31)

Figure 32: Amino acid sequence of B4 antibody light chain framework region 1 with variable amino acid residues X1, X3, X7, X10, X11 and X19 (B4 VKfr1)
XIXLTQXPAXXSASPGEKXTMTC(SEQ ID NO:32)

Figure 33: Amino acid sequence of B4 antibody light chain complementarity determining region 2 with variable amino acid residues X3, X5, and X6 (B4 VKcdr2)
DTXKXXS(SEQ ID NO:33)

Figure 34: Amino acid sequence of B4 antibody heavy chain variable region with underlined CDRs and highlighted substitutable amino acids (B4 VH0) (SEQ ID NO:13)
```
  1 QVQLQQPGAEVVKPGASVRLSCKTSGYTFTSNWMHWVKQRPGQGLEWIGEIDPSD   B4 VH0
 56 SYTNYNQKFKGKAKLTVDKSSTAYMEVSSLTSEDSAVYYCARGSNPYYYAMDYW    B4 VH0
111 GQGTSVTVSS                                                 B4 VH0
```

Figure 35: Amino acid sequence of B4 antibody light chain variable region with underlined CDRs and highlighted substitutable amino acids (B4 VK0) (SEQ ID NO:25)
```
  1 QIVLTQSPAIMSASPGEKVTMTCSASSGVNYMHWYQQKPGTSPKRWIYDTSKLAS   B4 VK0
 56 GVPARFSGSGSGTSYSLTISSMEAEDAATYYCHQRGSYTFGGGTKLEIK         B4 VK0
```

Figure 36: Alignment of B4 antibody heavy chain variable region amino acid sequences

```
  1 QVQLQQPGAEVVKPGASVRLSCKTSGYTFTSNWMHWVKQRPGQGLEWIGEIDPSD  B4 VH0
  1 ....................E....................D............  B4 VHv1
  1 .......................................................  B4 VHv2
  1 ....E......K......KV...A...............................  B4 VHv3
  1 ....E......K......KV..................T..K.............  B4 VHv4
  1 ....E......K......KV...A............R.A..K.............  B4 VHv5
  1 ..........K......E....................D................  B4 VHv11
  1 ....E......K......KV...A..............T..K.............  B4 VHv34

56 SYTNYNQKFKGKAKLTVDKSSSTAYMEVSSLTSEDSAVYYCARGSNPYYYAMDYW  B4 VH0
 56 ..............E...................D.........................  B4 VHv1
 56 ..............E...................D.........................  B4 VHv2
 56 ..................................D..A......................  B4 VHv3
 56 ..........D.......................D..A....T.................  B4 VHv4
 56 ..........D.......................D......T..................  B4 VHv5
 56 ..........D...E...................D..........................  B4 VHv11
 56 ..........D.......................D..A....T.................  B4 VHv34
                                                               SEQ ID NO:
111 GQGTSVTVSS                                              B4 VH0     13
111 ..........                                              B4 VHv1    14
111 ..........                                              B4 VHv2    15
111 ..........                                              B4 VHv3    16
111 ..........                                              B4 VHv4    17
111 ..........                                              B4 VHv5    18
111 ..........                                              B4 VHv11   20
111 ..........                                              B4 VHv34   21
```

Figure 37: Alignment of B4 antibody light chain variable region amino acid sequences

```
  1 QIVLTQSPAIMSASPGEKVTMTCSASSGVNYMHWYQQKPGTSPKRWIYDTSKLAS  B4 VK0
  1 ..A...E...............................................D.  B4 VKv1
  1 D........TL...........................................D.  B4 VKv2
  1 .........TL......A.........A..............................  B4 VKv3
  1 .........TL......A........................................D.T..  B4 VKv4
  1 ..A...E..........A.........................................D.  B4 VKv11
  1 .........TL......A........A...............................D.T..  B4 VKv34
                                                               SEQ ID NO:
 56 GVPARFSGSGSGTSYSLTISSMEAEDAATYYCHQRGSYTFGGGTKLEIK       B4 VK0     25
 56 ................................................       B4 VKv1    26
 56 ................................................       B4 VKv2    27
 56 ................E...............................       B4 VKv3    28
 56 ................................................       B4 VKv4    29
 56 ................E...............................       B4 VKv11   30
 56 ................E...............................       B4 VKv34   31
```

ANTI-CD19 ANTIBODIES WITH REDUCED IMMUNOGENICITY

CROSS-REFERENCE TO RELATED APPLICATIONS

This application is a continuation of U.S. patent application Ser. No. 14/620,955 filed Feb. 12, 2015, which is a divisional of U.S. patent application Ser. No. 14/222,517, filed Mar. 21, 2014, now U.S. Pat. No. 8,957,195, which is a divisional of U.S. patent application Ser. No. 11/648,505, filed Dec. 29, 2006, now U.S. Pat. No. 8,691,952, which claims benefit of and priority to U.S. Provisional Patent Application No. 60/755,609, filed Dec. 30, 2005, the entire disclosures of each of which are incorporated herein by reference.

FIELD OF THE INVENTION

The invention relates generally to variable regions of the anti-CD19 murine monoclonal antibody B4 light chain and heavy chain modified to reduce their immunogenicity.

BACKGROUND

CD19 is a surface protein found on B cells and on certain cancerous cells derived from B cells, such as many B cell lymphomas. Anti-CD19 monoclonal antibodies have been generated in mice, and show some promise in pre-clinical animal models of B cell-derived cancers. However, mouse-derived antibodies are generally immunogenic in humans. A number of strategies have been developed to alter mouse-derived antibodies to minimize their immunogenicity in humans. One such strategy, chimerization, involves the fusion of mouse variable regions to human constant regions. However, the mouse-derived variable region sequences remaining following chimerization will often be immunogenic. Another such strategy, humanization, involves the replacement of mouse-derived framework regions (FRs) within the variable regions with the most closely related human-derived sequences, with the optional reversion of certain amino acids back to the corresponding mouse amino acid in order to maintain binding activity. However, even humanized antibodies may be immunogenic, since the antibody complementarity determining regions (CDRs) generally contain B cell epitopes and T cell epitopes that are non-self. Indeed, even fully human antibodies are immunogenic; this is the basis for the formation of anti-idiotype antibodies during the course of an immune response. All of these problems may apply to mouse-derived anti-CD19 antibodies as they would to any other type of antibody. Therefore, there is a need for anti-CD19 antibodies with reduced immunogenicity.

SUMMARY OF THE INVENTION

The present invention is directed to an anti-CD19 murine monoclonal B4 antibody which has been modified to reduce its immunogenicity in comparison to wild-type B4 antibody. More specifically, the variable region of the B4 antibody of the invention is modified to remove potential T-cell epitopes. As a result, B4 antibodies of the invention have improved biological properties compared to wild-type B4 antibodies.

Accordingly, in one aspect, the invention features an amino acid sequence defining a modified immunoglobulin heavy chain framework region comprising amino acid residues 1-30 of SEQ ID NO:22, wherein one or more of the amino acid residues at positions X5, X12, X19, X20, X23, and X24 are as follows: X5 is Q or E, X12 is V or K, X19 is R or K, X20 is L or V, X23 is K, E or D, or X24 is T or A. According to this aspect of the invention, at least one of the amino acid residues at positions X5, X12, X19, X20, X23, or X24 is not the same amino acid residue as the amino acid at the corresponding position in the unmodified immunoglobulin heavy chain framework region as set forth in amino acid residues 1-30 of SEQ ID NO:13. In one embodiment, X23 is E or D.

In another aspect, the invention features an amino acid sequence defining a modified immunoglobulin heavy chain framework region comprising amino acid residues 1-14 of SEQ ID NO:23, wherein one or more of the amino acid residues at positions X3, X5, X7, and X8, are as follows: X3 is K or R, X5 is R, T, or A, X7 is G, D, or E, or X8 is Q or K. According to this aspect of the invention, at least one of the amino acid residues at positions X3, X5, X7, or X8 is not the same as the amino acid at the corresponding position in the unmodified immunoglobulin heavy chain framework region as set forth in amino acid residues 36-49 of SEQ ID NO: 13. In one embodiment, X7 is E or D.

In another aspect, the invention features an amino acid sequence defining a modified immunoglobulin heavy chain framework region comprising amino acid residues 1-39 of SEQ ID NO:24, wherein one or more of the amino acid residues at positions X6, X10, X26, X29, and X34 are as follows: X6 is K, D, or E, X10 is K, E, or D, X26 is S, D, or E, X29 is S or A, or X34 is V or T. According to this aspect of the invention, at least one of the amino acid residues at positions X6, X10, X26, X29, or X34 is not the same as the amino acid at the corresponding position in the unmodified immunoglobulin heavy chain framework region as set forth in amino acid residues 60-98 of SEQ ID NO:13. In one embodiment, X10 is E or D.

According to another aspect, the invention features an amino acid sequence defining a modified immunoglobulin light chain framework region comprising amino acid residues 1-23 of SEQ ID NO:32, wherein one or more of the amino acid residues at positions X1, X3, X7, X10, X11, and X19 are as follows: X1 is Q or D, X3 is V or A, X7 is S or E, X10 is I or T, X11 is M or L, or X19 is V or A. According to this aspect of the invention, at least one of the amino acid residues at positions X1, X3, X7, X10, X11, or X19 is not the same as the amino acid at the corresponding position in the unmodified immunoglobulin light chain framework region as set forth in amino acid residues 1-23 of SEQ ID NO:25. In one embodiment, X3 is A and X7 is E. In another embodiment, X1 is D, X10 is I, and X11 is L.

In another aspect, the invention features an amino acid sequence defining a modified immunoglobulin light chain complementarity determining region comprising amino acid residues 24-33 of SEQ ID NO:28.

In another aspect, the invention features an amino acid sequence defining a modified immunoglobulin light chain framework region comprising amino acid residues 56-87 of SEQ ID NO:28.

According to another aspect, the invention features an antibody variable region comprising an amino acid sequence selected from the group consisting of SEQ ID NO: 14, SEQ ID NO: 15, SEQ ID NO: 16, SEQ ID NO: 17, SEQ ID NO: 20, SEQ ID NO: 21, SEQ ID NO: 26, SEQ ID NO: 27, SEQ ID NO: 28, SEQ ID NO: 29, SEQ ID NO: 30, or SEQ ID NO: 31, wherein the antibody variable region specifically binds to CD19.

According to another aspect, the invention features a polypeptide at least 90% or at least 95% identical to a B4 antibody heavy chain variable region, the polypeptide comprising an amino acid substitution at one or more residues corresponding to Val12, Leu20, Lys23, Thr24, Lys38, Gly42, Gln43, Lys65, Lys69, Ser85, Ser88, or Val93. In one embodiment, the polypeptide comprises one or more of substitutions Gln5Glu, Val12Lys, Arg19Lys, Leu20Val, Lys23Glu, Lys23Asp, Thr24Ala, Lys38Arg, Arg40Thr, Gly42Asp, Gly42Glu, Gln43Lys, Lys65Asp, Lys65Glu, Lys69Glu, Lys69Asp, Ser85Asp, Ser85Glu, Ser88Ala, or Val93Thr.

According to another aspect, the invention features a polypeptide at least 90% or at least 95% identical to a B4 antibody light chain variable region, the polypeptide comprising an amino acid substitution at one or more residues corresponding to Val3, Ser7, Ile10, Met11, Val19, Val29, Ser51, Leu53, Ala54, or Ser75. In one embodiment, the polypeptide comprises one or more of substitutions Gln1Asp, Val3Ala, Ser7Glu, Ile10Thr, Met11Leu, Val19Ala, Val29Ala, Ser5 Asp, Leu53Thr, Ala54Asp, or Ser75Glu.

In another aspect, the invention features a nucleic acid encoding a polypeptide according to any one of the embodiments of the invention.

In another aspect, the invention features a method of treating a patient, the method comprising the step of administering a therapeutically effective amount of a polypeptide according to any one of the embodiments of the invention to a patient.

In another aspect, the invention features a method for targeting a cell with CD19 on its surface, the method comprising the step of administering an antibody variable region according to any one of the embodiments of the invention. In one embodiment of the method the cell is a tumor cell.

BRIEF DESCRIPTION OF THE DRAWINGS

FIG. 1 depicts the nucleic acid sequence encoding B4 antibody heavy chain variable region (B4 VH0) (SEQ ID NO:1).

FIG. 2 depicts the nucleic acid sequence encoding an exemplary B4 antibody heavy chain variable region incorporating codons for the mutations K23E, G42D, K69E, and S85D (B4 VHv1) (SEQ ID NO:2).

FIG. 3 depicts the nucleic acid sequence encoding an exemplary B4 antibody heavy chain variable region incorporating codons for the mutations K69E, and S85D (B4 VHv2) (SEQ ID NO:3).

FIG. 4 depicts the nucleic acid sequence encoding an exemplary B4 antibody heavy chain variable region incorporating codons for the mutations Q5E, V12K, R19K, L20V, T24A, S85D, and S88A (B4 VHv3) (SEQ ID NO:4).

FIG. 5 depicts the nucleic acid sequence encoding an exemplary B4 antibody heavy chain variable region incorporating codons for the mutations Q5E, R19K, L20V, R40T, Q43K, K65D, S85D, S88A, and V93T (B4 VHv4) (SEQ ID NO:5).

FIG. 6 depicts the nucleic acid sequence encoding an exemplary B4 antibody heavy chain variable region incorporating codons for the mutations Q5E, V12K, R19K, L20V, T24A, K38R, R40A, Q43K, K65D, S85D, and V93T (B4 VHv5) (SEQ ID NO:6).

FIG. 7 depicts the nucleic acid sequence encoding an exemplary B4 antibody heavy chain variable region incorporating codons for the mutations Q5E, R19K, L20V, K65D, S85D, and V93T (B4 VHv6) (SEQ ID NO:7).

FIG. 8 depicts the nucleic acid sequence encoding B4 antibody light chain variable region (B4 VK0) (SEQ ID NO:8).

FIG. 9 depicts the nucleic acid sequence encoding an exemplary B4 antibody light chain variable region incorporating codons for the mutations V3A, S7E, and A54D (B4 VKv1) (SEQ ID NO:9).

FIG. 10 depicts the nucleic acid sequence encoding an exemplary B4 antibody light chain variable region incorporating codons for the mutations Q1D, I10T, MIL, and A54D (B4 VKv2) (SEQ ID NO:10).

FIG. 11 depicts the nucleic acid sequence encoding an exemplary B4 antibody light chain variable region incorporating codons for the mutations I10T, M11L, V19A, V29A, and S75E (B4 VKv3) (SEQ ID NO:11).

FIG. 12 depicts the nucleic acid sequence encoding an exemplary B4 antibody light chain variable region incorporating codons for the mutations I10T, M11L, V19A, S51D, and L53T (B4 VKv4) (SEQ ID NO:12).

FIG. 13 depicts the amino acid sequence of B4 antibody heavy chain variable region (B4 VH0) (SEQ ID NO:13).

FIG. 14 depicts the amino acid sequence of an exemplary B4 antibody heavy chain variable region with the mutations K23E, G42D, K69E, and S85D (B4 VHv1) (SEQ ID NO:14).

FIG. 15 depicts the amino acid sequence of an exemplary B4 antibody heavy chain variable region with the mutations K69E, and S85D (B4 VHv2) (SEQ ID NO:15).

FIG. 16 depicts the amino acid sequence of an exemplary B4 antibody heavy chain variable region with the mutations Q5E, V12K, R19K, L20V, T24A, S85D, and S88A (B4 VHv3) (SEQ ID NO: 16).

FIG. 17 depicts the amino acid sequence of an exemplary B4 antibody heavy chain variable region with the mutations Q5E, R19K, L20V, R40T, Q43K, K65D, S85D, S88A, and V93T (B4 VHv4) (SEQ ID NO: 17).

FIG. 18 depicts the amino acid sequence of an exemplary B4 antibody heavy chain variable region with the mutations Q5E, V12K, R19K, L20V, T24A, K38R, R40A, Q43K, K65D, S85D, and V93T (B4 VHv5) (SEQ ID NO:18).

FIG. 19 depicts the amino acid sequence of an exemplary B4 antibody heavy chain variable region with the mutations Q5E, R19K, L20V, K65D, S85D, and V93T (B4 VHv6) (SEQ ID NO:19).

FIG. 20 depicts the amino acid sequence of an exemplary B4 antibody heavy chain variable region with the mutations V12K, K23E, G42D, K65D, K69E, and S85D (B4 VHv11) (SEQ ID NO:20).

FIG. 21 depicts the amino acid sequence of an exemplary B4 antibody heavy chain variable region with the mutations Q5E, V12K, R19K, L20V, T24A, R40T, Q43K, K65D, S85D, S88A, and V93T (B4 VHv34) (SEQ ID NO:21).

FIG. 22 depicts the amino acid sequence of an exemplary B4 antibody heavy chain framework region with undefined amino acid residues X5, X12, X19, X20, X23, and X24 (B4 VHfr1) (SEQ ID NO:22).

FIG. 23 depicts the amino acid sequence of an exemplary B4 antibody heavy chain framework region 2 with undefined amino acid residues X3, X5, X7, and X8 (B4 VHfr2) (SEQ ID NO: 23)

FIG. 24 depicts the amino acid sequence of an exemplary B4 antibody heavy chain framework region 3 with undefined amino acid residues X6, X10, X26, X29, and X34 (B4 VHfr3) (SEQ ID NO:24).

FIG. 25 depicts the amino acid sequence of B4 antibody light chain variable region (B4 VK0) (SEQ ID NO:25).

FIG. 26 depicts the amino acid sequence of an exemplary B4 antibody light chain variable region with the mutations V3A, S7E, and A54D (B4 VKv1) (SEQ ID NO:26).

FIG. 27 depicts the amino acid sequence of an exemplary B4 antibody light chain variable region with the mutations Q1D, I10T, M11L, and A54D (B4 VKv2) (SEQ ID NO:27).

FIG. 28 depicts the amino acid sequence of an exemplary B4 antibody light chain variable region with the mutations I10T, M11L, V19A, V29A, and S75E (B4 VKv3) (SEQ ID NO:28).

FIG. 29 depicts the amino acid sequence of an exemplary B4 antibody light chain variable region with the mutations I10T, M11L, V19A, S51D, and L53T (B4 VKv4) (SEQ ID NO:29).

FIG. 30 depicts the amino acid sequence of an exemplary B4 antibody light chain variable region with the mutations V3A, S7E, V19A, A54D, and S75E (B4 VKv11) (SEQ ID NO:30).

FIG. 31 depicts the amino acid sequence of an exemplary B4 antibody light chain variable region with the mutations I10T, M11L, V19A, V29A, S51D, L53T, and S75E (B4 VKv34) (SEQ ID NO:31).

FIG. 32 depicts the amino acid sequence of an exemplary B4 antibody light chain framework region with undefined amino acid residues X1, X3, X7, X10, X11, and X19 (B4 VKfr1) (SEQ ID NO:32).

FIG. 33 depicts the amino acid sequence of an exemplary B4 antibody light chain complementarity determining region with undefined amino acid residues X3, X5, and X6 (B4 VKcdr2) (SEQ ID NO:33).

FIG. 34 depicts the amino acid sequence of B4 antibody heavy chain variable region. The complementarity determining regions are underlined. The modifiable amino acid residues are shown in bold.

FIG. 35 depicts the amino acid sequence of B4 antibody light chain variable region. The complementarity determining regions are underlined. The modifiable amino acid residues are shown in bold.

FIG. 36 is an amino acid sequence alignment of B4 antibody heavy chain variable regions VH0 (SEQ ID NO:13), VHv1 (SEQ ID NO:14), VHv2 (SEQ ID NO:15), VHv3 (SEQ ID NO:16), VHv4 (SEQ ID NO:17), VHv5 (SEQ ID NO:18), VHv11 (SEQ ID NO:20), and VHv34 (SEQ ID NO:21).

FIG. 37 is an amino acid sequence alignment of B4 antibody light chain variable regions VK0 (SEQ ID NO:25), VKv1 (SEQ ID NO:26), VKv2 (SEQ ID NO:27), VKv3 (SEQ ID NO:28), VKv4 (SEQ ID NO:29), VKv11 (SEQ ID NO:30), and VKv34 (SEQ ID NO:31).

In FIG. 42(a) treatments are cyclophosphamide (empty squares), the B4 VHv4/VKv4 antibody (X), a combination of the B4 VHv4/VKv4 antibody and cyclophosphamide (filled squares), or PBS (stars). In FIG. 42(b) treatments are vincristine (empty triangles), the B4 VHv4/VKv4 antibody (X), a combination of the B4 VHv4/VKv4 antibody and vincristine (filled triangles), or PBS (stars). In FIG. 42(c) treatments are doxorubicin (empty circles), the B4 VHv4/VKv4 antibody (X), a combination of the B4 VHv4/VKv4 antibody and doxorubicin (filled circles), or PBS (stars).

DETAILED DESCRIPTION OF THE INVENTION

Figure 38:
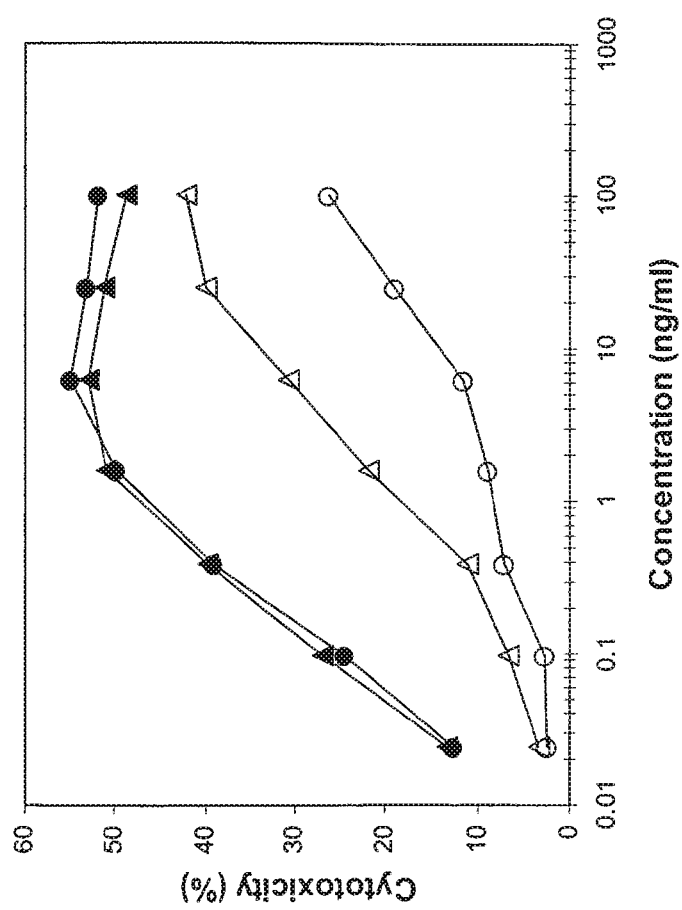
FIG. 38 shows the results of an ADCC assay on Daudi Burkitt's lymphoma cells performed with B4 VHv4/VKv4 antibody expressed either from HEK 293T cells (empty triangles) or from YB2/0 cells (filled triangles), and B4 VHv5/VKv4 antibody expressed either from a NS/0 cell line (empty circles) or from YB2/0 cells (filled circles) as described in Example 4.

The invention is directed to B4 proteins that have reduced immunogenicity as compared to wild-type B4, as well as methods for making and using such proteins. More specifically, the invention provides mutations within a B4 antibody that have the effect of reducing the immunogenicity of a B4 antibody itself, primarily by removing T-cell epitopes within B4 that may stimulate to an immune response.

The present invention is directed to a set of modified antibody heavy chain (VH) and light chain (VK) variable regions of the anti-CD19 murine antibody B4 (Nadler et al., (1983) J. Immunol. 130:2947-2951; Roguska et al., (1994) Proc. Natl. Acad. Sci. USA 91:969-973), which herein are generically termed "B4 VHvx" and "B4 VKvy", respectively. For reference, the sequence of the heavy chain variable region of the original murine B4 antibody (B4 VH0) and the sequence of the light chain variable regions of the original murine B4 antibody (B4 VK0), with the CDRs underlined, are provided in FIGS. 34 and 35, respectively.

As compared to the original B4 VH0 and B4 VK0 polypeptides, B4 VHvx and B4 VKvy polypeptides have reduced immunogenicity. More specifically, the invention provides mutations within B4 VH and/or B4 VK which have the effect of reducing the immunogenicity of B4 variable region polypeptides, primarily by removing T-cell epitopes within these polypeptides that may stimulate an immune response. According to the invention, protein compositions containing the modified forms of the B4 variable regions are less immunogenic when administered to a human, but are still competent to specifically bind CD19 and to target cells expressing CD19.

As used herein, the terms "Complementarity-Determining Regions" and "CDRs" are understood to mean the hypervariable regions or loops of an immunoglobulin variable region that interact primarily with an antigen. The immunoglobulin heavy chain variable region (VH) and immunoglobulin light chain variable region (VK) both contain three CDRs interposed between framework regions, as shown in FIGS. 34 and 35, respectively. For example, with reference to the amino acid sequence defining the immunoglobulin heavy chain variable region of the B4 antibody as shown in FIG. 34 (SEQ ID NO:13), the CDRs are defined by the amino acid sequences from Ser31 to His35 (CDR1), from Glu50 to Asn59 (CDR2), and from Gly99 to Tyr109 (CDR3). With reference to the amino acid sequence defining the immunoglobulin light chain variable region of the B4 antibody as shown in FIG. 35 (SEQ ID NO: 25), the CDRs are defined by the amino acid sequences from Ser24 to His33 (CDR1), from Asp49 to Ser55 (CDR2), and from His88 to Thr94 (CDR3).

As used herein, the terms "Framework Regions" and "FRs" are understood to mean the regions of an immunoglobulin variable region adjacent to the Complementarity-Determining Regions. The immunoglobulin heavy chain variable region (VH) and immunoglobulin light chain variable region (VK) each contain four FRs, as shown in FIGS. 34 and 35. For example, with reference to the amino acid sequence defining the immunoglobulin heavy chain variable of the of the B4 antibody as shown in FIG. 34 (SEQ ID NO: 13), the FRs are defined by the amino acid sequences from Gln1 to Thr30 (FR1), from Trp36 to Gly49 (FR2), from Tyr60 to Arg98 (FR3), and from Trp110 to Ser120 (FR4). With reference to the amino acid sequence defining the immunoglobulin light chain variable region of the B4 antibody as shown in FIG. 35 (SEQ ID NO: 25), the FRs are defined by the amino acid sequences from Gln1 to Cys23 (FR1), from Trp34 to Tyr48 (FR2), from Gly56 to Cys87 (FR3), and from Phe95 to Lys104 (FR4). Furthermore, amino acid residues depicted in bold in FIGS. 34 and 35 are amino acid residues that may be mutated according to various embodiments of the invention.

T-cell epitopes can be identified by a variety of computer and non-computer methods, including predictions based on structure-based computer modeling or by synthesis of peptides and testing for binding to specific MHC Class II molecules or in an immunogenicity assay. According to the invention, a potential T-cell epitope is a sequence that, when considered as an isolated peptide, is predicted to bind to an MHC Class II molecule or an equivalent in a non-human species. A potential T-cell epitope is defined without consideration of other aspects of antigen processing, such as the efficiency of protein uptake into antigen-presenting cells, the efficiency of cleavage at sites in an intact protein to yield a peptide that can bind to MHC Class II, and so on. Thus, the set of T-cell epitopes that are actually presented on MHC Class II after administration of a protein to an animal is a subset of the potential T-cell epitopes. According to the invention, a T-cell epitope is an epitope on a protein that interacts with an MHC class II molecule. Without wishing to be bound by theory, it is understood that a T-cell epitope is an amino acid sequence in a protein that failed to undergo the negative T-cell selection process during T-cell development and therefore will be expected to be presented by an MHC Class II molecule and recognized by a T-cell receptor.

According to one embodiment, the invention provides methods related to reducing the immunogenicity of B4 VH and B4 VK regions. According to one embodiment of the invention, potential non-self T-cell epitopes are identified in sequences of B4 VH or B4 VK. For example, potential non-self T-cell epitopes are identified by computational methods based on modeling peptide binding to MHC Class II molecules. Substitutions to specific amino acid residues are then made such that the ability of peptides containing potential T-cell epitopes to bind to MHC Class II is reduced or eliminated.

Modified Protein Sequences of Variable Regions of the Invention.

According to one embodiment, the effect of a specific amino acid mutation or mutations is predicted based on structure-based computer modeling. For example, ProPred (http://www.imtech.res.in/raghava/propred; Singh and Raghava (2001) Bioinformatics 17:1236-1237) is a publically available web-based tool that can be used for the prediction of peptides that bind HLA-DR alleles. ProPred is based on a matrix prediction algorithm described by Sturniolo for a set of 50 HLA-DR alleles (Sturniolo et al., (1999) Nature Biotechnol. 17:555-561). Using such an algorithm, various peptide sequences were discovered within B4 VH and B4 VK which are predicted to bind to multiple MHC class II alleles and are therefore likely to be immunogenic. These peptide sequences and their predicted binding frequency to HLA-DR alleles are shown in Table 1.

With reference to Table 1, the sequence of each 9-mer peptide that binds to at least 5 HLA-DR alleles is indicated, along with its position (#) in the B4 VH region (left column) or B4 VK region (right column). "Bind freq." refers to the number of alleles, out of a possible 50 alleles, that the peptide binds, above an arbitrary binding threshold, in this case 20%. A binding frequency of "+" indicates the peptide binds to 5-9 alleles, "++" indicates the peptide binds to 10-19 alleles, and "+++" indicates the peptide binds to 20-50 alleles. The 20% binding threshold is relative to a theoretical maximum binding score, as calculated by an algorithm as described by Sturniolo et al.

TABLE 1

Selected peptides of B4 V regions predicted to bind human HLA-DR alleles.

| VH T cell epitopes (start pos.) | bind freq. | VK T cell epitopes (start pos.) | bind freq. |
| --- | --- | --- | --- |
| (2) VQLQQPGAE | + | (2) IVLTQSPAI | +++ |
| (12) VKPGASVRL | + | (3) VLTQSPAIM | ++ |
| (18) VRLSCKTSG | +++ | (19) VTMTCSASS | + |
| (36) WVKQRPGQG | + | (29) VNYMHWYQQ | + |
| (60) YNQKFKGKA | + | (46) WIYDTSKLA | ++ |
| (64) FKGKAKLTV | +++ | (47) IYDTSKLAS | + |
| (80) YMEVSSLTS | ++ | | |
| (93) VYYCARGSN | + | | |

These potentially immunogenic sequences in the B4 VH and B4 VK polypeptides can be rendered less immunogenic by introducing specific mutations that reduce or eliminate the binding of a particular peptide to a human HLA-DR allele (see, for example WO98/52976 and WO00/34317). Alternatively, non-human T-cell epitopes are mutated so that they correspond to human self epitopes that are present in human germline antibodies (see for example U.S. Pat. No. 5,712,120).

Guidance for selecting appropriate mutations may be obtained by reference to tertiary and quaternary structure of antibody variable regions. Crystal structures of antibody variable domains are known in the art and it is found that structures of the FRs are generally very similar to one another. A theoretical model of the antibody variable region of anti-CD19 antibody B4 VH0/VK0 can be constructed from the most closely related antibody heavy and light chain variable regions for which a structure has been determined, which can be identified by from a primary structure alignment (Altschul et al., (1990) J. Mol. Biol. 215:403-415). A threading algorithm is used to model the B4 light and heavy chains onto the solved structures (Marti-Renom et al., (2000) Annu Rev Biophys Biomol Struct 29:291-325), and the threaded structures may be further refined to obtain stereochemically favorable energies (Weiner et al., (1984) J Am Chem Soc 106:765-784). It was found that the solved heavy chain and light chain structures designated respectively by their PDB database accession codes 1FBI (Fab fragment of monoclonal antibody F9.13.7) and 1MIM (Fab fragment of anti-CD25 chimeric antibody Sdz Chi621), were useful reference structures for this purpose.

Preferred mutations do not unduly interfere with protein expression, folding, or activity. According to the invention, amino acids at positions Q5, V12, R19, L20, K23, T24, K38, R40, G42, Q43, K65, K69, S85, S88, or V93 in B4 VH and amino acids at positions Q1, V3, S7, I10, M11, V19, V29, S51, L53, A54, or S75 in B4 VK can be mutated while still retaining the ability of the antibody to be expressed and to bind to CD19 at levels comparable to the unmodified form of B4. Thus the invention encompasses B4 antibodies having at least one modification in the VH sequence selected from the group of amino acid positions consisting of Q5, V12, R19, L20, K23, T24, K38, R40, G42, Q43, K65, K69, S85, S88, and V93 and/or having at least one modification in the VK sequence selected from the group of amino acid positions consisting of Q1, V3, S7, I10, M11, V19, V291 S51, L53, A54, and S75.

A nonexhaustive list of specific positions found to tolerate amino acid substitutions according to the invention is presented in Table 2, together with exemplary substitutions at those positions.

TABLE 2

Substitutions in B4 V regions.

| Position in B4 VH | Substitution | Position in B4 VK | Substitution |
|---|---|---|---|
| Gln5 | Glu | Gln1 | Asp |
| Val12 | Lys | Val3 | Ala |
| Arg19 | Lys | Ser7 | Glu |
| Leu20 | Val | Ile10 | Thr |
| Lys23 | Glu, Asp | Met11 | Leu |
| Thr24 | Ala | Val19 | Ala |
| Lys38 | Arg | Val29 | Ala |
| Arg40 | Ala, Thr | Ser51 | Asp |
| Gly42 | Asp, Glu | Leu53 | Thr |
| Gln43 | Lys | Ala54 | Asp |
| Lys65 | Asp, Glu | Ser75 | Glu |
| Lys69 | Glu, Asp | | |
| Ser85 | Asp, Glu | | |
| Ser88 | Ala | | |
| Val93 | Thr | | |

One set of embodiments includes amino acid substitutions in the B4 VH polypeptide, selected from Q5E, V12K, R19K, L20V, K23E, T24A, K38R, R40T, G42D, Q43K, K65D, K69E, S85D, S88A, and V93T. Additionally contemplated substitutions are K23D, G42E, K65E and K69D. Particular combinations of mutations are also found to be useful. For example, in one specific embodiment, the substitutions K23E and K69E are included. In another specific embodiment, additionally the substitutions G42D and S88A are included, as shown, for example, for B4 VHv1 (SEQ ID NO: 14). In yet another specific embodiment, VHv1 additionally includes the substitutions V12K and K65D (B4 VHv11) (SEQ ID NO:20). In a further specific embodiment the substitutions Q5E, V12K, R19K, L20V, S85D, and S88A are included, as exemplified by B4 VHv3 (SEQ ID NO:16). In yet a further specific embodiment the substitutions Q5E, R19K, L20V, R40T, Q43K, K65D, S85D, S88A, and V93T are included, as exemplified by B4 VHv4 (SEQ ID NO: 17). In yet a further specific embodiment the substitutions Q5E, R19K, L20V, K38R, R40A, Q43K, K65D, S85D, and V93T are included, as exemplified by B4 VHv5 (SEQ ID NO: 18). In another specific embodiment, substitutions of B4 VHv3 and B4 VHv4 are combined, as shown in the sequence of B4 VHv34 (SEQ ID NO:21).

Another set of embodiments includes amino acid substitutions in the B4 VK polypeptide, selected from Q1D, V3A, S7E, I10T, M11L, V19A, V29A, S51D, L53T, A54D, and S75E. In one specific embodiment, the substitution A54D is included. Particular combinations of mutations are also found to be useful. For example, in more specific embodiments, additionally the substitutions V3A and S7E are included, as exemplified by B4 VKv1 (SEQ ID NO:26), or the substitutions Q1D, I10T, and M11L are included, as exemplified by B4 VKv2 (SEQ ID NO:27). In a further embodiment, B4 VK1 additionally includes the substitutions V19A and S75E, as exemplified in B4 VKv11 (SEQ ID NO:30). In yet another embodiment, the substitutions I10T, M11L, V19A, V29A, and S75E are included, as exemplified by B4 VKv3 (SEQ ID NO:28). In yet a further specific embodiment, the substitutions I10T, M11L, V19A, SS1D, and L53T are included, as exemplified by B4 VKv4 (SEQ ID NO:29). In another specific embodiment, substitutions of B4 VKv3 and B4 VKv4 are combined, as shown in the sequence of B4 VKv34 (SEQ ID NO:31).

A primary structure alignment of some exemplary sequences of B4 VHvx and B4 VKvx of the invention, described above, are presented in FIGS. 36 and 37, respectively. Amino acids depicted in bold are positions of VH0 and VK0 that may be mutated according to the invention, and underlined amino acids represent CDRs. VHv1-VHv34 and VKv1-VKv34 are representative heavy and light chains, respectively, with specific amino acid substitutions that reduce immunogenicity.

Variable region compositions of the invention include at least a heavy chain or a light chain of the invention. For example, in one embodiment, the variable region contains B4 VHv1 (SEQ ID NO: 14) and B4 VK0 (SEQ ID NO:25). In another embodiment, the variable region contains B4 VHv1 (SEQ ID NO:14) and B4 VKv1 (SEQ ID NO:26). In yet another embodiment, the variable region contains B4 VHv4 (SEQ ID NO:17) and B4 VKv4 (SEQ ID NO:29). In yet another embodiment, the variable region contains B4 VHv5 (SEQ ID NO:23) and B4 VKv4 (SEQ ID NO:29). It is appreciated that other embodiments of the invention are easily obtained by combinatorially matching the complete set of B4 VHvx and B4 VKvy polypeptides contemplated by the invention. Useful combinations are further determined experimentally, by analyzing protein compositions containing these combinations, such as a B4 VHvx/VKvy antibody, for their expressibility and CD-19 binding activity, as well as their reduced immunogenicity, as described in more detail below.

Verification of the Reduced Immunogenicity of Variable Regions of the Invention.

To verify that a mutation of the invention has indeed resulted in reduced immunogenicity, standard experimental tests, which are well known in the art, can be employed. For example, a T-cell stimulation assay may be used (e.g. Jones et al., (2004), *J. Interferon Cytokine Res.*, 24:560). In such an assay, human peripheral blood mononuclear cells (PBMCs) are obtained and cultured according to standard conditions. After an optional pre-stimulation, a peptide corresponding to a potential MHC Class II epitope is added to the culture of PBMCs; the PBMCs are further incubated, and at a later time tritiated thymidine is added. The peptide can be a minimal 9-mer, or can have about 10 to 15, or more than 15, amino acids. After further incubation of the cells, incorporation of tritiated thymidine into DNA is then measured by standard techniques.

The T-cell stimulation assay is thought to work by the following mechanisms. First, if a peptide is used as a stimulator, the peptide must first bind to an MHC Class II molecule present on a cell among the PBMCs. Second, the MHC Class II/peptide complex must interact productively with a T-cell receptor on a CD4+ T-cell. If the test peptide is unable to bind sufficiently tightly to an MHC Class II molecule, no signal will result. If the peptide is able to bind an MHC Class II molecule and there are T-cells expressing an appropriately rearranged T-cell receptor capable of recognizing a particular MHC Class II/peptide complex, a signal should result. However, if such T-cells have been deleted as a result of a negative selection process, no signal will result. These mechanisms are considered relevant to the immunogenicity of a protein sequence, as inferred from the stimulation or lack of stimulation by a given peptide.

If recognizing T-cells are present in very low numbers in the PBMC population for stochastic reasons relating to failure of an appropriate T-cell receptor to take place or proliferation of other, unrelated T-cells followed by homeostasis of the T-cell population, there may also be no signal even though a signal is expected. Thus, false negative results may occur. Based on these considerations, it is important to use a large number of different sources of PBMCs and to test these samples independently. It is also generally useful to test PBMCs from an ethnically diverse set of humans, and to determine the MHC Class II alleles present in each PBMC population.

The standard T-cell assay has the disadvantage that the tritium incorporation signal is often only two-fold greater than the background incorporation. The proteins and peptides of the invention may also be tested in a modified T-cell assay in which, for example, purified CD4+ T-cells and purified dendritic cells are co-cultured in the presence of the test peptide, followed by exposure to tritiated thymidine and then assayed for tritiated thymidine incorporation. This second assay has the advantage that tritiated thymidine incorporation into irrelevant cells, such as CD8+ T-cells, is essentially eliminated and background is thus reduced.

A third assay involves the testing of a candidate protein with reduced immunogenicity in an animal such as a primate. Such an assay would generally involve the testing of a B4 VHvx/VKvy protein composition, such as an antibody, that had been designed by testing individual component peptides for potential immunogenicity in a cell-based assay such as one described above. Once such a candidate B4 VHvx/VKvy protein composition is designed and expressed, the protein is tested for immunogenicity by injection into an animal.

Injection of the B4 VHvx/VKvy protein composition is generally performed in the same manner as the anticipated route of delivery during therapeutic use in humans. For example, intradermal, subcutaneous, intramuscular, intraperitoneal injection or intravenous infusion may be used. If more than one administration is used, the administrations may be by different routes.

For immunogenicity testing purposes, it may be useful to coadminister an adjuvant to increase the signal and minimize the number of animals that need to be used. If an adjuvant is used, it is possible to use an adjuvant lacking a protein component, such as DNA with unmethylated CpG dinucleotides, bacterial lipid A, N-formyl methionine, or other bacterial non-protein components. Without wishing to be bound by theory, the rationale for avoiding protein-containing adjuvants is that other proteins may provide T-cell epitopes that will ultimately contribute to an antibody response against the candidate protein.

After one or more administrations of the candidate B4 VHvx/VKvy protein composition, the presence of anti-idiotype antibodies is tested according to standard techniques, such as the ELISA method. It is found that the B4 VHvx/VKvy protein compositions of the invention induce antibody formation less frequently, and to a lesser extent, than corresponding molecules containing original B4 VH/VK sequences.

Other Configurations of the Variable Regions of the Invention.

In addition to the use of the V regions of the invention in a naked antibody, it is also possible to configure the V regions of the invention into antibody fusion proteins that target toxins, immune stimulators, and other proteins, as well as in Fabs, single-chain Fvs, bispecific antibodies, and other configurations known in the art of antibody engineering.

In certain embodiments of the invention, the light chain variable region and the heavy chain variable region can be coupled, respectively, to a light chain constant region and a heavy chain constant region of an immunoglobulin. The immunoglobulin light chains have constant regions that are designated as either kappa or lambda chains. In a particular embodiment of the invention, the light chain constant region is a kappa chain. The heavy chain constant regions, and various modification and combinations thereof are discussed below in more detail.

Fc Portion

The antibody variable domains of the present invention are optionally fused to an Fc portion. As used herein, the Fc portion encompasses domains derived from the heavy chain constant region of an immunoglobulin, preferably a human immunoglobulin, including a fragment, analog, variant, mutant or derivative of the constant region. The constant region of an immunoglobulin heavy chain is defined as a naturally-occurring or synthetically produced polypeptide homologous to at least a portion of the C-terminal region of the heavy chain, including the CH1, hinge, CH2, CH3, and, for some heavy chain classes, CH4 domains. The "hinge" region joins the CH1 domain to the CH2-CH3 region of an Fc portion. The constant region of the heavy chains of all mammalian immunoglobulins exhibit extensive amino acid sequence similarity. DNA sequences for these immunoglobulin regions are well known in the art. (See, e.g., Gillies et al. (1989) J. Immunol. Meth. 125:191).

In the present invention, the Fc portion typically includes at least a CH2 domain. For example, the Fc portion can include the entire immunoglobulin heavy chain constant region (CH1-hinge-CH2-CH3). Alternatively, the Fc portion can include all or a portion of the hinge region, the CH2 domain and the CH3 domain.

The constant region of an immunoglobulin is responsible for many important antibody effector functions, including those mediated by Fc receptor (FcR) binding and by complement binding. There are five major classes of the heavy chain constant region, classified as IgA, IgG, IgD, IgE, and IgM, each with characteristic effector functions designated by isotype.

IgG, for example, is separated into four γ isotypes: γ1, γ2, γ3, and γ4, also known as IgG1, IgG2, IgG3, and IgG4, respectively. IgG molecules can interact with multiple classes of cellular receptors including three classes of Fcγ receptors (FcγR) specific for the IgG class of antibody, namely FcγRI, FcγRII, and FcγRII. The sequences important for the binding of IgG to the FcγR receptors have been reported to be in the CH2 and CH3 domains.

Widely recognized effector functions of antibodies, particularly of the IgG class, include complement-dependent cytotoxicity (CDC) and antibody-dependent cellular cytotoxicity (ADCC). All of the IgG subclasses (IgG1, IgG2, IgG3, IgG4) mediate CDC and ADCC to some extent, with IgG1 and IgG3 being most potent for both activities (Chapter 3, Table 3 in Paul, Essential Immunology 4.sup.th Ed., p. 62). CDC is believed to occur by multiple mechanisms; one mechanism is initiated when an antibody binds to an antigen on a cell's surface. Once the antigen-antibody complex is formed, the C1q molecule is believed to bind the antigen-antibody complex. C1q then cleaves itself to initiate a cascade of enzymatic activation and cleavage of other complement proteins which then bind the target cell surface and facilitate its death through, for example, cell lysis and/or ingestion by a macrophage. ADCC is believed to occur when Fc receptors on cytotoxic cells, such as natural killer (NK) cells, macrophages and neutrophils, bind to the Fc region of antibodies bound to antigen on a cell's surface. Fc receptor binding signals the cytotoxic cell to kill the target cell. Characteristically, NK cells, believed to be the primary mediators of ADCC, express only FcγRIIIa.

It is often useful to alter the effector functions of an antibody. For example, to treat cancers associated with a B cell malignancy or to treat autoimmune diseases with a B cell component, it is useful to enhance the ADCC activity of the antibody. It may be particularly useful to enhance the ADCC activity of an antibody directed to B cell surface antigens present at relatively low density (Niwa et al., (2005) Clin. Cancer Res. 11:2327-2336), such as to CD19. It is believed that the antigen density of CD19 relative to CD20 on the surface of B cells is roughly ten-fold lower. Alterations in antibodies that increase the ADCC activity of an antibody relative to its parent antibody are known in the art, and generally correlate with modifications that increase the binding affinity of the variant antibody to FcγRIII (see for example, U.S. Pat. No. 6,737,056). For example, mutations are introduced into the Fc region at one or more positions (with reference to their position in IgGγ1) selected from 256, 290, 298, 312, 326, 330, 333, 334, 339, 360, 378 and 430 (numbering according to Kabat et al. Sequences of Proteins of Immunological Interest, 1991). Preferred mutations are at one or more positions selected from 298, 333, and 334. For example, alanine substitutions may be introduced.

ADCC activity of the antibody is also influenced by the particular cell line used to produce the antibody. For example, antibodies produced in the mouse myeloma NS/0 cells (or SP2/0 cells) generally have low ADCC, and antibodies produced in rat myeloma YO cells (or YB2/0) cells have high ADCC (Lifely et al., (1995) Glycobiology 5:813-822). It is known in the art that the type of cell line used for antibody expression affects the carbohydrate structure of the N-linked glycosyl chain, which is attached to the Fc region of the antibody at position corresponding to N297 in IgGγ1. The carbohydrate structure of antibodies produced in CHO cells is fucosylated, whereas the carbohydrate chain of antibodies produced in YB2/0 is largely absent of fucose (Shinkawa et al., (2003) JBC 278:3466-3473). Antibodies that lack fucose on the carbohydrate structure bind to human FcγRIIIa with higher affinity (Shields et al., (2002) JBC 277:26733-26740). In certain embodiments, anti-CD19 antibodies with variable regions of the invention are characterized by having reduced fucosylation on the N-linked glycosyl chain of the Fc portion of the antibody.

It is also often useful to alter the serum half-life of the antibody. The serum half-life of an antibody, as of an immunoglobulin fusion protein, is influenced by the ability of that antibody to bind to an Fc receptor (FcR) (Gillies et al., Cancer Research (1999) 59:2159-66). The CH2 and CH3 domains of IgG2 and IgG4 have undetectable or reduced binding affinity to Fc receptors compared to those of IgG1. Accordingly, the serum half-life of the featured antibody can be increased by using the CH2 and/or CH3 domain from IgG2 or IgG4 isotypes. Alternatively, the antibody can include a CH2 and/or CH3 domain from IgG1 or IgG3 with modification in one or more amino acids in these domains to reduce the binding affinity for Fc receptors (see, e.g., U.S. patent application Ser. No. 09/256,156, published as U.S. patent application publication 2003-0105294).

The hinge region of the Fc portion normally adjoins the C-terminus of the CH1 domain of the heavy chain constant region. When included in the proteins of the present invention, the hinge is homologous to a naturally-occurring immunoglobulin region and typically includes cysteine residues linking two heavy chains via disulfide bonds as in natural immunoglobulins. Representative sequences of hinge regions for human and mouse immunoglobulin can be found in ANTIBODY ENGINEERING, a PRACTICAL GUIDE, (Borrebaeck, ed., W. H. Freeman and Co., 1992).

Suitable hinge regions for the present invention can be derived from IgG1, IgG2, IgG3, IgG4, and other immunoglobulin isotypes. The IgG1 isotype has two disulfide bonds in the hinge region permitting efficient and consistent disulfide bonding formation. Therefore, a preferred hinge region of the present invention is derived from IgG1. Optionally, the first, most N-terminal cysteine of an IgG1 hinge is mutated to enhance the expression and assembly of antibodies or antibody fusion proteins of the invention (see, e.g., U.S. patent application Ser. No. 10/093,958, published as U.S. patent application publication 2003-0044423).

In contrast to IgG1, the hinge region of IgG4 is known to form interchain disulfide bonds inefficiently (Angal et al., (1993), Mol. Immunol. 30:105-8). Also, the IgG2 hinge region has four disulfide bonds that tend to promote oligomerization and possibly incorrect disulfide bonding during secretion in recombinant systems. One suitable hinge region for the present invention can be derived from the IgG4 hinge region, preferentially containing a mutation that enhances correct formation of disulfide bonds between heavy chain-derived moieties (Angal et al., (1993), Mol. Immunol. 30(1): 105-8). Another preferred hinge region is derived from an IgG2 hinge in which the first two cysteines are each mutated to another amino acid, such as, in order of general preference, serine, alanine, threonine, proline, glutamic acid, glutamine, lysine, histidine, arginine, asparagine, aspartic acid, glycine, methionine, valine, isoleucine, leucine, tyrosine, phenylalanine, tryptophan or selenocysteine (see, e.g., U.S. patent application publication 2003-0044423).

An Fc portion fused to an antibody variable region of the invention can contain CH2 and/or CH3 domains and a hinge region that are derived from different antibody isotypes. For example, the Fc portion can contain CH2 and/or CH3 domains of IgG2 or IgG4 and a hinge region of IgG1. Assembly of such hybrid Fc portions has been described in U.S. patent application publication 2003-0044423.

When fused to an antibody variable region of the invention, the Fc portion may contain one or more amino acid modifications that generally extend the serum half-life of an Fc fusion protein. Such amino acid modifications include mutations substantially decreasing or eliminating Fc receptor binding or complement fixing activity. For example, one type of such mutation removes the glycosylation site of the Fc portion of an immunoglobulin heavy chain. In IgG1, the glycosylation site is Asn297 (see, for example, U.S. patent application Ser. No. 10/310,719, published as U.S. patent application publication 2003-0166163).

The antibody variable regions of the invention can be attached to a diagnostic and/or a therapeutic agent. The agent can be fused to the antibody to produce a fusion protein. Alternatively, the agent can be chemically coupled to the antibody to produce an immuno-conjugate. The agent can be, for example, a toxin, radiolabel, imaging agent, immunostimulatory moiety or the like.

The antibody variable region of the invention can be attached to a cytokine. Preferred cytokines include interleukins such as interleukin-2 (IL-2), IL-4, IL-5, IL-6, IL-7, IL-10, IL-12, IL-13, IL-14, IL-15, IL-16, IL-18, IL-21, and IL-23, hematopoietic factors such as granulocyte-macrophage colony stimulating factor (GM-CSF), granulocyte colony stimulating factor (G-CSF) and erythropoeitin, tumor necrosis factors (TNF) such as TNFα, lymphokines such as lymphotoxin, regulators of metabolic processes such as leptin, interferons such as interferon α, interferon β, and interferon γ, and chemokines. Preferably, the antibody-cytokine fusion protein or immunoconjugate displays cytokine biological activity. In one embodiment, the antibody variable domain is fused to IL-2. Preferably, several amino acids within the IL-2 moiety are mutated to reduce toxicity, as described in U.S. patent application publication 2003-0166163.

Optionally, the protein complexes can further include a second agent, such as a second cytokine. In one embodiment, a B4 VHvx/VKvy antibody fusion protein includes IL-12 and IL-2. The construction of protein complexes containing an immunoglobulin domain and two, different cytokines is described in detail in U.S. Pat. No. 6,617,135.

Antibody Production

Antibodies of the invention, as well as other variable region-containing proteins of the invention, are produced by methods well known in the art of protein engineering. Nucleic acid vectors capable of expressing a heavy chain and a light chain which include sequences of the invention are introduced into the appropriate cell and the recombinant protein product is expressed and purified. For example, antibodies of the invention can be produced in engineered mammalian cell lines such as NS/0 cells, CHO cells, SP2/0 cells (SP2/0-Ag14; ATCC-CRL 1581), YB2/0 cells (YB2/3HL.P2.G11.16Ag.20; ATCC CRL-1662), or other mammalian cells well known in the art of antibody production. In one embodiment, B4 VHvx/VKvy antibodies are produced in NS/0 cells. In another embodiment, B4 VHvx/VKvy antibodies are produced in YB2/0 cells. Alternatively, yeast, plants, insect cells, or bacteria may be used to produce proteins containing variable regions of the invention.

Administration

The antibodies of the invention are preferably used to treat patients with B cell disorders such as B cell lymphomas or autoimmune disorders with a B cell component such as rheumatoid arthritis, myasthenia gravis, multiple sclerosis, systemic lupus erythematosus, and so on. For B cell lymphoma, depending on the judgment of the physician, it may be useful to treat a patient that has failed other therapies. For example, some patients who are treated with Rituxan™ may initially respond, but Rituxan™-resistant cancer cells may arise. Such patients should generally still respond to the antibodies of the invention.

In the case of antibodies directed against CD19, it is sometimes useful to clear the normal B cells from the body, as these cells are likely to titrate the antibody of the invention. Rituxan™ may be used for this purpose, according to standard procedures. Alternatively, the anti-CD 19 antibodies of the invention may be used to clear the normal B cells from the body, for example as described in Example 5 and Example 9.

Infusion is the preferred method of administration. Other methods of administration include injection routes such as subcutaneous, intradermal, intramuscular, intraperitoneal, or intravenous (bolus) delivery. Inhalation and oral delivery are also possible methods of delivery.

For a 70 kilogram human, a typical dose is in the range of about 50 milligrams to 2 grams, with a preferred dose in the range of about 400-600 milligrams. Dosing may be repeated about once every three to six weeks, for example, during which normal B cells and tumor cells are monitored.

Fusion proteins of the present invention are useful in treating human disease, such as cancer. When treating cancer, it is for example useful to administer an antibody-IL-2 fusion protein comprising the variable regions of the invention by infusion or subcutaneous injection, using doses of 0.1 to 100 milligrams/meter$^2$/patient. In a preferred embodiment, it is particularly useful to administer an antibody-IL-2 fusion protein comprising the variable regions of the invention by infusion or subcutaneous injection, using doses of 1 to 10 milligrams/meter$^2$/patient, and more preferably about 3 to 6 milligrams/meter$^2$/patient.

Pharmaceutical compositions of the invention may be used in the form of solid, semisolid, or liquid dosage forms, such as, for example, pills, capsules, powders, liquids, suspensions, or the like, preferably in unit dosage forms suitable for administration of precise dosages. The compositions include a conventional pharmaceutical carrier or excipient and, in addition, may include other medicinal agents, pharmaceutical agents, carriers, adjuvants, etc. Such excipients may include other proteins, such as, for example, human serum albumin or plasma proteins. Actual methods of preparing such dosage forms are known or will be apparent to those skilled in the art. The composition or formulation to be administered will, in any event, contain a quantity of the active component(s) in an amount effective to achieve the desired effect in the subject being treated.

Administration of the compositions hereof can be via any of the accepted modes of administration for agents that exhibit such activity. These methods local or systemic administration. Intravenous injection in a pharmaceutically acceptable carrier is a preferred method of administration. The amount of active compound administered will, of course, be dependent on the subject being treated, the severity of the affliction, the manner of administration, and the judgment of the prescribing physician.

The invention is further illustrated through the following non-limiting examples.

Example 1. Construction of Anti-CD19 Antibodies Containing Variable Region Heavy and Light Chains of the Invention Standard genetic engineering techniques were used to introduce nucleic acid sequences encoding a heavy chain region and light chain region of the invention into an appropriate mammalian expression vector. Exemplary cloning strategies are described below. The expression vector pdHL12 is a later-generation pdHL expression vector engineered to contain unique restriction sites for the insertion of nucleic acid cassettes encoding heavy and light chain variable regions. pdHL12 is designed to accept nucleic acids encoding the heavy chain variable region as a Nhe I/Hind III fragment, and nucleic acids encoding the light chain variable region as an Afl II/Bam HI fragment, and to co-express intact antibody heavy and light chains (see, for example US patent application 2003/0157054).

Nucleic acid sequences of heavy chain variable regions of the invention, flanked by sequences with endonuclease restriction recognition sequences 5'-CTTAAGC-3' (upstream, containing the Nhe I site) and 5'-CGTAAGTGGATCC-3' (downstream, containing the Hind III site), were synthesized de novo and inserted into a pUC vector-derived carrier plasmid (Blue Heron Biotechnology, Bothell, Wash.). The nucleic acid was excised from the carrier plasmid as a Nhe I/Hind III fragment and ligated to the appropriate vector fragment of a likewise digested pdHL12 plasmid. Nucleic acid sequences for B4 VH0 (SEQ ID NO:1), B4 VHv1 (SEQ ID NO:2), B4 VHv2 (SEQ ID NO:3), B4 VHv3 (SEQ ID NO:4), B4 VHv4 (SEQ ID NO:5), B4 VHv5 (SEQ ID NO:6), and B4 VHv6 (SEQ ID NO:7) are shown.

Similarly, nucleic acids of light chain variable regions of the invention, flanked by sequences with endonuclease restriction recognition sequences 5'-GCTAGCTCCAGC-3' (upstream, containing the Afl II site) and 5'-GGTAAGCTT-3' (downstream, containing the Bam HI site), were synthesized de novo and inserted into a pUC vector-derived carrier plasmid (Blue Heron Biotechnology, Bothell, Wash.). The nucleic acid was excised from the carrier plasmid as an Afl II/Bam HI fragment and ligated to the appropriate vector fragment of a likewise digested pdHL12 plasmid. Nucleic acid sequences encoding B4 VK0 (SEQ ID NO:8), B4 VKv1 (SEQ ID NO:9), B4 VKv2 (SEQ ID NO:10), B4 VKv3 (SEQ ID NO: 11), and B4 VKv4 (SEQ ID NO:12) are shown.

By inserting the nucleic acid sequences encoding the different heavy and light chain variable regions combinatorially into pdHL12, a panel of plasmids encoding B4 antibodies of the invention, B4 VHvx/VKvy, were generated.

Example 2. Expression and Purification of Antibodies of the Invention

The following general techniques are used in the subsequent Examples.

1A. Cell Culture and Transfection

To express antibodies transiently from mammalian cells, plasmid DNA is introduced into human embryonic kidney 293 cells, or baby hamster kidney (BHK) cells, by coprecipitation of plasmid DNA with calcium phosphate and cells are grown without selection for plasmid maintenance [Sambrook et al. (1989) Molecular Cloning: A Laboratory Manual, Cold Spring Harbor, N.Y.].

Stably transfected clones are obtained by one of several standard methods, for example, by electroporation or by nucleofection. Electroporation of DNA into mouse myeloma NS/0 cells is performed as follows. NS/O cells are grown in Dulbecco's modified Eagle's medium (DMEM, Life Technologies) supplemented with 10% fetal bovine serum, 2 mM glutamine, 1 mM sodium pyruvate and 1x penicillin/streptomycin. About $5 \times 10^6$ cells are washed once with PBS and resuspended in 0.5 ml phosphate buffer solution (PBS). Ten micrograms of linearized plasmid DNA is then incubated with the cells in a Gene Pulser Cuvette (0.4 cm electrode gap, BioRad) for 10 minutes on ice. Electroporation is performed using a Gene Pulser (BioRad) with settings at 0.25 V and microF. Cells are allowed to recover for 10 minutes on ice, after which they are resuspended in growth medium and then plated onto two 96-well plates. Stably transfected clones are selected by growth in the presence of 100 nM methotrexate (MTX), which is introduced two days post-transfection. The cells are fed every 3 days for two to three more times, and MTX-resistant clones generally appeared in 2 to 3 weeks. Supernatants from clones are assayed by anti-human Fc ELISA to identify high producers [Gillies et al. (1989) J. Immunol. Methods 125:191]. High producing clones are isolated and propagated in growth medium containing 100 nM MTX.

Similarly, other cell lines may be used to obtain stably transfected clones by essentially the same method, such as CHO cells, BHK cells, SP2/0 cells, and YB2/0 cells. When YB2/0 cells were used, stably transfected clones were generally selected by growth in the presence of 50 nM MTX.

Stably transfected clones, for example from rat myeloma YB2/0 cells, were also obtained by nucleofection. About $2 \times 10^6$ YB2/0 cells, grown in Dulbecco's modified Eagle's medium (DMEM) supplemented with heat inactivated 10% fetal bovine serum, 2 mM glutamine, 1 mM sodium pyruvate, and 1×penicillin/streptomycin, were centrifuged at 90×g at room temperature for 10 min and resuspended in 100 µl of supplemented Nucleofector Solution V. 100 µl of the cell suspension was mixed with 2 µg of linearized plasmid DNA (linearized at the Fsp I site in the β-lactamase sequence), transferred into a cuvette (Amaxa), and the nucleofection was performed using the appropriate Nucleofector (Amaxa) program, Q-20. 500 µl pre-warmed culture medium was added and the sample was transferred into a well of a 12-well plate. One day post transfection, the cells were resuspended in growth medium and plated onto 96 well plates at cell densities ranging from approximately 10 cells/well to approximately 600 cells/well. Stably transfected clones were selected by growth in the presence of 50 nM methotrexate (MTX), which was introduced two days post-transfection. The cells were fed every 2 or 3 days twice more, and MTX-resistant clones generally appeared in 2 to 3 weeks. Supernatants from clones were assayed by anti-human Fc ELISA to identify high producers [Gillies et al. (1989) J. Immunol. Methods 125:191]. High producing clones were isolated and propagated in growth medium containing 50 nM MTX.

The cells may be grown in an alternate medium known in the art, such as HSFM supplemented with 2.5% fetal bovine serum and 100 nM methotrexate, or a protein free medium such as CD medium.

1B. ELISAs

Different ELISAs are used to determine the concentrations of protein products in the supernatants of MTX-resistant clones and other test samples. For example, the anti-huFc ELISA is used to measure the amount of human Fc-containing proteins, e.g., chimeric antibodies, and the anti-hu kappa ELISA is used to measure the amount of kappa light chain (of chimeric or human immunoglobulins).

The anti-huFc ELISA is described in detail below.

A. Coating Plates

ELISA plates are coated with AffiniPure goat anti-human IgG (H+L) (Jackson Immuno Research) at 5 microgram/ml in PBS, and 100 µl/well in 96-well plates (Nunc-Immuno plate Maxisorp). Coated plates are covered and incubated at 4° C. overnight. Plates are then washed 4 times with 0.05% Tween (Tween 20) in PBS, and blocked with 1% BSA/1% goat serum in PBS, 200 microliter/well. After incubation with the blocking buffer at 37° C. for 2 hours, the plates are washed 4 times with 0.05% Tween in PBS and tapped dry on paper towels.

B. Incubation with Test Samples and Secondary Antibody

Test samples are diluted to the proper concentrations in sample buffer, which contains 1% BSA/1% goat serum/ 0.05% Tween in PBS. A standard curve is prepared with a chimeric antibody (with a human Fc), the concentration of which is known. To prepare a standard curve, serial dilutions are made in the sample buffer to give a standard curve ranging from 125 ng/ml to 3.9 ng/ml. The diluted samples and standards are added to the plate, 100 microliter/well, and the plate is incubated at 37° C. for 2 hours.

After incubation, the plate is washed 8 times with 0.05% Tween in PBS. To each well is then added 100 microliter of the secondary antibody, the horseradish peroxidase (HRP)-conjugated anti-human IgG (Jackson Immuno Research), diluted around 1:120,000 in the sample buffer. The exact dilution of the secondary antibody has to be determined for each lot of the HRP-conjugated anti-human IgG. After incubation at 37° C. for 2 hours, the plate is washed 8 times with 0.05% Tween in PBS.

C. Development

The substrate solution is added to the plate at 100 μl/well. The substrate solution is prepared by dissolving 30 mg of o-phenylenediamine dihydrochloride (OPD) (1 tablet) into 15 ml of 0.025 M citric acid/0.05M $Na_2HPO_4$ buffer, pH 5, which contains 0.03% of freshly added $H_2O_2$. The color is allowed to develop for 30 minutes at room temperature in the dark. The developing time is subject to change, depending on lot to lot variability of the coated plates, the secondary antibody, etc. The color development in the standard curve is observed to determine when to stop the reaction. The reaction is stopped by adding 4N $H_2SO_4$, 100 μl/well. The plate is read by a plate reader, which is set at both 490 nm and 650 nm and programmed to subtract off the background OD at 650 nm from the OD at 490 nm.

The anti-hu kappa ELISA follows the same procedure as described above, except that the secondary antibody used is horseradish peroxidase-conjugated goat anti-hu kappa (Southern Biotechnology Assoc. Inc., Birmingham, Ala.), used at a 1:4000 dilution.

Purification

Standard antibody purification procedures were followed. Typically, B4 VHvx/VKvy antibody compositions of the invention were purified from cell-culture supernatants via Protein A chromatography based on the affinity of the Fc portion for Protein A. The conditioned supernatant from cells expressing B4 VHvx/VKvy antibody compositions was loaded onto a pre-equilibrated Fast-Flow Protein A Sepharose column. The column was washed extensively with sodium phosphate buffer (50 mM Sodium Phosphate, 150 mM NaCl at neutral pH). Bound protein was eluted by a low pH (pH 2.5-3) sodium phosphate buffer (composition as above) and the eluted fractions were immediately neutralized to about pH 6.5 with 1M Tris base. The compositions were stored in 50 mM Sodium Phosphate, 150 mM NaCl, pH 6.5 supplemented with Tween 80 to 0.01%.

The purity and integrity of the product was routinely assessed by HPLC size exclusion chromatography and by SDS-PAGE. Results showed that the B4 VHvx/VKvy antibodies of the invention were typically greater than 90% non-aggregated and intact, with little evidence of degradation products.

Example 3. Determination of the Relative Binding Affinity of B4 Antibodies of the Invention to CD-19 Presenting Cells To ascertain that the antibodies of the invention retained binding to CD19 a competition assay was used, in which the strength of these antibodies to inhibit binding of labeled parental B4 antibody (B4 VH0/VK0) to Daudi lymphoma cells, which bear the CD19 antigen, was measured.

Biotin-labeled B4 VH0/VK0 antibody was prepared using the EZ-link Sulfo-NHS-LC-Biotinylation Kit (Pierce, #21430) according to the supplied protocol. The product was dialyzed with a Slide-a-lyzer (Pierce, #66425), and analyzed by HPLC size exclusion chromatography.

Briefly, a titration series was prepared of biotin-labeled B4 VH0/VK0 antibody pre-mixed at a final concentration of 100 ng/ml with one of the unlabeled, experimental B4 VHvx/VKvy antibodies at 800 ng/ml, 400 ng/ml, 200 ng/ml, 100 ng/ml, and 50 ng/ml in a PBS/2% serum buffer. As a control, the biotin-labeled antibody was pre-mixed with unlabeled B4 VH0/VK0 antibody at the same concentrations as above (inhibition control) or with buffer only (positive binding control). The combined antibodies were added to Daudi cells for 30 minutes at 4° C. A 1:200 dilution of FITC-labeled streptavidin was added to the cells and the samples were incubated for a further 30 minutes at 4° C. Bound amount of labeled B4 VH0/VK0 antibody was quantitated by FACS analysis, and the results were expressed as "percent inhibition," relative to the positive binding control. The tested antibodies were B4 VH0/VK0 (C), B4 VHv1/ VKv1 (1), B4 VHv2/VKv1 (2), B4 VHv1/VKv2 (3), B4 VHv2/VKv2 (4), B4 VHv3/VKv3 (5), B4 VHv4/VKv3 (6), B4 VHv3/VKv4 (7), B4 VHv4/VKv4 (8), B4 VHv5/VKv4 (9), and B4 VHv6/VKv4 (10). Representative results of two experiments are shown in Table 3 and Table 4.

TABLE 3

Inhibition of Biotin-B4 VH0/VK0 binding to Daudi cells by antibodies of the invention.

| Ratio (unlabeled/labeled) | Antibody (% inhibition of labeled B4 binding) | | | | | | | | |
|---|---|---|---|---|---|---|---|---|---|
| | C | 1 | 2 | 3 | 4 | 5 | 6 | 7 | 8 |
| 8x | 68 | 56 | 56 | 56 | 56 | 60 | 56 | 60 | 60 |
| 4x | 56 | 44 | 40 | 44 | 44 | 40 | 44 | 52 | 48 |
| 2x | 44 | 28 | 28 | 32 | 32 | 36 | 32 | 36 | 32 |
| 1x | 28 | 16 | 16 | 20 | 16 | 20 | 16 | 20 | 16 |
| 0.5x | 16 | 12 | 8 | 12 | 8 | 12 | 12 | 12 | 12 |

TABLE 4

Inhibition of Biotin-B4 VH0/VK0 binding to Daudi cells by antibodies of the invention.

| Ratio (unlabeled/labeled) | Antibody (% inhibition of labeled B4 binding) | | |
|---|---|---|---|
| | C | 9 | 10 |
| 8x | 93 | 90 | 87 |
| 4x | 90 | 87 | 80 |
| 2x | 83 | 70 | 70 |
| 1x | 67 | 57 | 60 |
| 0.5x | 50 | 47 | 53 |

As shown in Table 3 and Table 4, it was found that the B4 VHvx/VKvy antibodies inhibited binding of labeled B4 antibody to Daudi cells to a similar extent as the unlabeled B4 VH0/VK0 antibody did, indicating that the affinities of the B4 VHvx/VKvy antibodies and B4 VH0/VK0 antibody are similar.

Example 4. ADCC Activity of Antibodies of the Invention

ADCC activity mediated by the antibodies of the invention produced in various cell lines was assessed. ADCC was determined by a standard $^{51}$Cr release assay, as practiced in the art. A serial dilution of the antibodies was prepared (4-fold dilutions in a range from 100 ng/ml to 0.025 ng/ml), and lysis by purified human PBMCs (effector cells) of $^{51}$Cr-labeled Daudi cells (target; E:T is 100:1) in the presence of the antibodies was measured by specific $^{51}$Cr release, relative to total cellular $^{51}$Cr (adjusting for spontaneously released $^{51}$Cr). B4 VHv4/VKv4 antibodies produced from human embryonic kidney 293T cells or from YB2/0 cells, and B4 VHv5N/VKv4 antibodies produced from a NS/O cell line or from YB2/0 cells were tested.

FIG. 38 shows the result of such an experiment. Both antibodies obtained from YB2/0 cell expression were equally active in mediating ADCC, and at least 50 fold more active than the corresponding antibody obtained by expression from a NS/IO cell line or from 293T cells. B4 VHv4/VKv4 produced from 293T cells was more active than B4 VHv5/VKv4 produced from a NS/0 cell line.

Example 5. Depletion of Human B Cells Grafted into SCID Mice by Antibodies of the Invention The depletion of B cells is useful in a number of therapeutic contexts. For example, antibody-driven autoimmune and inflammatory disorders may be treated with antibodies of the invention to reduce or essentially eliminate B cells. Alternatively, when treating with a tumor-targeting agent such as Zevalin™ or Bexxar™ or a Leu16-IL2 fusion protein (WO2005/016969), it is useful to first eliminate normal B cells.

To address whether an antibody of the invention could be used to deplete human B cells, the following experiment was performed. On day 0, male SCID CB17 mice (n=3) were engrafted with purified human PBMCs in which about $4.5 \times 10^7$ cells in 0.2 mls of PBS were injected intraperitoneally, essentially following a protocol described for the transfer of human spleen cells (Yacoub-Youssef et al., Transpl. Immunol. (2005) 15:157-164). On day 3, the mice were injected intraperitoneally with either PBS or 50 micrograms of the anti-CD20 antibody Leu16 or with the K4H4 anti-CD19 antibody. Levels of human IgM were measured by a human IgM ELISA quantitation kit (Bethyl Laboratories; Cat #E80-100) on days 7, 14, and 21.

Figure 39:
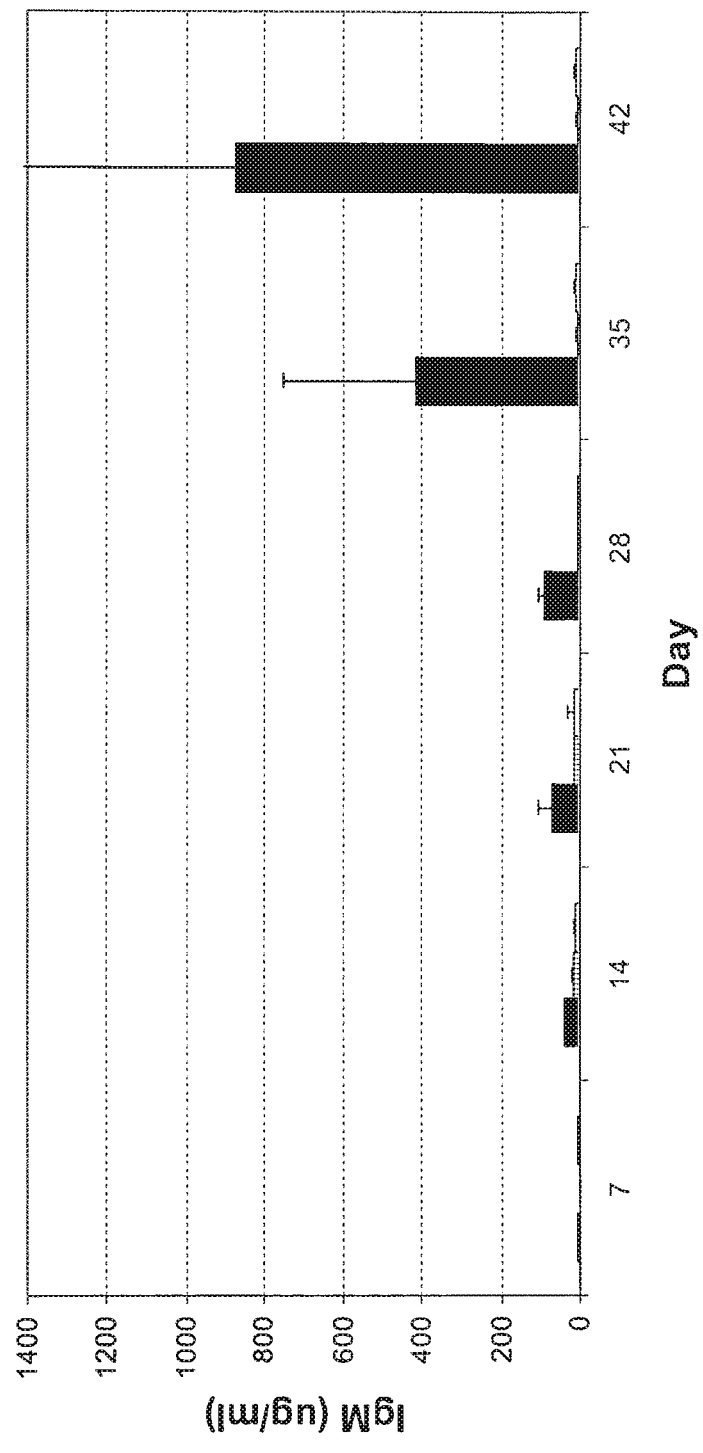
FIG. 39 shows the results of treatment of mice transplanted with human PBMCs treated with either the B4 VHv4/VKv4 antibody of the invention (striped bars), Leu 16 antibody (white bars) or PBS (black bars) as described in Example 5.

FIG. 39 shows typical results. In the PBS-treated controls, the titer of human IgM steadily increased, reaching about 800 micrograms/ml on day 42. In the mice treated with either Leu16 or B4 VHv5/VKv4 antibody, human IgM titers were essentially absent, indicating that human B cells were depleted by these antibody treatments.

Example 6. Treatment of a Lymphoma-Bearing Mammal with an Antibody of the Invention To address whether the antibodies of the invention were functional in vivo, the B4 VHv4/VKv4 antibody, expressed in YB2/0 cells, was tested in an animal model of human lymphoma. Eight-week-old SCID CB17 mice (n=6) were injected intravenously with about $1 \times 10^6$ viable 'Namalwa' Nalm-6-UM-1 cells on day 0. On days 1, 3 and 5, mice were treated with 500 micrograms of antibody intraperitoneally or with PBS. About one to two times per week the mice were examined to see which mice had become ill enough to require euthanasia.

Figure 40:
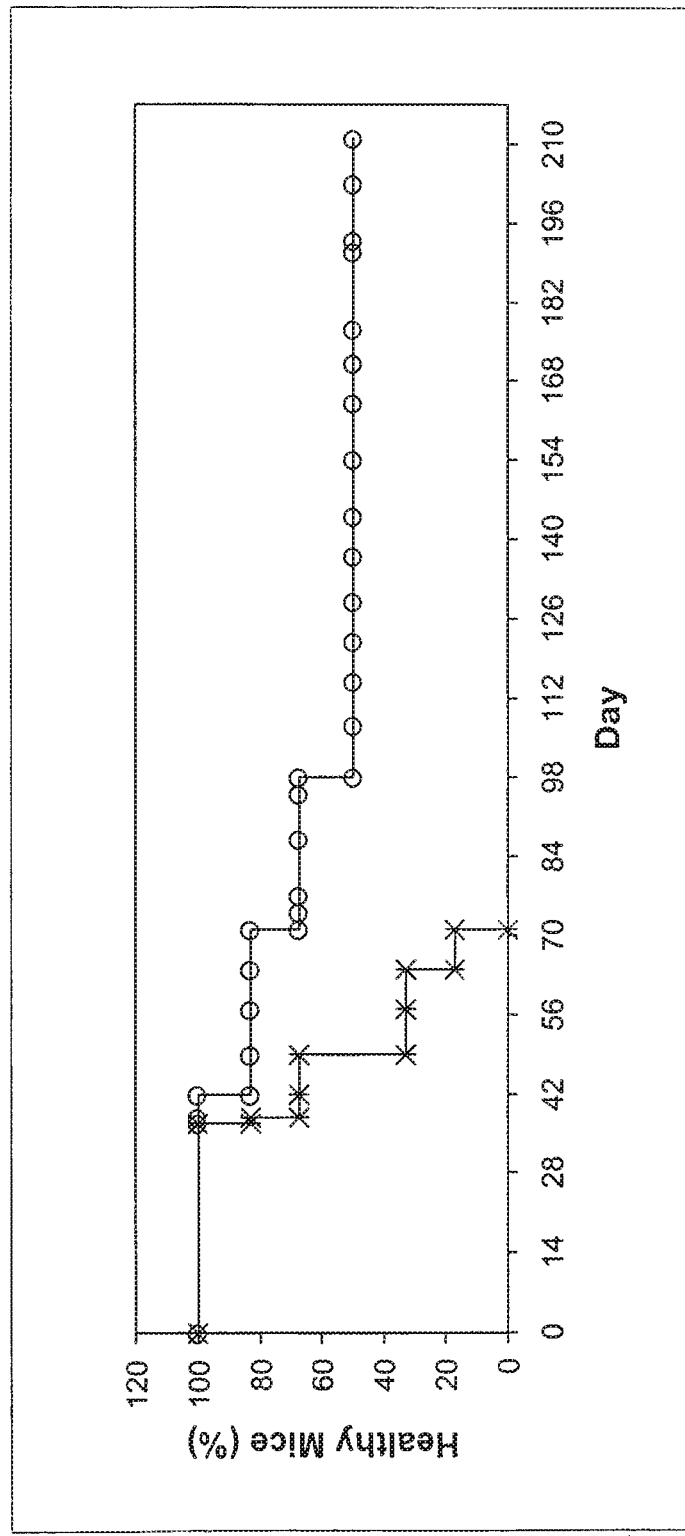
FIG. 40 shows the results of treatment of mice carrying Namalwa lymphoma cells treated with either the B4 VHv4/VKv4 antibody of the invention (empty circles) or PBS (stars) as described in Example 6

FIG. 40 shows typical results of such an experiment. Mice treated with PBS all became ill within 10 weeks of the injection of the tumor cells, while mice treated with the B4 VHv4/VKv4 antibody became ill at later times, and three of the six mice in this group remained healthy throughout the 30-week course of the experiment.

Example 7. Treatment of a Burkitt's Lymphoma-Bearing Mammal with an Antibody of the Invention in Combination with Chemotherapy To address whether the antibodies of the invention could be used in vivo in combination with chemotherapy, the B4 VHv4/VKv4 antibody was tested in animal models of human lymphoma that were more stringent than in the previous example, corresponding to more advanced or harder to treat forms of lymphoma. In one representative experiment, the Daudi cell line, which is a Burkitt's lymphoma cell line, was treated with the B4 VHv4/VKv4 antibody, expressed in YB2/0 cells, with or without cyclophosphamide (CPA). Eight-week-old SCID CB17 mice (n=6) were injected intravenously with about $5 \times 10^6$ viable Daudi cells on day 0. On days 8 and 12, mice were treated with 100 micrograms of antibody or PBS. On day 7, the mice were treated with PBS or 75 micrograms of CPA per kilogram of body weight. Treatments were administered intraperitoneally in 0.2 mls. About one to two times per week the mice were examined to see which mice had become ill enough to require euthanasia.

Figure 41:
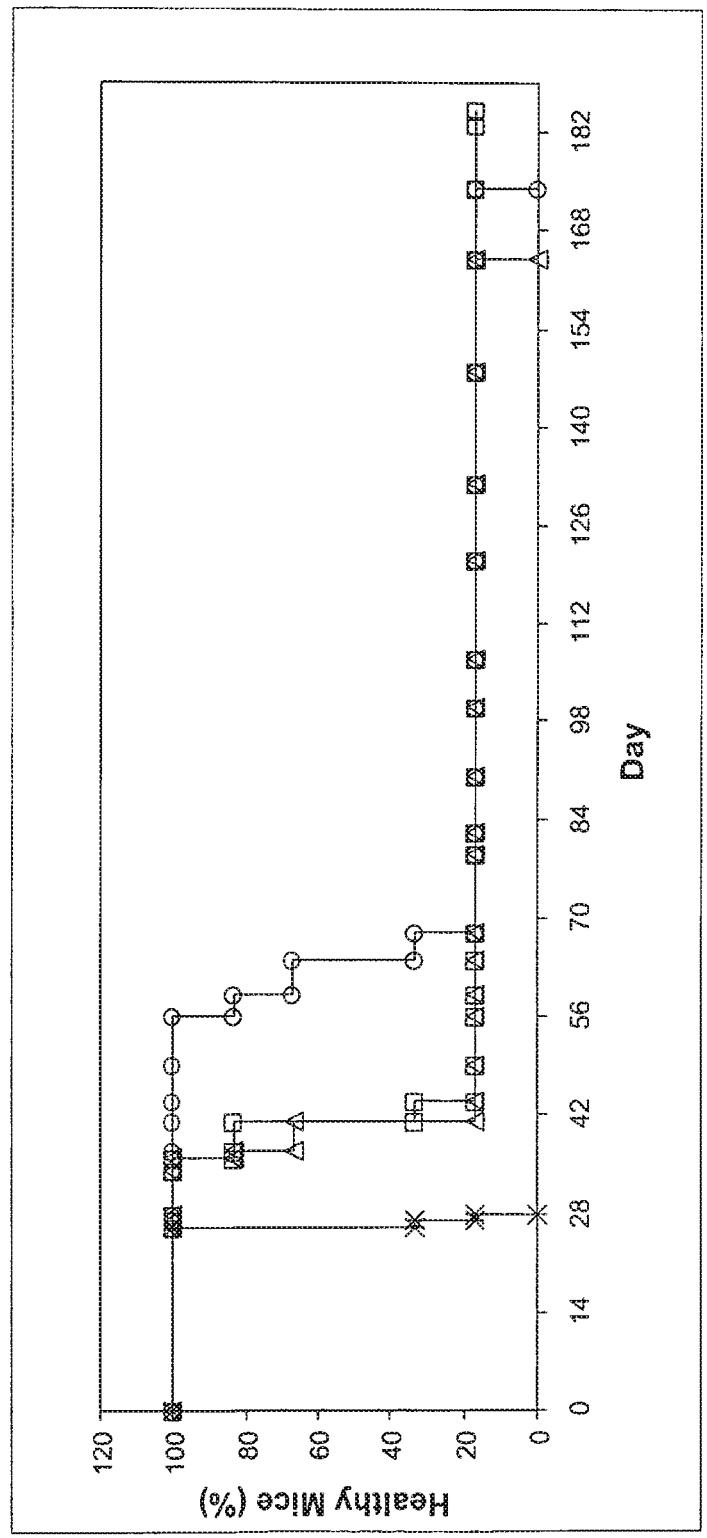
FIG. 41 shows the results of treatment of mice carrying Daudi Burkitt's lymphoma cells treated with either the B4 VHv4/VKv4 antibody of the invention (empty triangles), cyclophosphamide (empty squares), a combination of the B4 VHv4/VKv4 antibody and cyclophosphamide (empty circles), or PBS (stars) as described in Example 7.

FIG. 41 shows the results of a typical experiment. In the control group treated with neither antibody nor CPA, all of the mice became ill within four weeks of injection of the lymphoma cells. In the groups of mice singly treated with either the B4 VHv4/VKv4 antibody or CPA, 5 out of the 6 mice were healthy for at least five weeks but became ill within about six weeks. In the group of mice treated with both B4 VHv4/VKv4 antibody and CPA, all of the mice remained healthy for at least eight weeks.

Figure 42A:
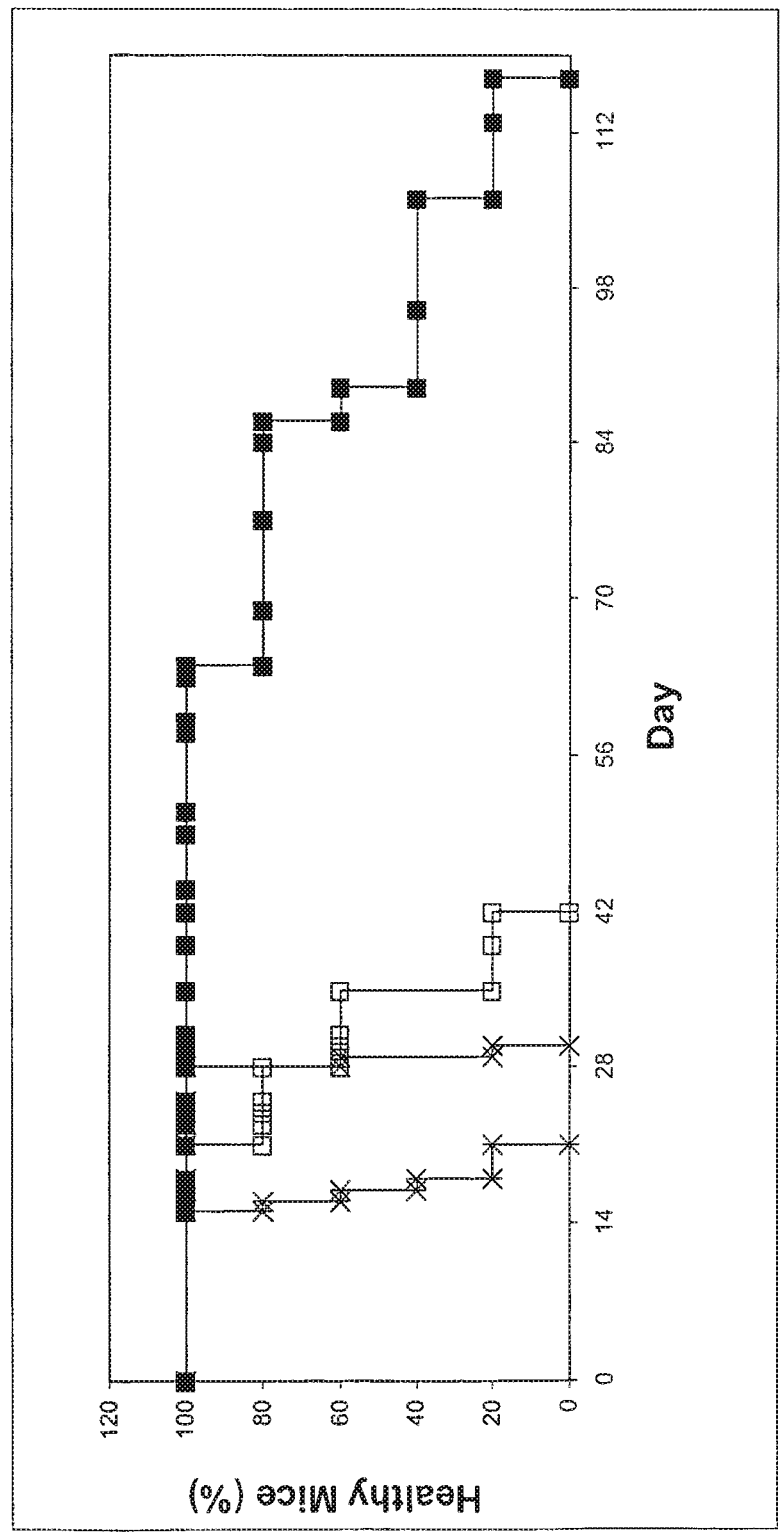
FIGS. 42(a)-(c) show the results of treatment of mice carrying Namalwa lymphoma cells with an antibody of the invention combined with various chemotherapy agents, as described in Example 8.
Figure 42B:
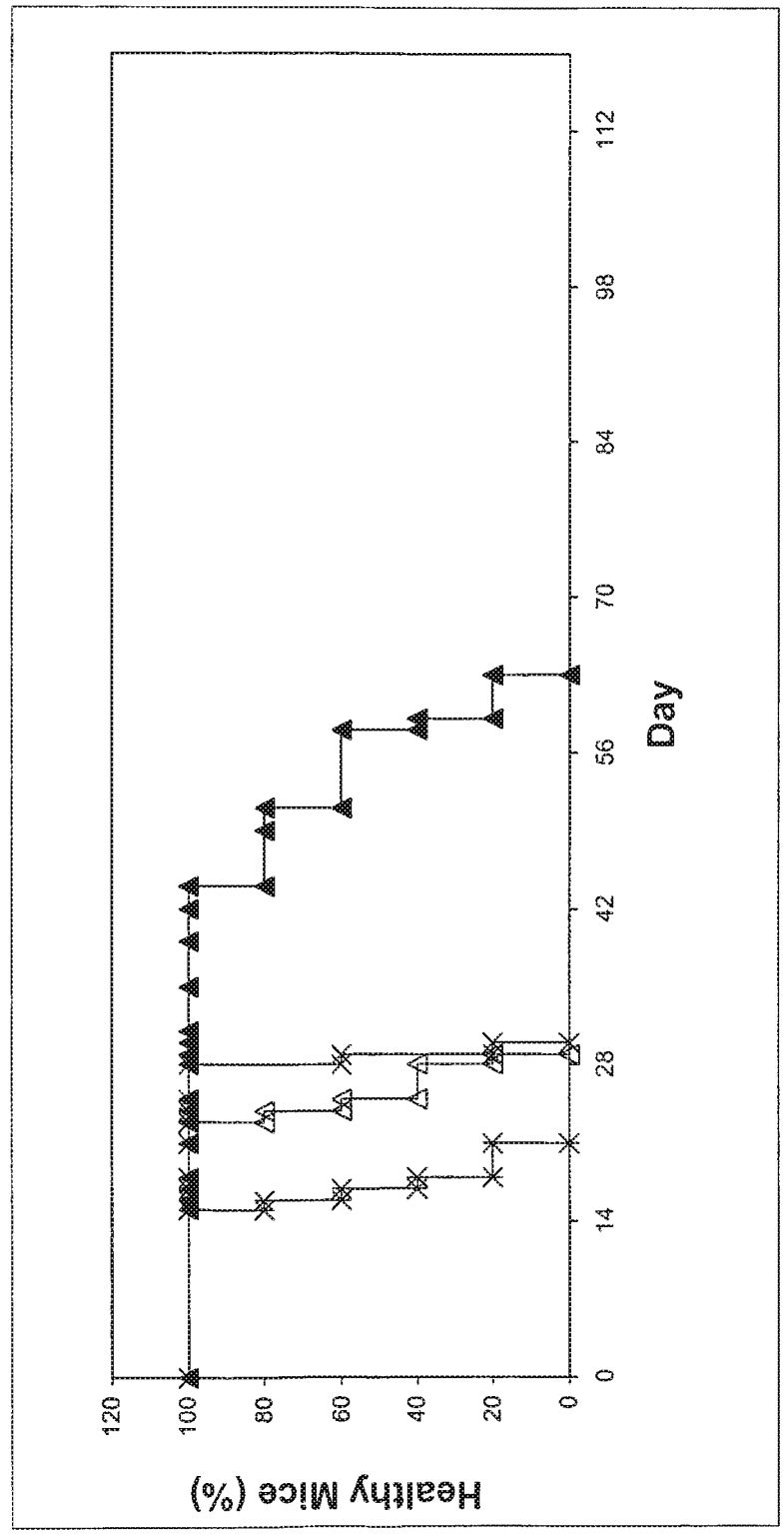
Figure 42C:
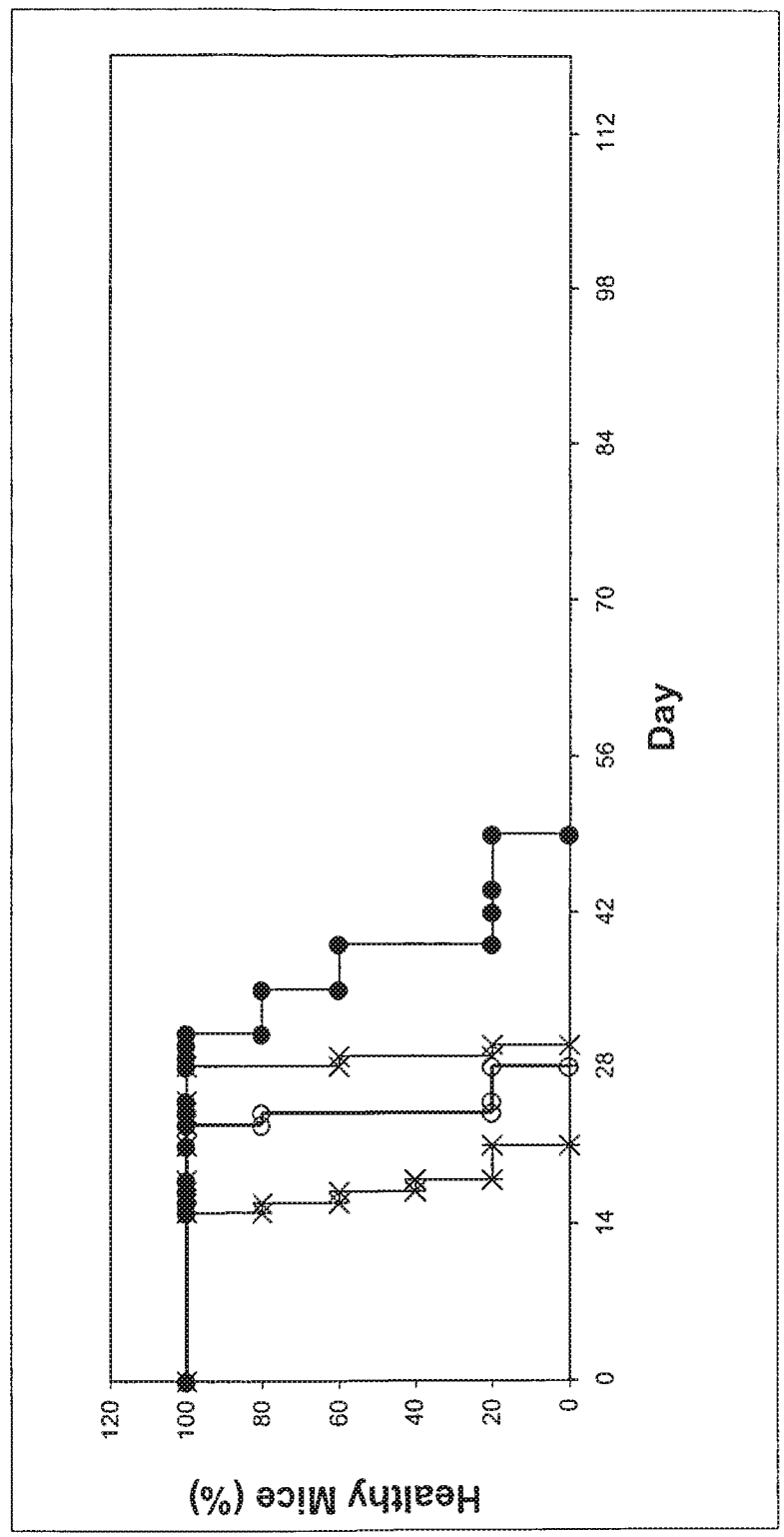

Example 8. Treatment of Lymphoma Disseminated Disease with an Antibody of the Invention Combined with Chemotherapy In another set of experiments, Namalwa cells were injected intravenously into mice as described in the previous Example, except that $2 \times 10^6$ cells were used instead of $1 \times 10^6$ cells. This increased number of cells results in a more aggressive disease course, as indicated by a comparison of the PBS-treated mice in FIG. 42, which all became ill within three weeks, as opposed to the PBS-treated mice in FIG. 40, which became ill between five and 10 weeks. Mice (n=5) were treated with 500 micrograms of antibody intraperitoneally or with PBS on days 3, 7 and 11. Mice were also treated with either cyclophosphamide (75 mg/kg, i.p.), or vincristine (0.4 mg/kg, i.v.) or doxorubicin (3 mg/kg, i.v.) or PBS (i.v.) on days 3, 7, and 11. The results are shown in FIG. 42(a-c). The results indicated that each of the three chemotherapeutic agents could be combined with an antibody of the invention.

Example 9. Treatment of a Human Patient with Antibodies and Methods of the Invention The anti-CD19 antibodies of the invention are used to treat human diseases and disorders as follows. In general, the preferred method of administration is by intravenous infusion or intravenous injection, although subcutaneous injection, inhalation, oral delivery, and other methods are also possible. Administration about once every 2, 3 or 4 weeks is used, although the frequency of administration may vary depending on the needs of the patient. A typical dose is about 100 to 800 mgs for an adult human. Treated patients are monitored for signs of infection that may result from immunosuppression.

For example, a patient with Castleman's disease is treated with the anti-CD19 B4 VHv4/VKv4 antibody of the invention about once every two weeks at a dose of about 8 mg/kg, with administration by drip infusion for about 1 hour.

A patient with rheumatoid arthritis is treated with the anti-CD19 B4 VHv4/VKv4 antibody about once every four weeks at a dose of about 8 mg/kg, with administration by drip infusion for about 1 hour. Progression of joint destruction is found to be significantly inhibited by monotherapy, even when compared to disease-modifying anti-rheumatic drugs.

A patient with Crohn's disease is treated with the anti-CD19 B4 VHv4/VKv4 antibody about once every four weeks at a dose of about 8 mg/kg, with administration by drip infusion for about 1 hour.

A patient with multiple myeloma is treated with the anti-CD19 B4 VHv4/VKv4 antibody about once every three weeks at a dose of about 8 mg/kg, with administration by drip infusion for about 1 hour. Treatment with the anti-CD19 B4 VHv4/VKv4 is combined with a standard-of-care treatment for multiple myeloma as determined by a physician as appropriate for the patient.

A patient with a B cell lymphoma is treated with the anti-CD19 B4 VHv4/VKv4 antibody about once every three weeks at a dose of about 8 mg/kg, with administration by drip infusion for about 1 hour, optionally in combination with an antibody such as Rituxan™ at about 375 milligrams per square meter of body surface area, which is administered every week, or with the anti-CD22 antibody epratuzumab. Alternatively, in the case of a patient with refractory lymphoma, treatment with the anti-CD19 B4 VHv4/VKv4 antibody is combined with a radioimmunoconjugate such as Bexxar™ or Zevalin™.

More specifically, a patient with a B cell lymphoma is treated with the anti-CD19 B4 VHv4/VKv4 antibody about once every three weeks at a dose of about 8 mg/kg, with administration by drip infusion for about 1 hour, optionally in combination with a chemotherapeutic regimen such as cyclophosphamide plus vincristine plus doxorubicin plus prednisolone ("CHOP"), or CHOP plus bleomycin, or CHOP plus etoposide, or mitoxantrone plus vincristine plus thiotepa, or etoposide plus prednisolone plus cytarabin plus cisplatin, or mesna plus ifosfamide plus mitoxantrone plus etoposide, or bendamustin, or fludaribin and 2-CdA.

In an alternative treatment strategy, a patient with a B cell lymphoma is initially treated with the anti-CD19 B4 VHv4/VKv4 antibody at a dose of about 8 mg/kg, and is then later treated with an anti-CD20-IL2 fusion protein such as that described in WO2005/016969. For example, a patient is treated on day 1 with the anti-CD 9 B4 VHv4/VKv4 antibody with administration by drip infusion for about 1 hour, and then treated on day 2 and day 4 with an anti-CD20-IL2 fusion protein at a dose of about 150 micrograms per kg with administration by drip infusion for about 4 hours, and this cycle is repeated about every 3 weeks. Without wishing to be bound by theory, the anti-CD19 B4 VHv4/VKv4 antibody has the effect of clearing most of the normal B cells from the patient, so that the anti-CD20-1L2 fusion protein exerts its effects by binding to remaining tumor cells.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

What is claimed is:

1. A pharmaceutical composition comprising:
   i) in a pharmacologically effective amount an anti-CD19 antibody or polypeptide comprising:
   (a) a heavy chain variable region that is at least 95% identical to SEQ ID NO: 13; and
   (b) a light chain variable region that is at least 95% identical to SEQ ID NO: 25; and
   ii) a pharmaceutically acceptable diluent, carrier, or excipient.

* * * * *

SEQUENCE LISTING

<160> NUMBER OF SEQ ID NOS: 49

<210> SEQ ID NO 1
<211> LENGTH: 360
<212> TYPE: DNA
<213> ORGANISM: Homo sapiens

<400> SEQUENCE: 1

```
caggtgcaac tgcagcagcc tggggctgaa gtggtgaagc ctggggcttc agtgagactg      60
tcctgcaaga cttctggcta caccttcacc agcaactgga tgcactgggt gaagcagagg     120
cctggacaag gccttgagtg gatcggagag attgatcctt ctgatagtta tactaactac     180
aatcaaaagt tcaagggcaa ggccaagttg actgtagaca atcctccag cacagcctac      240 atggaagtca gcagcctgac atctgaggac tctgcggtct attactgtgc aagaggtagc     300
aacccttact actatgctat ggactactgg ggtcaaggaa cctcagtcac cgtctcctca     360
```

<210> SEQ ID NO 2
<211> LENGTH: 360
<212> TYPE: DNA
<213> ORGANISM: Artificial Sequence
<220> FEATURE:
<223> OTHER INFORMATION: Nucleic acid sequence encoding B4 antibody
heavy chain variable region with codons for amino acid
substitutions K23E, G42D, K69E, and S85D (B4 VHv1)

<400> SEQUENCE: 2

```
caggtgcaac tgcagcagcc tggggctgaa gtggtgaagc tggggcttc agtgagactg    60 tcctgcgaga cttctggcta ccttcacc agcaactgga tgcactgggt gaagcagagg    120
cctgaccaag gacttgagtg gatcggagag attgatcctt ctgatagtta tactaactac    180
aatcaaaagt tcaagggcaa ggccgaattg actgtagaca atcctccag cacagcctac    240 atggaagtca gcgacctgac atctgaggac tctgcggtct attactgtgc aagaggtagc    300 aaccccttact actatgctat ggactactgg ggtcaaggaa cctcagtcac cgtctcctca    360
```

<210> SEQ ID NO 3
<211> LENGTH: 360
<212> TYPE: DNA
<213> ORGANISM: Artificial Sequence
<220> FEATURE:
<223> OTHER INFORMATION: Nucleic acid sequence encoding B4 antibody
heavy chain variable region with codons for amino acid
substitutions K69E, and S85D (B4 VHv2)

<400> SEQUENCE: 3

```
caggtgcaac tgcagcagcc tggggctgaa gtggtgaagc tggggcttc agtgagactg    60 tcctgcaaga cttctggcta ccttcacc agcaactgga tgcactgggt gaagcagaga    120
cctggacaag gacttgagtg gatcggagag attgatcctt ctgatagtta tactaactac    180
aatcaaaagt tcaagggcaa ggccgaattg actgtagaca atcctccag cacagcctac    240 atggaagtca gcgacctgac atctgaggac tctgcggtct attactgtgc aagaggtagc    300 aaccccttact actatgctat ggactactgg ggtcaaggaa cctcagtcac cgtctcctca    360
```

<210> SEQ ID NO 4
<211> LENGTH: 360
<212> TYPE: DNA
<213> ORGANISM: Artificial Sequence
<220> FEATURE:
<223> OTHER INFORMATION: Nucleic acid sequence encoding B4 antibody
heavy chain variable region with codons for amino acid
substitutions Q5E, V12K, R19K, L20V, T24A, S85D, and S88A (B4
VHv3)

<400> SEQUENCE: 4

```
caggtgcaac tggagcagcc tggggctgaa gtgaagaagc tggggcttc agtgaaggtg    60 tcctgcaagg cttctggcta ccttcacc agcaactgga tgcactgggt gaagcagagg    120
cctggacaag gacttgagtg gatcggagag attgatcctt ctgatagtta tactaactac    180
aatcaaaagt tcaagggcaa ggccaagttg actgtagaca atcctccag cacagcctac    240 atggaagtca gcgacctgac agctgaggac tctgcggtct attactgtgc aagaggtagc    300 aaccccttact actatgctat ggactactgg ggtcaaggaa cctcagtcac cgtctcctca    360
```

<210> SEQ ID NO 5
<211> LENGTH: 360
<212> TYPE: DNA
<213> ORGANISM: Artificial Sequence
<220> FEATURE:
<223> OTHER INFORMATION: Nucleic acid sequence encoding B4 antibody
heavy chain variable region with codons for amino acid
substitutions Q5E, R19K, L20V, R40T, Q43K, K65D, S85D, S88A, and
V93T (B4 VHv4)

<400> SEQUENCE: 5

```
caggtgcaac tggagcagcc tggggctgaa gtggtgaagc ctggggcttc agtgaaggtg    60
tcctgcaaga cttctggcta caccttcacc agcaactgga tgcactgggt gaagcagacg   120
cctggaaaag gacttgagtg gatcggagag attgatcctt ctgatagtta tactaactac   180
aatcaaaagt tcgatggcaa ggccaagttg actgtagaca atcctccag cacagcctac    240
atggaagtca gcgacctgac agctgaggac tctgcgacct attactgtgc aagaggtagc   300
aacccttact actatgctat ggactactgg ggtcaaggaa cctcagtcac cgtctcctca   360
```

<210> SEQ ID NO 6
<211> LENGTH: 360
<212> TYPE: DNA
<213> ORGANISM: Artificial Sequence
<220> FEATURE:
<223> OTHER INFORMATION: Nucleic acid sequence encoding B4 antibody
heavy chain variable region with codons for amino acid
substitutions Q5E, V12K, R19K, L20V, T24A, K38R, R40A, Q43K, K65D,
S85D, and V93T (B4 VHv5)

<400> SEQUENCE: 6

```
caggtgcaac tggagcagcc tggggctgaa gtgaagaagc ctggggcttc agtgaaggtg    60
tcctgcaagg cttctggcta caccttcacc agcaactgga tgcactgggt gagacaggca   120
cctggaaaag gacttgagtg gatcggagag attgatcctt ctgatagtta tactaactac   180
aatcaaaagt tcgatggcaa ggccaagttg actgtagaca atcctccag cacagcctac    240
atggaagtca gcgacctgac atctgaggac tctgcgacct attactgtgc aagaggtagc   300
aacccttact actatgctat ggactactgg ggtcaaggaa cctcagtcac cgtctcctca   360
```

<210> SEQ ID NO 7
<211> LENGTH: 360
<212> TYPE: DNA
<213> ORGANISM: Artificial Sequence
<220> FEATURE:
<223> OTHER INFORMATION: Nucleic acid sequence encoding B4 antibody
heavy chain variable region with codons for amino acid
substitutions Q5E, R19K, L20V, K65D, S85D, and V93T (B4 VHv6)

<400> SEQUENCE: 7

```
caggtgcaac tggagcagcc tggggctgaa gtggtgaagc ctggggcttc agtgaaggtg    60
tcctgcaaga cttctggcta caccttcacc agcaactgga tgcactgggt gaagcagagg   120
cctggacaag gacttgagtg gatcggagag attgatcctt ctgatagtta tactaactac   180
aatcaaaagt tcgatggcaa ggccaagttg actgtagaca atcctccag cacagcctac    240
atggaagtca gcgacctgac atctgaggac tctgcgacct attactgtgc aagaggtagc   300
aacccttact actatgctat ggactactgg ggtcaaggaa cctcagtcac cgtctcctca   360
```

<210> SEQ ID NO 8
<211> LENGTH: 312
<212> TYPE: DNA
<213> ORGANISM: Homo sapiens

<400> SEQUENCE: 8

```
caaattgttc tcacccagtc tccagcaatc atgtctgcat ctccagggga gaaggtcacc    60
atgacctgca gtgccagctc aggtgtcaac tacatgcact ggtaccagca gaagccaggc   120
acctccccca aaagatggat ttatgacaca tccaaactgg cttctggagt ccctgctcgc   180
ttcagtggca gtgggtctgg gacctcttat tctctcacaa tcagcagcat ggaggctgaa   240
```

```
gatgctgcca cttattactg ccatcagcga ggtagttaca cgttcggagg ggggaccaag    300
ctggaaataa aa                                                        312
```

<210> SEQ ID NO 9
<211> LENGTH: 312
<212> TYPE: DNA
<213> ORGANISM: Artificial Sequence
<220> FEATURE:
<223> OTHER INFORMATION: Nucleic acid sequence encoding B4 antibody
      light chain variable region with codons for amino acid
      substitutions V3A, S7E, and A54D (B4 VKv1)

<400> SEQUENCE: 9

```
caaattgctc tcacccagga gccagcaatc atgtctgcat ctccagggga gaaggtcacc     60
atgacctgca gtgccagctc aggtgtcaac tacatgcact ggtatcagca gaagccaggc    120
acctccccca aaagatggat ttatgacaca tccaaactgg attctggagt ccctgctcgc    180
ttcagtggca gtgggtctgg gacctcttat tctctcacaa tcagcagcat ggaggctgaa    240
gatgctgcca cttattactg ccatcagcga ggtagttaca cgttcggagg ggggaccaag    300
ctggaaataa aa                                                        312
```

<210> SEQ ID NO 10
<211> LENGTH: 312
<212> TYPE: DNA
<213> ORGANISM: Artificial Sequence
<220> FEATURE:
<223> OTHER INFORMATION: Nucleic acid sequence encoding B4 antibody
      light chain variable region with codons for amino acid
      substitutions Q1D, I10T, M11L, and A54D (B4 VKv2)

<400> SEQUENCE: 10

```
gacattgttc tcacccagtc tccagcaact ttgtctgcat ctccagggga gaaggtcacc     60
atgacctgta gtgccagctc aggtgtcaac tacatgcact ggtatcagca gaagccaggc    120
acctccccca aaagatggat ttatgacaca tccaaactgg attctggagt ccctgctcgc    180
ttcagtggca gtgggtctgg gacctcttat tctctcacaa tcagcagcat ggaggctgaa    240
gatgctgcca cttattactg ccatcagcga ggtagttaca cgttcggagg ggggaccaag    300
ctggaaataa aa                                                        312
```

<210> SEQ ID NO 11
<211> LENGTH: 312
<212> TYPE: DNA
<213> ORGANISM: Artificial Sequence
<220> FEATURE:
<223> OTHER INFORMATION: Nucleic acid sequence encoding B4 antibody
      light chain variable region with codons for amino acid
      substitutions I10T, M11L, V19A, V29A, and S75E (B4 VKv3)

<400> SEQUENCE: 11

```
caaattgttc tcacccagtc tccagcaact ttgtctgcat ctccagggga gaaggctacc     60
atgacctgca gtgccagctc aggtgctaac tacatgcact ggtaccagca gaagccaggc    120
acctccccca aaagatggat ttatgacaca tccaaactgg cttctggagt ccctgctcgc    180
ttcagtggca gtgggtctgg gacctcttat tctctcacaa tcgagagcat ggaggctgaa    240
gatgctgcca cttattactg ccatcagcga ggtagttaca cgttcggagg ggggaccaag    300
ctggaaataa aa                                                        312
```

<210> SEQ ID NO 12
<211> LENGTH: 312

<212> TYPE: DNA
<213> ORGANISM: Artificial Sequence
<220> FEATURE:
<223> OTHER INFORMATION: Nucleic acid sequence encoding B4 antibody
      light chain variable region with codons for amino acid
      substitutions I10T, M11L, V19A, S51D, and L53T (B4 VKv4)

<400> SEQUENCE: 12

```
caaattgttc tcacccagtc tccagcaact ttgtctgcat ctccagggga gaaggctacc    60
atgacctgta gtgccagctc aggtgtcaac tacatgcact ggtaccagca gaagccaggc   120
acctccccca aaagatggat ttatgacaca gacaaaacgg cttctggagt ccctgctcgc   180
ttcagtggca gtgggtctgg gacctcttat tctctcacaa tcagcagcat ggaggctgaa   240
gatgctgcca ttattactg ccatcagcga ggtagttaca cgttcggagg ggggaccaag   300
ctggaaataa aa                                                      312
```

<210> SEQ ID NO 13
<211> LENGTH: 120
<212> TYPE: PRT
<213> ORGANISM: Homo sapiens

<400> SEQUENCE: 13

Gln Val Gln Leu Gln Gln Pro Gly Ala Glu Val Val Lys Pro Gly Ala
1               5                   10                  15

Ser Val Arg Leu Ser Cys Lys Thr Ser Gly Tyr Thr Phe Thr Ser Asn
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Lys Leu Thr Val Asp Lys Ser Ser Thr Ala Tyr
65                  70                  75                  80

Met Glu Val Ser Ser Leu Thr Ser Glu Asp Ser Ala Val Tyr Tyr Cys
                85                  90                  95

Ala Arg Gly Ser Asn Pro Tyr Tyr Tyr Ala Met Asp Tyr Trp Gly Gln
            100                 105                 110

Gly Thr Ser Val Thr Val Ser Ser
        115                 120

<210> SEQ ID NO 14
<211> LENGTH: 120
<212> TYPE: PRT
<213> ORGANISM: Artificial Sequence
<220> FEATURE:
<223> OTHER INFORMATION: Amino acid sequence of B4 antibody heavy chain
      variable region with codons for amino acid substitutions K23E,
      G42D, K69E, and S85D (B4 VHv1)

<400> SEQUENCE: 14

Gln Val Gln Leu Gln Gln Pro Gly Ala Glu Val Val Lys Pro Gly Ala
1               5                   10                  15

Ser Val Arg Leu Ser Cys Glu Thr Ser Gly Tyr Thr Phe Thr Ser Asn
            20                  25                  30

Trp Met His Trp Val Lys Gln Arg Pro Asp Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Glu Leu Thr Val Asp Lys Ser Ser Thr Ala Tyr
65                  70                  75                  80

```
Met Glu Val Ser Asp Leu Thr Ser Glu Asp Ser Ala Val Tyr Tyr Cys
            85                  90                  95

Ala Arg Gly Ser Asn Pro Tyr Tyr Ala Met Asp Tyr Trp Gly Gln
            100                 105                 110

Gly Thr Ser Val Thr Val Ser Ser
        115                 120

<210> SEQ ID NO 15
<211> LENGTH: 120
<212> TYPE: PRT
<213> ORGANISM: Artificial Sequence
<220> FEATURE:
<223> OTHER INFORMATION: Amino acid sequence of B4 antibody heavy chain
      variable region with codons for amino acid substitutions K69E, and
      S85D (B4 VHv2)

<400> SEQUENCE: 15

Gln Val Gln Leu Gln Gln Pro Gly Ala Glu Val Val Lys Pro Gly Ala
1               5                   10                  15

Ser Val Arg Leu Ser Cys Lys Thr Ser Gly Tyr Thr Phe Thr Ser Asn
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Glu Leu Thr Val Asp Lys Ser Ser Ser Thr Ala Tyr
65                  70                  75                  80

Met Glu Val Ser Asp Leu Thr Ser Glu Asp Ser Ala Val Tyr Tyr Cys
            85                  90                  95

Ala Arg Gly Ser Asn Pro Tyr Tyr Ala Met Asp Tyr Trp Gly Gln
            100                 105                 110

Gly Thr Ser Val Thr Val Ser Ser
        115                 120

<210> SEQ ID NO 16
<211> LENGTH: 120
<212> TYPE: PRT
<213> ORGANISM: Artificial Sequence
<220> FEATURE:
<223> OTHER INFORMATION: Amino acid sequence of B4 antibody heavy chain
      variable region with codons for amino acid substitutions Q5E,
      V12K, R19K, L20V, T24A, S85D, and S88A (B4 VHv3)

<400> SEQUENCE: 16

Gln Val Gln Leu Glu Gln Pro Gly Ala Glu Val Lys Lys Pro Gly Ala
1               5                   10                  15

Ser Val Lys Val Ser Cys Lys Ala Ser Gly Tyr Thr Phe Thr Ser Asn
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Lys Leu Thr Val Asp Lys Ser Ser Ser Thr Ala Tyr
65                  70                  75                  80

Met Glu Val Ser Asp Leu Thr Ala Glu Asp Ser Ala Val Tyr Tyr Cys
            85                  90                  95

Ala Arg Gly Ser Asn Pro Tyr Tyr Ala Met Asp Tyr Trp Gly Gln
            100                 105                 110
```

-continued

```
Gly Thr Ser Val Thr Val Ser Ser
        115                 120
```

<210> SEQ ID NO 17
<211> LENGTH: 120
<212> TYPE: PRT
<213> ORGANISM: Artificial Sequence
<220> FEATURE:
<223> OTHER INFORMATION: Amino acid sequence of B4 antibody heavy chain
      variable region with codons for amino acid substitutions Q5E,
      R19K, L20V, R40T, Q43K, K65D, S85D, S88A, and V93T (B4 VHv4)

<400> SEQUENCE: 17

```
Gln Val Gln Leu Glu Gln Pro Gly Ala Glu Val Val Lys Pro Gly Ala
1               5                   10                  15

Ser Val Lys Val Ser Cys Lys Thr Ser Gly Tyr Thr Phe Thr Ser Asn
            20                  25                  30

Trp Met His Trp Val Lys Gln Thr Pro Gly Lys Gly Leu Glu Trp Ile
        35                  40                  45

Gly Glu Ile Asp Pro Ser Asp Ser Tyr Thr Asn Tyr Asn Gln Lys Phe
    50                  55                  60

Asp Gly Lys Ala Lys Leu Thr Val Asp Lys Ser Ser Ser Thr Ala Tyr
65                  70                  75                  80

Met Glu Val Ser Asp Leu Thr Ala Glu Asp Ser Ala Thr Tyr Tyr Cys
                85                  90                  95

Ala Arg Gly Ser Asn Pro Tyr Tyr Tyr Ala Met Asp Tyr Trp Gly Gln
            100                 105                 110

Gly Thr Ser Val Thr Val Ser Ser
        115                 120
```

<210> SEQ ID NO 18
<211> LENGTH: 120
<212> TYPE: PRT
<213> ORGANISM: Artificial Sequence
<220> FEATURE:
<223> OTHER INFORMATION: Amino acid sequence of B4 antibody heavy chain
      variable region with codons for amino acid substitutions Q5E,
      V12K, R19K, L20V, T24A, K38R, R40A, Q43K, K65D, S85D, and V93T (B4
      VHv5)

<400> SEQUENCE: 18

```
Gln Val Gln Leu Glu Gln Pro Gly Ala Glu Val Lys Lys Pro Gly Ala
1               5                   10                  15

Ser Val Lys Val Ser Cys Lys Ala Ser Gly Tyr Thr Phe Thr Ser Asn
            20                  25                  30

Trp Met His Trp Val Arg Gln Ala Pro Gly Lys Gly Leu Glu Trp Ile
        35                  40                  45

Gly Glu Ile Asp Pro Ser Asp Ser Tyr Thr Asn Tyr Asn Gln Lys Phe
    50                  55                  60

Asp Gly Lys Ala Lys Leu Thr Val Asp Lys Ser Ser Ser Thr Ala Tyr
65                  70                  75                  80

Met Glu Val Ser Asp Leu Thr Ser Glu Asp Ser Ala Thr Tyr Tyr Cys
                85                  90                  95

Ala Arg Gly Ser Asn Pro Tyr Tyr Tyr Ala Met Asp Tyr Trp Gly Gln
            100                 105                 110

Gly Thr Ser Val Thr Val Ser Ser
        115                 120
```

<210> SEQ ID NO 19
<211> LENGTH: 120

```
<212> TYPE: PRT
<213> ORGANISM: Artificial Sequence
<220> FEATURE:
<223> OTHER INFORMATION: Amino acid sequence of B4 antibody heavy chain
      variable region with codons for amino acid substitutions Q5E,
      R19K, L20V, K65D, S85D, and V93T (B4 VHv6)

<400> SEQUENCE: 19
```

| | | | | | | | | | | | | | | |
|---|---|---|---|---|---|---|---|---|---|---|---|---|---|---|
| Gln | Val | Gln | Leu | Glu | Gln | Pro | Gly | Ala | Glu | Val | Val | Lys | Pro | Gly | Ala |
| 1 | | | | 5 | | | | | 10 | | | | | 15 | |
| Ser | Val | Lys | Val | Ser | Cys | Lys | Thr | Ser | Gly | Tyr | Thr | Phe | Thr | Ser | Asn |
| | | | 20 | | | | | 25 | | | | | 30 | | |
| Trp | Met | His | Trp | Val | Lys | Gln | Arg | Pro | Gly | Gln | Gly | Leu | Glu | Trp | Ile |
| | | 35 | | | | | 40 | | | | | 45 | | | |
| Gly | Glu | Ile | Asp | Pro | Ser | Asp | Ser | Tyr | Thr | Asn | Tyr | Asn | Gln | Lys | Phe |
| | 50 | | | | | 55 | | | | | 60 | | | | |
| Asp | Gly | Lys | Ala | Lys | Leu | Thr | Val | Asp | Lys | Ser | Ser | Ser | Thr | Ala | Tyr |
| 65 | | | | | 70 | | | | | 75 | | | | | 80 |
| Met | Glu | Val | Ser | Asp | Leu | Thr | Ser | Glu | Asp | Ser | Ala | Thr | Tyr | Tyr | Cys |
| | | | | 85 | | | | | 90 | | | | | 95 | |
| Ala | Arg | Gly | Ser | Asn | Pro | Tyr | Tyr | Tyr | Ala | Met | Asp | Tyr | Trp | Gly | Gln |
| | | | 100 | | | | | 105 | | | | | 110 | | |
| Gly | Thr | Ser | Val | Thr | Val | Ser | Ser | | | | | | | | |
| | | 115 | | | | | 120 | | | | | | | | |

```
<210> SEQ ID NO 20
<211> LENGTH: 120
<212> TYPE: PRT
<213> ORGANISM: Artificial Sequence
<220> FEATURE:
<223> OTHER INFORMATION: Amino acid sequence of B4 antibody heavy chain
      variable region with codons for amino acid substitutions V12K,
      K23E, G42D, K65D, K69E, and S85D (B4 VHv11)

<400> SEQUENCE: 20
```

| | | | | | | | | | | | | | | | |
|---|---|---|---|---|---|---|---|---|---|---|---|---|---|---|---|
| Gln | Val | Gln | Leu | Gln | Gln | Pro | Gly | Ala | Glu | Val | Lys | Lys | Pro | Gly | Ala |
| 1 | | | | 5 | | | | | 10 | | | | | 15 | |
| Ser | Val | Arg | Leu | Ser | Cys | Glu | Thr | Ser | Gly | Tyr | Thr | Phe | Thr | Ser | Asn |
| | | | 20 | | | | | 25 | | | | | 30 | | |
| Trp | Met | His | Trp | Val | Lys | Gln | Arg | Pro | Asp | Gln | Gly | Leu | Glu | Trp | Ile |
| | | 35 | | | | | 40 | | | | | 45 | | | |
| Gly | Glu | Ile | Asp | Pro | Ser | Asp | Ser | Tyr | Thr | Asn | Tyr | Asn | Gln | Lys | Phe |
| | 50 | | | | | 55 | | | | | 60 | | | | |
| Asp | Gly | Lys | Ala | Glu | Leu | Thr | Val | Asp | Lys | Ser | Ser | Ser | Thr | Ala | Tyr |
| 65 | | | | | 70 | | | | | 75 | | | | | 80 |
| Met | Glu | Val | Ser | Asp | Leu | Thr | Ser | Glu | Asp | Ser | Ala | Val | Tyr | Tyr | Cys |
| | | | | 85 | | | | | 90 | | | | | 95 | |
| Ala | Arg | Gly | Ser | Asn | Pro | Tyr | Tyr | Tyr | Ala | Met | Asp | Tyr | Trp | Gly | Gln |
| | | | 100 | | | | | 105 | | | | | 110 | | |
| Gly | Thr | Ser | Val | Thr | Val | Ser | Ser | | | | | | | | |
| | | 115 | | | | | 120 | | | | | | | | |

```
<210> SEQ ID NO 21
<211> LENGTH: 120
<212> TYPE: PRT
<213> ORGANISM: Artificial Sequence
<220> FEATURE:
<223> OTHER INFORMATION: Amino acid sequence of B4 antibody heavy chain
      variable region with codons for amino acid substitutions Q5E,
      V12K, R19K, L20V, T24A, R40T, Q43K, K65D, S85D, S88A, and V93T (B4
      VHv34)
```

<400> SEQUENCE: 21

Gln Val Gln Leu Glu Gln Pro Gly Ala Glu Val Lys Lys Pro Gly Ala
1               5                   10                  15

Ser Val Lys Val Ser Cys Lys Ala Ser Gly Tyr Thr Phe Thr Ser Asn
            20                  25                  30

Trp Met His Trp Val Lys Gln Thr Pro Gly Lys Gly Leu Glu Trp Ile
        35                  40                  45

Gly Glu Ile Asp Pro Ser Asp Ser Tyr Thr Asn Tyr Asn Gln Lys Phe
    50                  55                  60

Asp Gly Lys Ala Lys Leu Thr Val Asp Lys Ser Ser Thr Ala Tyr
65                  70                  75                  80

Met Glu Val Ser Asp Leu Thr Ala Glu Asp Ser Ala Thr Tyr Tyr Cys
                85                  90                  95

Ala Arg Gly Ser Asn Pro Tyr Tyr Tyr Ala Met Asp Tyr Trp Gly Gln
            100                 105                 110

Gly Thr Ser Val Thr Val Ser Ser
        115                 120

<210> SEQ ID NO 22
<211> LENGTH: 30
<212> TYPE: PRT
<213> ORGANISM: Artificial Sequence
<220> FEATURE:
<223> OTHER INFORMATION: Amino acid sequence of B4 antibody heavy chain
      framework region 1 with variable amino acid residues X5, X12, X19,
      X20, X23, and X24 (B4 VHfr1)
<220> FEATURE:
<221> NAME/KEY: MISC_FEATURE
<222> LOCATION: (5)..(5)
<223> OTHER INFORMATION: Xaa is Gln or Glu
<220> FEATURE:
<221> NAME/KEY: MISC_FEATURE
<222> LOCATION: (12)..(12)
<223> OTHER INFORMATION: Xaa is Val or Lys
<220> FEATURE:
<221> NAME/KEY: MISC_FEATURE
<222> LOCATION: (19)..(19)
<223> OTHER INFORMATION: Xaa is Arg or Lys
<220> FEATURE:
<221> NAME/KEY: MISC_FEATURE
<222> LOCATION: (20)..(20)
<223> OTHER INFORMATION: Xaa is Leu or Val
<220> FEATURE:
<221> NAME/KEY: MISC_FEATURE
<222> LOCATION: (23)..(23)
<223> OTHER INFORMATION: Xaa is Lys, Glu, or Asp
<220> FEATURE:
<221> NAME/KEY: MISC_FEATURE
<222> LOCATION: (24)..(24)
<223> OTHER INFORMATION: Xaa is Thr or Ala

<400> SEQUENCE: 22

Gln Val Gln Leu Xaa Gln Pro Gly Ala Glu Val Xaa Lys Pro Gly Ala
1               5                   10                  15

Ser Val Xaa Xaa Ser Cys Xaa Xaa Ser Gly Tyr Thr Phe Thr
            20                  25                  30

<210> SEQ ID NO 23
<211> LENGTH: 14
<212> TYPE: PRT
<213> ORGANISM: Artificial Sequence
<220> FEATURE:
<223> OTHER INFORMATION: Amino acid sequence of B4 antibody heavy chain
      framework region 2 with variable amino acid residues X3, X5, X7,
      and X8 (B4 VHfr2)
<220> FEATURE:

```
<221> NAME/KEY: MISC_FEATURE
<222> LOCATION: (3)..(3)
<223> OTHER INFORMATION: Xaa is Lys or Arg
<220> FEATURE:
<221> NAME/KEY: MISC_FEATURE
<222> LOCATION: (5)..(5)
<223> OTHER INFORMATION: Xaa is Arg, Thr, or Ala
<220> FEATURE:
<221> NAME/KEY: MISC_FEATURE
<222> LOCATION: (7)..(7)
<223> OTHER INFORMATION: Xaa is Gly, Asp, or Glu
<220> FEATURE:
<221> NAME/KEY: MISC_FEATURE
<222> LOCATION: (8)..(8)
<223> OTHER INFORMATION: Xaa is Gln or Lys

<400> SEQUENCE: 23

Trp Val Xaa Gln Xaa Pro Xaa Xaa Gly Leu Glu Trp Ile Gly
1               5                   10

<210> SEQ ID NO 24
<211> LENGTH: 39
<212> TYPE: PRT
<213> ORGANISM: Artificial Sequence
<220> FEATURE:
<223> OTHER INFORMATION: Amino acid sequence of B4 antibody heavy chain
      framework region 3 with variable amino acid residues X6, X10, X26,
      X29, and X34 (B4 VHfr3)
<220> FEATURE:
<221> NAME/KEY: MISC_FEATURE
<222> LOCATION: (6)..(6)
<223> OTHER INFORMATION: Xaa is Lys, Asp, or Glu
<220> FEATURE:
<221> NAME/KEY: MISC_FEATURE
<222> LOCATION: (10)..(10)
<223> OTHER INFORMATION: Xaa is Lys, Glu, or Asp
<220> FEATURE:
<221> NAME/KEY: MISC_FEATURE
<222> LOCATION: (26)..(26)
<223> OTHER INFORMATION: Xaa is Ser, Asp, or Glu
<220> FEATURE:
<221> NAME/KEY: MISC_FEATURE
<222> LOCATION: (29)..(29)
<223> OTHER INFORMATION: Xaa is Ser or Ala
<220> FEATURE:
<221> NAME/KEY: MISC_FEATURE
<222> LOCATION: (34)..(34)
<223> OTHER INFORMATION: Xaa is Val or Thr

<400> SEQUENCE: 24

Tyr Asn Gln Lys Phe Xaa Gly Lys Ala Xaa Leu Thr Val Asp Lys Ser
1               5                   10                  15

Ser Ser Thr Ala Tyr Met Glu Val Ser Xaa Leu Thr Xaa Glu Asp Ser
            20                  25                  30

Ala Xaa Tyr Tyr Cys Ala Arg
        35

<210> SEQ ID NO 25
<211> LENGTH: 104
<212> TYPE: PRT
<213> ORGANISM: Homo sapiens

<400> SEQUENCE: 25

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Gly Val Asn Tyr Met
            20                  25                  30

His Trp Tyr Gln Gln Lys Pro Gly Thr Ser Pro Lys Arg Trp Ile Tyr
        35                  40                  45
```

```
Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys His Gln Arg Gly Ser Tyr Thr Phe Gly
                 85                  90                  95

Gly Gly Thr Lys Leu Glu Ile Lys
            100
```

<210> SEQ ID NO 26
<211> LENGTH: 104
<212> TYPE: PRT
<213> ORGANISM: Artificial Sequence
<220> FEATURE:
<223> OTHER INFORMATION: Amino acid sequence of B4 antibody light chain
      variable region with codons for amino acid substitutions V3A, S7E,
      and A54D (B4 VKv1)

<400> SEQUENCE: 26

```
Gln Ile Ala Leu Thr Gln Glu Pro Ala Ile Met Ser Ala Ser Pro Gly
 1               5                  10                  15

Glu Lys Val Thr Met Thr Cys Ser Ala Ser Ser Gly Val Asn Tyr Met
            20                  25                  30

His Trp Tyr Gln Gln Lys Pro Gly Thr Ser Pro Lys Arg Trp Ile Tyr
         35                  40                  45

Asp Thr Ser Lys Leu Asp Ser Gly Val Pro Ala Arg Phe Ser Gly Ser
        50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys His Gln Arg Gly Ser Tyr Thr Phe Gly
                 85                  90                  95

Gly Gly Thr Lys Leu Glu Ile Lys
            100
```

<210> SEQ ID NO 27
<211> LENGTH: 104
<212> TYPE: PRT
<213> ORGANISM: Artificial Sequence
<220> FEATURE:
<223> OTHER INFORMATION: Amino acid sequence of B4 antibody light chain
      variable region with codons for amino acid substitutions Q1D,
      I10T, M11L, and A54D (B4 VKv2)

<400> SEQUENCE: 27

```
Asp Ile Val Leu Thr Gln Ser Pro Ala Thr Leu Ser Ala Ser Pro Gly
 1               5                  10                  15

Glu Lys Val Thr Met Thr Cys Ser Ala Ser Ser Gly Val Asn Tyr Met
            20                  25                  30

His Trp Tyr Gln Gln Lys Pro Gly Thr Ser Pro Lys Arg Trp Ile Tyr
         35                  40                  45

Asp Thr Ser Lys Leu Asp Ser Gly Val Pro Ala Arg Phe Ser Gly Ser
        50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys His Gln Arg Gly Ser Tyr Thr Phe Gly
                 85                  90                  95

Gly Gly Thr Lys Leu Glu Ile Lys
            100
```

-continued

```
<210> SEQ ID NO 28
<211> LENGTH: 104
<212> TYPE: PRT
<213> ORGANISM: Artificial Sequence
<220> FEATURE:
<223> OTHER INFORMATION: Amino acid sequence of B4 antibody light chain
      variable region with codons for amino acid substitutions I10T,
      M11L, V19A, V29A, and S75E (B4 VKv3)

<400> SEQUENCE: 28
```

Gln Ile Val Leu Thr Gln Ser Pro Ala Thr Leu Ser Ala Ser Pro Gly
1               5                   10                  15

Glu Lys Ala Thr Met Thr Cys Ser Ala Ser Ser Gly Ala Asn Tyr Met
            20                  25                  30

His Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Glu Ser Met Glu Ala Glu
65                  70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys
            100

```
<210> SEQ ID NO 29
<211> LENGTH: 104
<212> TYPE: PRT
<213> ORGANISM: Artificial Sequence
<220> FEATURE:
<223> OTHER INFORMATION: Amino acid sequence of B4 antibody light chain
      variable region with codons for amino acid substitutions I10T,
      M11L, V19A, S51D, and L53T (B4 VKv4)

<400> SEQUENCE: 29
```

Gln Ile Val Leu Thr Gln Ser Pro Ala Thr Leu Ser Ala Ser Pro Gly
1               5                   10                  15

Glu Lys Ala Thr Met Thr Cys Ser Ala Ser Ser Gly Val Asn Tyr Met
            20                  25                  30

His Trp Tyr Gln Gln Lys Pro Gly Thr Ser Pro Lys Arg Trp Ile Tyr
        35                  40                  45

Asp Thr Asp Lys Thr Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys
            100

```
<210> SEQ ID NO 30
<211> LENGTH: 104
<212> TYPE: PRT
<213> ORGANISM: Artificial Sequence
<220> FEATURE:
<223> OTHER INFORMATION: Amino acid sequence of B4 antibody light chain
      variable region with codons for amino acid substitutions V3A, S7E,
      V19A, A54D, and S75E (B4 VKv11)

<400> SEQUENCE: 30
```

Gln Ile Ala Leu Thr Gln Glu Pro Ala Ile Met Ser Ala Ser Pro Gly
1               5                   10                  15

Glu Lys Ala Thr Met Thr Cys Ser Ala Ser Ser Gly Val Asn Tyr Met
                20                  25                  30

His Trp Tyr Gln Gln Lys Pro Gly Thr Ser Pro Lys Arg Trp Ile Tyr
            35                  40                  45

Asp Thr Ser Lys Leu Asp Ser Gly Val Pro Ala Arg Phe Ser Gly Ser
        50                  55                  60

Gly Ser Gly Thr Ser Tyr Ser Leu Thr Ile Glu Ser Met Glu Ala Glu
65                  70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys
            100

<210> SEQ ID NO 31
<211> LENGTH: 104
<212> TYPE: PRT
<213> ORGANISM: Artificial Sequence
<220> FEATURE:
<223> OTHER INFORMATION: Amino acid sequence of B4 antibody light chain
      variable region with codons for amino acid substitutions I10T,
      M11L, V19A, V29A, S51D, L53T, and S75E (B4 VKv34)

<400> SEQUENCE: 31

Gln Ile Val Leu Thr Gln Ser Pro Ala Thr Leu Ser Ala Ser Pro Gly
1               5                   10                  15

Glu Lys Ala Thr Met Thr Cys Ser Ala Ser Ser Gly Ala Asn Tyr Met
                20                  25                  30

His Trp Tyr Gln Gln Lys Pro Gly Thr Ser Pro Lys Arg Trp Ile Tyr
            35                  40                  45

Asp Thr Asp Lys Thr Ala Ser Gly Val Pro Ala Arg Phe Ser Gly Ser
        50                  55                  60

Gly Ser Gly Thr Ser Tyr Ser Leu Thr Ile Glu Ser Met Glu Ala Glu
65                  70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys
            100

<210> SEQ ID NO 32
<211> LENGTH: 23
<212> TYPE: PRT
<213> ORGANISM: Artificial Sequence
<220> FEATURE:
<223> OTHER INFORMATION: Amino acid sequence of B4 antibody light chain
      framework region 1 with variable amino acid residues X1, X3, X7,
      X10, X11 and X19 (B4 VKfr1)
<220> FEATURE:
<221> NAME/KEY: MISC_FEATURE
<222> LOCATION: (1)..(1)
<223> OTHER INFORMATION: Xaa is Gln or Asp
<220> FEATURE:
<221> NAME/KEY: MISC_FEATURE
<222> LOCATION: (3)..(3)
<223> OTHER INFORMATION: Xaa is Val or Ala
<220> FEATURE:
<221> NAME/KEY: MISC_FEATURE
<222> LOCATION: (7)..(7)
<223> OTHER INFORMATION: Xaa is Ser or Glu
<220> FEATURE:
<221> NAME/KEY: MISC_FEATURE
<222> LOCATION: (10)..(10)
<223> OTHER INFORMATION: Xaa is Ile or Thr
<220> FEATURE:
<221> NAME/KEY: MISC_FEATURE

```
<222> LOCATION: (11)..(11)
<223> OTHER INFORMATION: Xaa is Met or Leu
<220> FEATURE:
<221> NAME/KEY: MISC_FEATURE
<222> LOCATION: (19)..(19)
<223> OTHER INFORMATION: Xaa is Val or Ala

<400> SEQUENCE: 32

Xaa Ile Xaa Leu Thr Gln Xaa Pro Ala Xaa Xaa Ser Ala Ser Pro Gly
1               5                   10                  15

Glu Lys Xaa Thr Met Thr Cys
            20

<210> SEQ ID NO 33
<211> LENGTH: 7
<212> TYPE: PRT
<213> ORGANISM: Artificial Sequence
<220> FEATURE:
<223> OTHER INFORMATION: Amino acid sequence of B4 antibody light chain
      complementarity determining region 2 with variable amino acid
      residues X3, X5, and X6 (B4 VKcdr2)
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 33

Asp Thr Xaa Lys Xaa Xaa Ser
1               5

<210> SEQ ID NO 34
<211> LENGTH: 9
<212> TYPE: PRT
<213> ORGANISM: Artificial Sequence
<220> FEATURE:
<223> OTHER INFORMATION: Amino acid sequence of peptides of B4 V regions
      predicted to bind human HLA-DR alleles

<400> SEQUENCE: 34

Val Gln Leu Gln Gln Pro Gly Ala Glu
1               5

<210> SEQ ID NO 35
<211> LENGTH: 9
<212> TYPE: PRT
<213> ORGANISM: Artificial Sequence
<220> FEATURE:
<223> OTHER INFORMATION: Amino acid sequence of peptides of B4 V regions
      predicted to bind human HLA-DR alleles

<400> SEQUENCE: 35

Val Lys Pro Gly Ala Ser Val Arg Leu
1               5

<210> SEQ ID NO 36
<211> LENGTH: 9
<212> TYPE: PRT
<213> ORGANISM: Artificial Sequence
<220> FEATURE:
<223> OTHER INFORMATION: Amino acid sequence of peptides of B4 V regions
      predicted to bind human HLA-DR alleles

<400> SEQUENCE: 36

Val Arg Leu Ser Cys Lys Thr Ser Gly
1               5
```

```
<210> SEQ ID NO 37
<211> LENGTH: 9
<212> TYPE: PRT
<213> ORGANISM: Artificial Sequence
<220> FEATURE:
<223> OTHER INFORMATION: Amino acid sequence of peptides of B4 V regions
      predicted to bind human HLA-DR alleles

<400> SEQUENCE: 37

Trp Val Lys Gln Arg Pro Gly Gln Gly
1               5

<210> SEQ ID NO 38
<211> LENGTH: 9
<212> TYPE: PRT
<213> ORGANISM: Artificial Sequence
<220> FEATURE:
<223> OTHER INFORMATION: Amino acid sequence of peptides of B4 V regions
      predicted to bind human HLA-DR alleles

<400> SEQUENCE: 38

Tyr Asn Gln Lys Phe Lys Gly Lys Ala
1               5

<210> SEQ ID NO 39
<211> LENGTH: 9
<212> TYPE: PRT
<213> ORGANISM: Artificial Sequence
<220> FEATURE:
<223> OTHER INFORMATION: Amino acid sequence of peptides of B4 V regions
      predicted to bind human HLA-DR alleles

<400> SEQUENCE: 39

Phe Lys Gly Lys Ala Lys Leu Thr Val
1               5

<210> SEQ ID NO 40
<211> LENGTH: 9
<212> TYPE: PRT
<213> ORGANISM: Artificial Sequence
<220> FEATURE:
<223> OTHER INFORMATION: Amino acid sequence of peptides of B4 V regions
      predicted to bind human HLA-DR alleles

<400> SEQUENCE: 40

Tyr Met Glu Val Ser Ser Leu Thr Ser
1               5

<210> SEQ ID NO 41
<211> LENGTH: 9
<212> TYPE: PRT
<213> ORGANISM: Artificial Sequence
<220> FEATURE:
<223> OTHER INFORMATION: Amino acid sequence of peptides of B4 V regions
      predicted to bind human HLA-DR alleles

<400> SEQUENCE: 41

Val Tyr Tyr Cys Ala Arg Gly Ser Asn
1               5

<210> SEQ ID NO 42
<211> LENGTH: 9
<212> TYPE: PRT
<213> ORGANISM: Artificial Sequence
<220> FEATURE:
<223> OTHER INFORMATION: Amino acid sequence of peptides of B4 V regions
      predicted to bind human HLA-DR alleles
```

-continued

<400> SEQUENCE: 42

Ile Val Leu Thr Gln Ser Pro Ala Ile
1               5

<210> SEQ ID NO 43
<211> LENGTH: 9
<212> TYPE: PRT
<213> ORGANISM: Artificial Sequence
<220> FEATURE:
<223> OTHER INFORMATION: Amino acid sequence of peptides of B4 V regions
      predicted to bind human HLA-DR alleles

<400> SEQUENCE: 43

Val Leu Thr Gln Ser Pro Ala Ile Met
1               5

<210> SEQ ID NO 44
<211> LENGTH: 9
<212> TYPE: PRT
<213> ORGANISM: Artificial Sequence
<220> FEATURE:
<223> OTHER INFORMATION: Amino acid sequence of peptides of B4 V regions
      predicted to bind human HLA-DR alleles

<400> SEQUENCE: 44

Val Thr Met Thr Cys Ser Ala Ser Ser
1               5

<210> SEQ ID NO 45
<211> LENGTH: 9
<212> TYPE: PRT
<213> ORGANISM: Artificial Sequence
<220> FEATURE:
<223> OTHER INFORMATION: Amino acid sequence of peptides of B4 V regions
      predicted to bind human HLA-DR alleles

<400> SEQUENCE: 45

Val Asn Tyr Met His Trp Tyr Gln Gln
1               5

<210> SEQ ID NO 46
<211> LENGTH: 9
<212> TYPE: PRT
<213> ORGANISM: Artificial Sequence
<220> FEATURE:
<223> OTHER INFORMATION: Amino acid sequence of peptides of B4 V regions
      predicted to bind human HLA-DR alleles

<400> SEQUENCE: 46

Trp Ile Tyr Asp Thr Ser Lys Leu Ala
1               5

<210> SEQ ID NO 47
<211> LENGTH: 9
<212> TYPE: PRT
<213> ORGANISM: Artificial Sequence
<220> FEATURE:
<223> OTHER INFORMATION: Amino acid sequence of peptides of B4 V regions
      predicted to bind human HLA-DR alleles

<400> SEQUENCE: 47

Ile Tyr Asp Thr Ser Lys Leu Ala Ser
1               5

<210> SEQ ID NO 48
<211> LENGTH: 13

```
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 48
cgtaagtgga tcc                                                        13

<210> SEQ ID NO 49
<211> LENGTH: 12
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 49
gctagctcca gc                                                         12
```